(12) United States Patent
Zhu et al.

(10) Patent No.: US 11,912,695 B2
(45) Date of Patent: *Feb. 27, 2024

(54) BENZODIAZEPINE DERIVATIVES AS RSV INHIBITORS

(71) Applicant: ENANTA PHARMACEUTICALS, INC., Watertown, MA (US)

(72) Inventors: Kaicheng Zhu, Belmont, MA (US); Kevin McGrath, Brighton, MA (US); Solymar Negretti-Emmanuelli, Watertown, MA (US); Adam Szymaniak, Boston, MA (US); Jianming Yu, Plainsboro, NJ (US); In Jong Kim, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 17/574,718

(22) Filed: Jan. 13, 2022

(65) Prior Publication Data

US 2022/0227746 A1    Jul. 21, 2022

Related U.S. Application Data

(63) Continuation of application No. 16/821,290, filed on Mar. 17, 2020, now Pat. No. 11,254,664.

(60) Provisional application No. 62/821,094, filed on Mar. 20, 2019, provisional application No. 62/819,915, filed on Mar. 18, 2019.

(51) Int. Cl.
| | | |
|---|---|---|
| *C07D 413/14* | (2006.01) | |
| *A61K 31/5513* | (2006.01) | |
| *A61P 31/14* | (2006.01) | |
| *C07D 417/14* | (2006.01) | |
| *A61K 45/06* | (2006.01) | |

(52) U.S. Cl.
CPC ............ *C07D 413/14* (2013.01); *A61P 31/14* (2018.01); *C07D 417/14* (2013.01); *A61K 31/5513* (2013.01); *A61K 45/06* (2013.01)

(58) Field of Classification Search
CPC .... C07D 413/14; A61K 31/5513; A61P 31/14
See application file for complete search history.

(56) References Cited

U.S. PATENT DOCUMENTS

| | | |
|---|---|---|
| 4,010,153 A | 3/1977 | Kajfez et al. |
| 4,511,510 A | 4/1985 | Mauri |
| 4,988,692 A | 1/1991 | Gasc et al. |
| 5,571,809 A | 11/1996 | Hargrave et al. |
| 5,637,697 A | 6/1997 | Finch et al. |
| 5,646,140 A | 7/1997 | Sugg et al. |
| 5,681,833 A | 10/1997 | Castro et al. |
| 7,041,662 B2 | 5/2006 | Sattlegger et al. |
| 7,582,624 B2 | 9/2009 | Carter et al. |
| 8,999,969 B2 | 4/2015 | Mackman et al. |
| 9,617,289 B2 | 4/2017 | Tahri et al. |
| 9,732,098 B2 | 8/2017 | Hunt et al. |
| 9,957,281 B2 | 5/2018 | Shook et al. |
| 10,358,441 B2 | 7/2019 | Kim et al. |
| 10,398,706 B2 | 9/2019 | Shook et al. |

(Continued)

FOREIGN PATENT DOCUMENTS

| | | |
|---|---|---|
| CN | 109966244 A | 7/2019 |
| EP | 0167919 A2 | 1/1986 |

(Continued)

OTHER PUBLICATIONS

Lattmann, E. et al., "In vivo Evaluation of Substituted 3-Amino-1,4-benzodiazepines as Anti-depressant, Anxiolytic and Antinociceptive Agents", Arzneimittelforschung, 59(2), doi: 10.1055/s-0031-1296366, 2009, 61-71.
STN Registry database entry: CAS RN 1348594-72-8 (Entered STN: Dec. 4, 2011) (Year: 2011).
STN Registry database entry: CAS RN 1348849-53-5 (Entered STN: Dec. 5, 2011) (Year: 2011).
STN Registry database entry: CAS RN 1348924-24-2 (Entered STN: Dec. 5, 2011).
STN Registry database entry: CAS RN 1349463-13-3 (Entered STN: Dec. 6, 2011) (Year: 2011).

(Continued)

*Primary Examiner* — Shengjun Wang
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

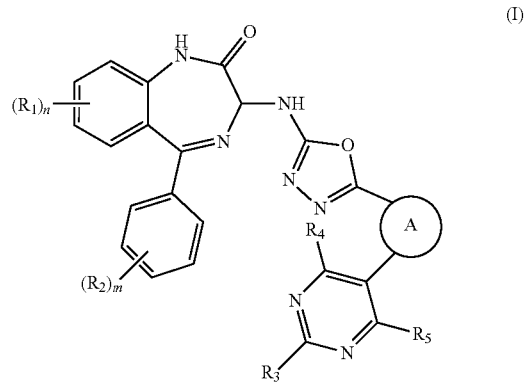

(I)

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

20 Claims, No Drawings

(56) References Cited

U.S. PATENT DOCUMENTS

| | | | |
|---|---|---|---|
| 10,865,215 | B2 | 12/2020 | Shook et al. |
| 11,254,664 | B2 * | 2/2022 | Zhu .................... C07D 417/14 |
| 2005/0261339 | A1 | 11/2005 | Ohi et al. |
| 2006/0040923 | A1 | 2/2006 | Carter et al. |
| 2006/0083741 | A1 | 4/2006 | Hoffman et al. |
| 2007/0142403 | A1 | 6/2007 | Powell et al. |
| 2007/0185094 | A1 | 8/2007 | Lattmann et al. |
| 2007/0185096 | A1 | 8/2007 | Powell et al. |
| 2007/0293482 | A1 | 12/2007 | Dowdell et al. |
| 2008/0139536 | A1 | 6/2008 | Dowdell et al. |
| 2009/0274655 | A1 | 11/2009 | Grimes et al. |
| 2010/0015063 | A1 | 1/2010 | Carter et al. |
| 2010/0168384 | A1 | 7/2010 | Mdcaniel et al. |
| 2011/0274654 | A1 | 11/2011 | Bahadoor et al. |
| 2012/0196846 | A1 | 8/2012 | Mackman et al. |
| 2014/0038947 | A1 | 2/2014 | Glick et al. |
| 2014/0100365 | A1 | 4/2014 | Gavai et al. |
| 2014/0148573 | A1 | 5/2014 | Ku et al. |
| 2014/0328796 | A1 | 11/2014 | Phadke et al. |
| 2015/0038514 | A1 | 2/2015 | Grunenberg et al. |
| 2015/0065504 | A1 | 3/2015 | Wang et al. |
| 2015/0218111 | A1 | 8/2015 | Gavai et al. |
| 2015/0299210 | A1 | 10/2015 | Bailey et al. |
| 2016/0244460 | A1 | 8/2016 | Wang et al. |
| 2017/0022221 | A1 | 1/2017 | Blaisdell et al. |
| 2017/0226127 | A1 | 8/2017 | Estrada et al. |
| 2017/0226129 | A1 | 8/2017 | Yu et al. |
| 2017/0305935 | A1 | 10/2017 | Hunt et al. |
| 2017/0355717 | A1 | 12/2017 | Hunt et al. |
| 2018/0065932 | A1 | 3/2018 | Wang et al. |
| 2018/0193352 | A1 | 7/2018 | Shook et al. |
| 2018/0237425 | A1 | 8/2018 | Kim et al. |
| 2018/0258102 | A1 | 9/2018 | Shook et al. |
| 2018/0354912 | A1 | 12/2018 | Or et al. |
| 2019/0002478 | A1 | 1/2019 | Kim et al. |
| 2019/0002479 | A1 | 1/2019 | Kim et al. |
| 2019/0023692 | A1 | 1/2019 | Tahri et al. |
| 2019/0040084 | A1 | 2/2019 | Yu et al. |
| 2019/0092791 | A1 | 3/2019 | Hunt et al. |
| 2019/0152968 | A1 | 5/2019 | Blaisdell et al. |
| 2019/0177283 | A1 | 6/2019 | Hague |
| 2019/0192535 | A1 | 6/2019 | Shook et al. |
| 2019/0202841 | A1 | 7/2019 | Hunt et al. |
| 2019/0315766 | A1 | 10/2019 | Yu et al. |
| 2021/0238188 | A1 | 8/2021 | He et al. |
| 2022/0356189 | A1 | 11/2022 | Szymaniak et al. |

FOREIGN PATENT DOCUMENTS

| | | |
|---|---|---|
| EP | 0703222 A1 | 3/1996 |
| JP | 2004043456 A | 2/2004 |
| WO | 9308175 A1 | 4/1993 |
| WO | 9426718 A1 | 11/1994 |
| WO | 2004026843 A1 | 4/2004 |
| WO | 2004052348 A2 | 6/2004 |
| WO | 2004106310 A1 | 12/2004 |
| WO | 2005042530 A1 | 5/2005 |
| WO | 2005089769 A1 | 9/2005 |
| WO | 2005090319 A1 | 9/2005 |
| WO | 2006081389 A1 | 8/2006 |
| WO | 2010103306 A1 | 9/2010 |
| WO | 2011005842 A1 | 1/2011 |
| WO | 2011112186 A1 | 9/2011 |
| WO | 2011151651 A1 | 12/2011 |
| WO | 2012012776 A1 | 1/2012 |
| WO | 2012068622 A1 | 5/2012 |
| WO | 2012080446 A1 | 6/2012 |
| WO | 2012080447 A1 | 6/2012 |
| WO | 2012080449 A1 | 6/2012 |
| WO | 2012080450 A1 | 6/2012 |
| WO | 2012080451 A1 | 6/2012 |
| WO | 2013096681 A1 | 6/2013 |
| WO | 2013186332 A1 | 12/2013 |
| WO | 2013186334 A1 | 12/2013 |
| WO | 2014031784 A1 | 2/2014 |
| WO | 2014047369 A1 | 3/2014 |
| WO | 2014047397 A1 | 3/2014 |
| WO | 2014060411 A1 | 4/2014 |
| WO | 2014125444 A1 | 8/2014 |
| WO | 2014184350 A1 | 11/2014 |
| WO | 2014186035 A1 | 11/2014 |
| WO | 2014209983 A1 | 12/2014 |
| WO | 2015026792 A1 | 2/2015 |
| WO | 2015110446 A1 | 7/2015 |
| WO | 2016018697 A1 | 2/2016 |
| WO | 2016022464 A1 | 2/2016 |
| WO | 2016055791 A1 | 4/2016 |
| WO | 2016055792 A1 | 4/2016 |
| WO | 2016097761 A1 | 6/2016 |
| WO | 2016138158 A1 | 9/2016 |
| WO | 2016166546 A1 | 10/2016 |
| WO | 2017015449 A1 | 1/2017 |
| WO | 2017123864 A1 | 7/2017 |
| WO | 2017123884 A1 | 7/2017 |
| WO | 2017175000 A1 | 10/2017 |
| WO | 2019067864 A1 | 4/2019 |
| WO | 2021066922 A1 | 4/2021 |
| WO | 2021198981 A1 | 10/2021 |

OTHER PUBLICATIONS

STN Registry database entry: CAS RN 1349533-81-8 (Entered STN: Dec. 6, 2011) (Year: 2011).

STN Registry database entry: CAS RN 1349749-23-0 (Entered STN: Dec. 6, 2011) (Year: 2011).

STN Registry database entry: CAS RN 1350148-32-1 (Entered STN: Dec. 7, 2011).

U.S. Appl. No. 16/930,622, filed Jul. 16, 2020.

PUBCHEM-CID: 10595203, p. 3, Fig, Oct. 25, 2006, 1-9.

"4-(2-Hydroxyethoxy)-3-methoxy-N-[3,3,3-1-22 trifluoro-2-[7-(4-fluorophenyl)-3-[2-(methylamino )ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https:l/pubchem.ncbi.nlm.nih.gov/compound/139332032).

"'N-[(2R)-2-[(3S)-3-Amino-7-(3-chloro-4-A fluorophenyl)-3-methyl-2H-furo[2,3-c]pyridin-5-yl]-3,3,3-trifluoro-2-hydroxypropyl]-4-ethoxy-3-methoxybenzamide'", Pubchem Compound Record for CID 117923975, U.S. National Library of Medicine, Feb. 23, 2016 (Feb. 23, 2016), pp. 1-9 (https://pubchem.ncbi.nlm.nih.gov/compound/117923975); p. 2.

"N-[(2R)-2-[3-(Aminomethyl)-7-(4-fluorophenyl)-1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.

"'N-[2-[8-[4-Fluoro-3-(1-fluoroethyl)phenyl]-4-iodo-4-methyl-2,3-dihydropyrano[2,3-]pyridin-6-yl]-2-oxoethyl]-3-methoxy-4-[2-[(4-methoxyphenyl)methoxy]ethoxy]benzamide'", Pubchem Compound Record for CID 117924454, U.S. National library of Medicine, Feb. 23, 2016 (Feb. 23, 2016), pp. 1-8 (https:l/pubchem.ncbi.nlm.nih.gov/compound/117924454); p. 2.

Albright, et al., (Document No. 129:54301) retreived from STN; entered in STN on Jun. 17, 1998.

Albright, et al., (Document No. 130:153583) retreived from STN; entered in STN on Feb. 16, 1999.

Andrzej, et al., (Document No. 144:274313) retreved from STN; entered in STN on Mar. 3, 2006.

Aquino, C. J. et al., "Discovery of 1,5-Benzodiazepines with Peripheral Cholecystokinin (CCK-A) Receptor Agonist Activity. 1. Optimization of the Agonist "Trigger"", J. Med. Chem., 39, 1996, 562-569.

Armstrong, et al., "An Efficient Asymmetric Synthesis of (R)-3-Amino-2,3,4,5-tetrahydro-1H-[1]benzazepine-2-one", Tetrahedron Letters, 35(20), 1994, 3239-3242.

Bond, S. et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 2015, 976-981.

(56) References Cited

OTHER PUBLICATIONS

Carter, M. C. et al., "1,4-Benzodiazepines as Inhibitors of Respiratory Syncytial Virus", Journal of Medicinal Chemistry, vol. 49, Mar. 9, 2006, 2311-2319.
Chapman, J. et al., "RSV604, a Novel Inhibitor of Respiratory Syncytial Virus Replication", Antimicrobial Agents and Chemotherapy, vol. 51, No. 9, 2007, 3346-3353.
Contreras-Romo, M. et al., "Exploring the Ligand Recognition Properties of the Human Vasopressin V1a Receptor Using QSAR and Molecular Modeling Studies", Chem. Biol. Drug. Des., vol. 83, 2014, 207-223.
Fernandez, H. et al., "Ribavirin: A Clinical Overview", Euro J. Epidemiology, vol. 2, No. 1, Mar. 1, 1986, 1-14.
Fordyce, et al., "Discovery of novel benzothienoazepine derivatives as potent inhibitors of respiratory syncytial virus", Bioorganic & Medicinal Chemistry Letters, 27, 2017, 2201-2206.
Heeney, et al., (Document No. 153:359062) retreved from STN; entered in STN on Sep. 2, 2010.
Henderson, E. A. et al., "1,4-Benzodiazepines as Inhibitors of Respiratory Syncytial Virus. The Identification of a Clinical Candidate", Journal of Medicinal Chemistry, vol. 50, 2007, 1685-1692.
Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.
Kozlova, A. et al., "Current State on Tryptophan 2,3-Dioxygenase Inhibitors: a Patent Review", Expert Opinion on Therapeutic Patents, vol. 29, Iss. 1, 2019, 1-32.
Lee, et al., (Document No. 140:69941) retrieved from STN; entered in STN on Jul. 8, 2003.
Mackman, R. L. et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.
Mayo Clinic Staff, Respiratory syncytial virus (RSV) [online], retrieved from from internet on Jun. 25, 2017 .; URL http://www.mayoclinic.org/diseases-condiitons/respiratory-syncytial-virus/basics/prevention.
Offel, M. et al., "Synthesis of Substituted 3-Anilino-5-phenyl-I,3-dihydro-2H-I, 4-benzodiazepine-2-ones and their Evaluation as Cholecystokinin-Ligands", Archiv Der Pharmazie, vol. 339, No. 4, Apr. 1, 2006, 163-173.
Olszewska, W. et al., "Emerging drugs for respiratory syncytial virus infection", Expert Opin. Emerg. Drugs, 14(2), 2009, 207-217.
Peesapati, et al., (Document No. 120:244848) retreved from STN; entered in STN on May 14, 1994.
Perron, M. et al., "GS-5806 Inhibits a Broad Range of Respiratory Syncytial Virus Clinical Isolates by Blocking the Virus-Cell Fusion Process", Antimicrobial Agents and Chemotherapy, 60(3), 2016, 1264-1273.
Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.
Setoi, H. et al., "Preparation of heterocyclylbenzamide derivatives as vasopressin antagonists", Document No. 131:116236, retrieved from STN; entered in STN on Aug. 6, 1999, Aug. 6, 1999.
Stein, D. S. et al., "Oral ribavirin treatment of influenza A and B", Antimicrobial Agents and Chemotherapy, vol. 31, No. 1, URL:http://dx.doi.org/10.ll28/AAC.31.8.l285>, Aug. 1987, 1285-1287.
Sudo, K. et al., "YM-53403, a unique anti-respiratory syncytial virus agent with a novel mechanism of action", Antiviral Research, 2005, vol. 65, 2005, 125-131.
Wang, et al., (Document No. 160:385666) retrieved from STN; entered in STN on Feb. 27, 2014.
Wang, G. et al., "Discovery of 4'-Chloromethyl-2'-deoxy-3',5'-di-O-isobutyryl-2'-fluorocytidine (ALS-8176), A First-in-Class RSV Polymerase Inhibitor for Treatment of Human Respiratory Syncytial Virus Infection", J. Med. Chem., 58, 2015, 1862-1878.
Xiong, et al., (Document No. 160:101182) retrieved from STN; entered in STN on Nov. 12, 2013.
Xiong, H., "Discovery of a Potent Respiratory Syncytial Virus RNA Polymerase Inhibitor", Bioorganic & Medicinal Chemistry Letters, 23, 2013, 6789-6793.
Zheng, et al., (Document No. 161 :399872) retrieved from STN; entered in STN on Jul. 23, 2014.

\* cited by examiner

BENZODIAZEPINE DERIVATIVES AS RSV INHIBITORS

RELATED APPLICATIONS

This application is a continuation of U.S. application Ser. No. 16/821,290, filed on Mar. 17, 2020, which claims the benefit of U.S. Provisional Application No. 62/819,915, filed on Mar. 18, 2019 and U.S. Provisional Application No. 62/821,094, filed on Mar. 20, 2019. The entire teachings of the above applications are incorporated herein by reference.

TECHNICAL FIELD

The present invention relates generally to compounds and pharmaceutical compositions useful as Respiratory Syncytial Virus (RSV) inhibitors. Specifically, the present invention relates to benzodiazepine derivatives that can inhibit RSV activities and for treating RSV infection.

BACKGROUND OF THE INVENTION

Human respiratory syncytial virus (HRSV) is a negative-sense, single stranded, RNA paramyxovirus (K M. Empey, et al., *Rev. Anti-Infective Agents,* 2010, 50(1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2015/110446, WO 2017/009316, 1 *Med. Chem.* 2015, 58, 1630-1643, *Bioorg. Med. Chem. Lett.,* 2015, 25, 976-981 and *Nat. Commun.,* 2017, 8, 167. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2011/005842, WO 2013/242525, WO 2014/031784, WO 2015/026792, WO 2016/0055791, WO 2016/138158 and *J. Med. Chem.* 2015, 58, 1862-1878.

There is a need for the development of effective treatments for HRSV. The present invention has identified compounds that are aminoheteroaryl substituted benzodiazepines, and inhibit HRSV. The invention includes methods to prepare the compounds as well as methods of using these compounds to treat disease.

SUMMARY OF THE INVENTION

The present invention provides compounds represented by Formula (I), and pharmaceutically acceptable salts, esters or prodrugs thereof that can be used to treat or prevent viral (particularly HRSV) infection:

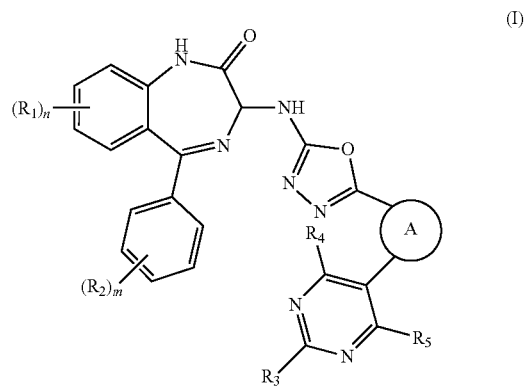

(I)

wherein:
A is optionally substituted heteroaryl; preferably A is an optionally substituted heteroaryl having at least one pair of adjacent carbon atoms; more preferably A is optionally substituted pyridinyl or optionally substituted thiazolyl;
n is 0, 1, 2, 3, or 4, preferably n is 0 or 1;
m is 0, 1, 2, 3, or 4, preferably m is 0 or 1;
$R_1$ and $R_2$ are each independently selected from the group consisting of:
  1) Halogen;
  2) —CN;
  3) Optionally substituted —$C_1$-$C_8$ alkyl;
  4) Optionally substituted —$C_2$-$C_8$ alkenyl;
  5) Optionally substituted —$C_2$-$C_8$ alkynyl; and
  6) Optionally substituted —$C_1$-$C_8$ alkoxyl;
$R_3$ is selected from the group consisting of:
  1) Hydrogen;
  2) Halogen;
  3) —CN;
  4) —$NR_6R_7$;
  5) Optionally substituted —$C_1$-$C_8$ alkyl;
  6) Optionally substituted —$C_1$-$C_8$ alkoxyl;
  7) Optionally substituted —$C_2$-$C_8$ alkenyl;
  8) Optionally substituted —$C_2$-$C_8$ alkynyl;
  9) Optionally substituted —$C_3$-$C_8$ cycloalkyl;
  10) Optionally substituted —$C_3$-$C_8$ cycloalkenyl;
  11) Optionally substituted 3- to 8-membered heterocyclyl;
  12) Optionally substituted aryl; and
  13) Optionally substituted heteroaryl;
    wherein $R_6$ and $R_7$ are each independently selected from the group consisting of:
    1) Hydrogen;
    2) Optionally substituted —$C_1$-$C_8$ alkyl;

3) Optionally substituted —$C_3$-$C_8$ cycloalkyl;
4) Optionally substituted —$C_3$-$C_8$ cycloalkenyl;
5) Optionally substituted 3- to 8-membered heterocyclic;
6) Optionally substituted aryl; and
7) Optionally substituted heteroaryl;
    alternatively, $R_6$ and $R_7$ are taken together with the nitrogen atom to which they are attached to form a heterocyclic ring; and
$R_4$ and $R_5$ are each independently selected from the group consisting of:
  1) Hydrogen;
  2) Halogen;
  3) —CN;
  4) Optionally substituted —$C_1$-$C_8$ alkyl;
  5) Optionally substituted —$C_1$-$C_8$ alkoxyl;
  6) Optionally substituted —$C_2$-$C_8$ alkenyl;
  7) Optionally substituted —$C_2$-$C_8$ alkynyl;
  8) Optionally substituted —$C_3$-$C_8$ cycloalkyl;
  9) Optionally substituted —$C_3$-$C_8$ cycloalkenyl; and
  10) Optionally substituted 3- to 8-membered heterocyclic.

Each preferred group stated above can be taken in combination with one, any or all other preferred groups.

DETAILED DESCRIPTION OF THE INVENTION

In one embodiment of the present invention is a compound represented by Formula (I) as described above, or a pharmaceutically acceptable salt, ester or prodrug thereof.

The carbon atom at position 3 of the benzodiazepine ring system of the compounds of the invention is chiral. Thus, compounds of the invention can have the stereochemistry depicted in Formula (Ia) or (Ib):

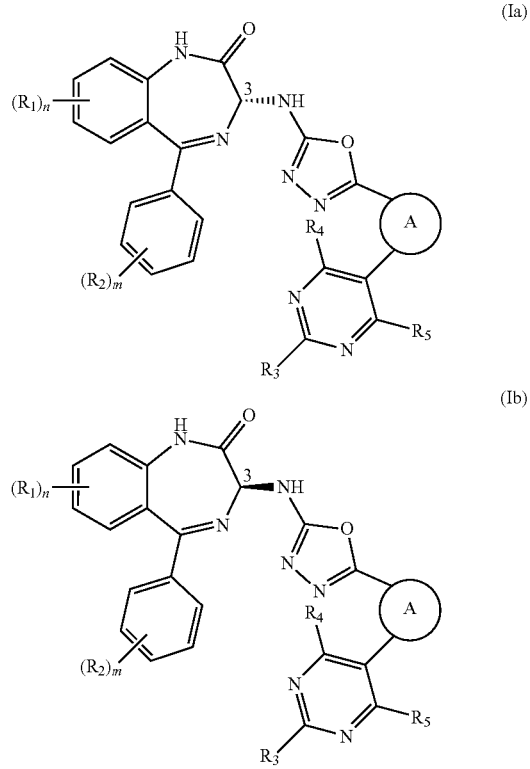

wherein $R_1$, $R_2$, $R_3$, $R_4$, $R_5$, A, n and m are previously defined. A composition of the invention can comprise a compound of the invention as a racemic mixture of Formula (Ia) and Formula (Ib), a pure enantiomer of either Formula (Ia) or Formula (Ib), or an excess of one enantiomer over the other. For example, the composition can comprise the compound in an enantiomeric excess of at least 5, 10, 20, 30, 40, 50, 60, 70, 80 or 90%. In one embodiment, the enantiomeric excess is at least 95%. In compounds of the invention having two or more chiral atoms, such compounds can be present in a composition as a pure stereoisomer or a mixture of stereoisomers, such as a racemic mixture or a mixture of diasteromers. In one embodiment, a composition of the invention comprises a racemic mixture, a single stereoisomer or enantiomers with an enantiomeric excess of at least 5, 10, 20, 30, 40, 50, 60, 70, 80, 90 or 95%.

In a preferred embodiment, a compound of the invention is represented by Formula (Ib). Compositions of the invention preferably comprise a substantially pure compound of Formula (Ib), or a mixture of a compound of Formula (Ib) and the corresponding compound of Formula (Ia), with an enantiomeritc excess of the compound of Formula (Ib) as discussed above.

In certain embodiments of the compounds of Formula (I), the 1,3,4-oxadiazole ring and the pyrimidine ring are attached to adjacent atoms of ring A. Preferably, the 1,3,4-oxadiazole ring and the pyrimidine ring are attached to adjacent ring carbon atoms of ring A.

In certain embodiments, the present invention relates to compounds of Formula (I), and pharmaceutically acceptable salts thereof, wherein $R_1$ is halogen or optionally substituted methyl. In certain embodiments, the present invention relates to compounds of Formula (I) and pharmaceutically acceptable salts thereof, wherein $R_1$ is F.

In certain embodiments, the present invention relates to compounds of Formula (I), and pharmaceutically acceptable salts thereof, wherein $R_2$ is halogen, or optionally substituted methyl. In certain embodiments, the present invention relates to compounds of Formula (I) and pharmaceutically acceptable salts thereof, wherein $R_1$ is F.

In certain embodiments, the present invention relates to compounds of Formula (I), and pharmaceutically acceptable salts thereof, wherein $R_3$ is optionally substituted —$C_1$-$C_8$ alkyl, optionally substituted —$C_3$-$C_8$ cycloalkyl or optionally substituted —$C_3$-$C_8$ cycloalkenyl. In certain embodiments, the present invention relates to compounds of Formula (I), and pharmaceutically acceptable salts thereof, wherein $R_3$ is optionally substituted —$C_1$-$C_8$ alkyl, or optionally substituted —$C_3$-$C_8$ cycloalkyl. In certain embodiments, the present invention relates to compounds of Formula (I), and pharmaceutically acceptable salts thereof, wherein $R_3$ is optionally substituted methyl, optionally substituted ethyl or optionally substituted cyclopropyl.

In certain embodiments, the present invention relates to compounds of Formula (I), and pharmaceutically acceptable salts thereof, wherein $R_4$ is hydrogen, halogen, —CN, or optionally substituted methyl. In certain embodiments, the present invention relates to compounds of Formula (I) and pharmaceutically acceptable salts thereof, wherein $R_4$ is H or halogen. In certain embodiments, the present invention relates to compounds of Formula (I) and pharmaceutically acceptable salts thereof, wherein $R_4$ is H.

In certain embodiments, the present invention relates to compounds of Formula (I), and pharmaceutically acceptable salts thereof, wherein $R_5$ is hydrogen, halogen, —CN, or optionally substituted methyl. In certain embodiments, the present invention relates to compounds of Formula (I) and pharmaceutically acceptable salts thereof, wherein $R_5$ is H or halogen. In certain embodiments, the present invention relates to compounds of Formula (I) and pharmaceutically acceptable salts thereof, wherein $R_5$ is H.

In certain embodiments, the present invention relates to compounds of Formula (I), and pharmaceutically acceptable salts thereof, wherein $R_4$ is H, and $R_5$ is H.

In certain embodiments, the present invention relates to compounds of Formula (I), and pharmaceutically acceptable salts thereof, wherein n is 0.

In certain embodiments, the present invention relates to compounds of Formula (I), and pharmaceutically acceptable salts thereof, wherein m is 0.

In certain embodiments, the present invention relates to compounds of Formula (I), and pharmaceutically acceptable salts thereof, wherein n is 0, and m is 0.

In certain embodiments, the present invention relates to compounds of Formula (I), and pharmaceutically acceptable salts thereof, wherein n is 0, m is 0, $R_3$ is optionally substituted methyl, optionally substituted ethyl or optionally substituted cyclopropyl, $R_4$ is H, and $R_5$ is H.

In certain embodiments, the present invention relates to compounds of Formula (I), and pharmaceutically acceptable salts thereof, wherein n is 1, m is 0, and $R_1$ is F.

In certain embodiments, the present invention relates to compounds of Formula (I), and pharmaceutically acceptable salts thereof, wherein n is 1, m is 0, $R_1$ is F, $R_3$ is optionally substituted methyl, optionally substituted ethyl or optionally substituted cyclopropyl, $R_4$ is H, and $R_5$ is H.

In certain embodiments, the present invention relates to compounds of Formula (I), and pharmaceutically acceptable salts thereof, wherein A is optionally substituted pyridinyl.

In certain embodiments, the present invention relates to compounds of Formula (I), and pharmaceutically acceptable salts thereof, wherein A optionally substituted thiazolyl.

In certain embodiments, the present invention relates to compounds of Formula (I), and pharmaceutically acceptable salts thereof, wherein A is selected from, but not limited to, the groups set forth below, where one of the indicated valences is the point of attachment of the carbon atom of the 1,3,4-oxadiazole, and the other is the point of attachment to the carbon atom of the pyrimidine:

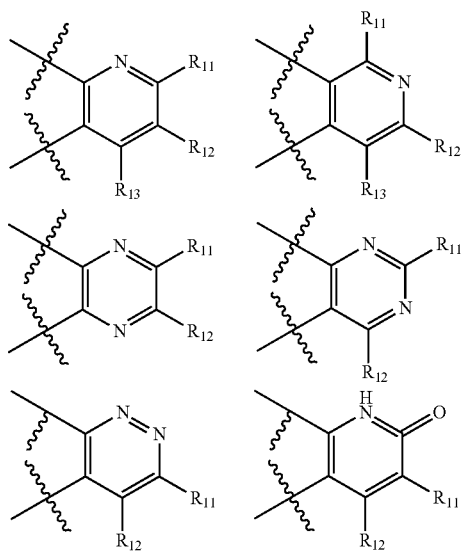

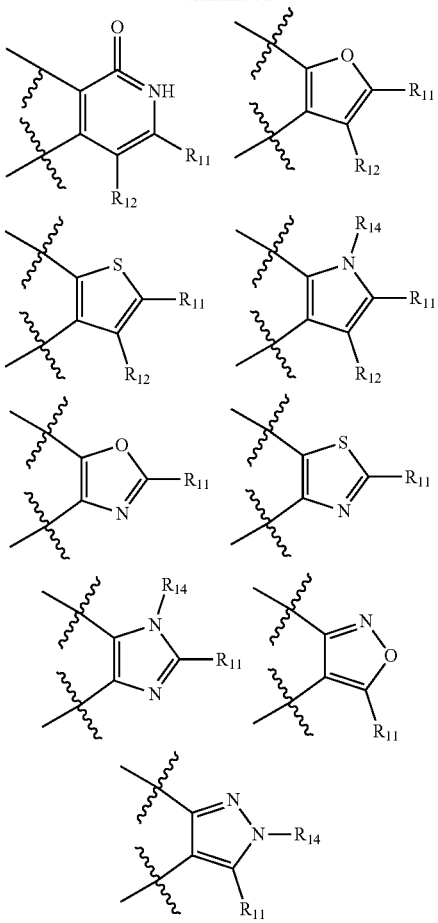

wherein $R_{11}$, $R_{12}$, and $R_{13}$ are each independently selected from the group consisting of:
1) Hydrogen;
2) Halogen;
3) —$NO_2$;
4) —$NR_6R_7$;
5) —CN;
6) Optionally substituted —$C_1$-$C_8$ alkyl;
7) Optionally substituted —$C_1$-$C_8$ alkoxyl;
8) Optionally substituted —$C_2$-$C_8$ alkenyl;
9) Optionally substituted —$C_2$-$C_8$ alkynyl;
10) Optionally substituted —$C_3$-$C_8$ cycloalkyl;
11) Optionally substituted —$C_3$-$C_8$ cycloalkenyl;
12) Optionally substituted 3- to 8-membered heterocyclic;
13) Optionally substituted aryl; and
14) Optionally substituted heteroaryl;

$R_{14}$ is selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted —$C_3$-$C_8$ cycloalkenyl;
7) Optionally substituted 3- to 8-membered heterocyclic;
8) Optionally substituted aryl; and
9) Optionally substituted heteroaryl;

wherein $R_6$ and $R_7$ are as previously defined; preferably $R_{11}$, $R_{12}$, and $R_{13}$ are each independently selected from hydrogen, halogen, optionally substituted —$C_1$-$C_3$ alkyl, optionally substituted —C$_1$-C$_3$ alkoxyl or optionally substituted —C$_3$-C$_6$ cycloalkyl. More preferably R$_{11}$, R$_{12}$, and R$_{13}$ are each independently optionally hydrogen or substituted methyl. In one embodiment, A is pyridyl, R$_{11}$ and R$_{13}$ are both hydrogen and R$_{12}$ is methyl or substituted methyl, such as CF$_3$. In another embodiment, A is thiazolyl and R$_{11}$ is hydrogen, methyl or substituted methyl, such as CF$_3$. R$_{14}$ is preferably hydrogen or C$_1$-C$_4$-alkyl; more preferably hydrogen or methyl.

In one embodiment of the invention is a compound represented by one of Formulae (II-1)~(II-6), or a pharmaceutically acceptable salt, ester or prodrug thereof:

(II-1)
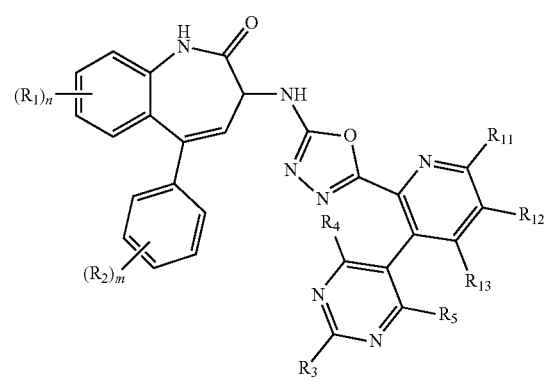

(II-2)
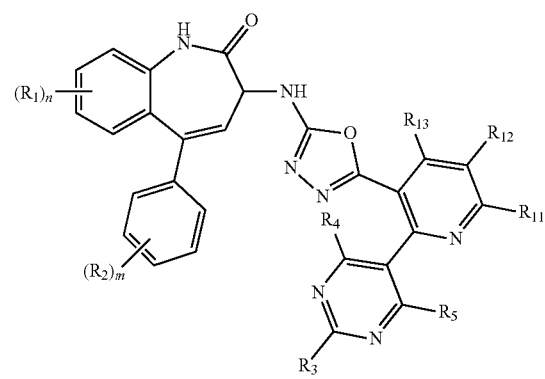

(II-3)
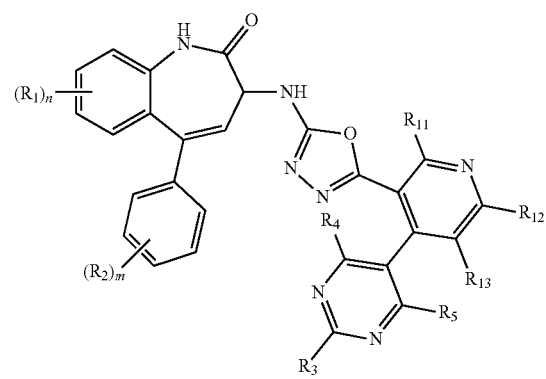

(II-4)
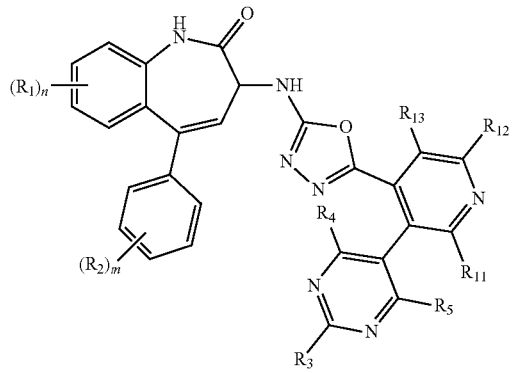

(II-5)
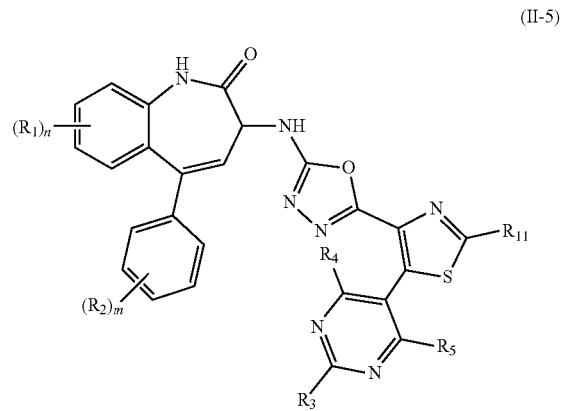

(II-6)
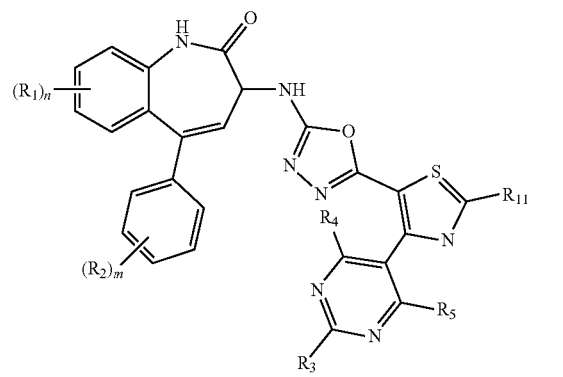

wherein R$_1$, R$_2$, R$_3$, R$_4$, R$_5$, n, m, R$_{11}$, R$_{12}$, and R$_{13}$ are as previously defined.

In another embodiment of the invention is a compound represented by one of Formulae (IIb-1)~(IIb-6), or a pharmaceutically acceptable salt, ester or prodrug thereof:

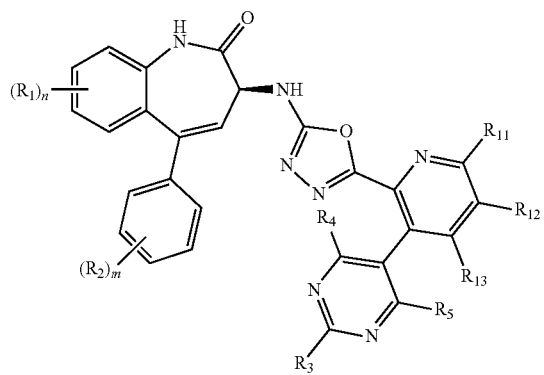
(IIb-1)
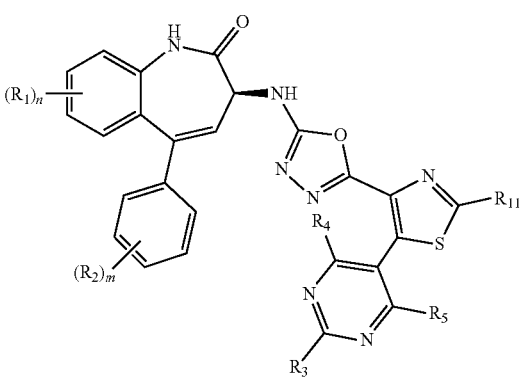
(IIb-5)
(IIb-2)
(IIb-6)
(IIb-3)
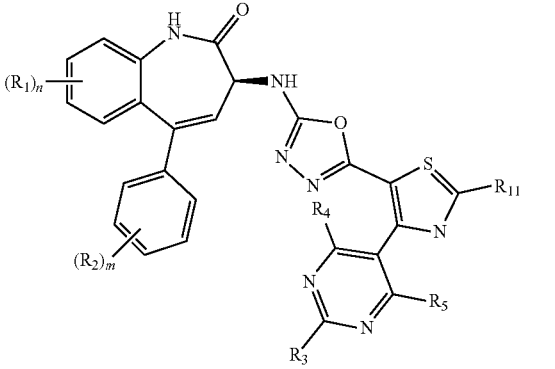
wherein $R_1$, $R_2$, $R_3$, $R_4$, $R_5$, n, m, $R_{11}$, $R_{12}$, and $R_{13}$ are as previously defined.
In another embodiment of the invention is a compound represented by one of Formulae (III-1)~(III-6), or a pharmaceutically acceptable salt, ester or prodrug thereof:
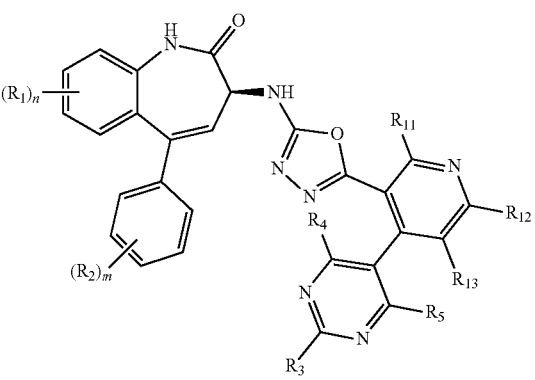
(IIb-4)
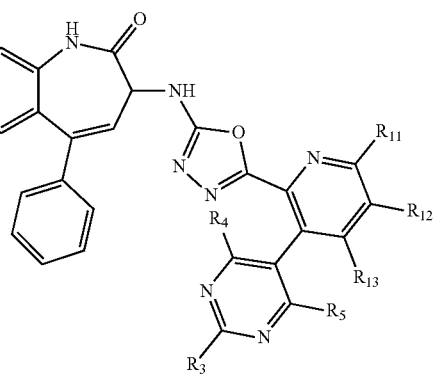
(III-1)

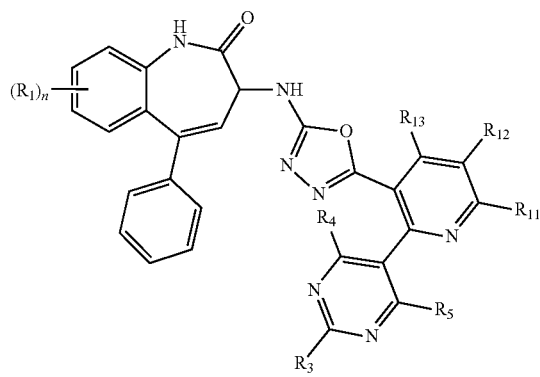
(III-2)
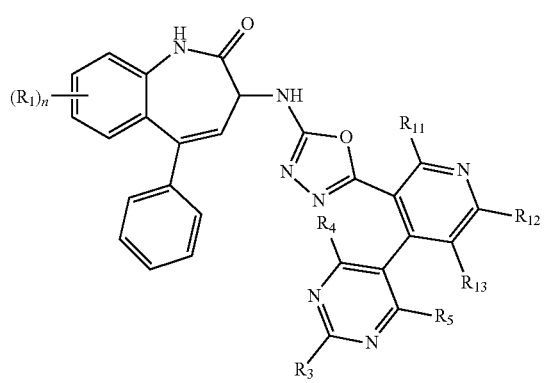
(III-3)
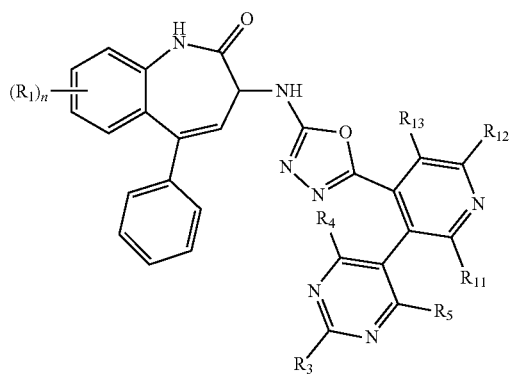
(III-4)
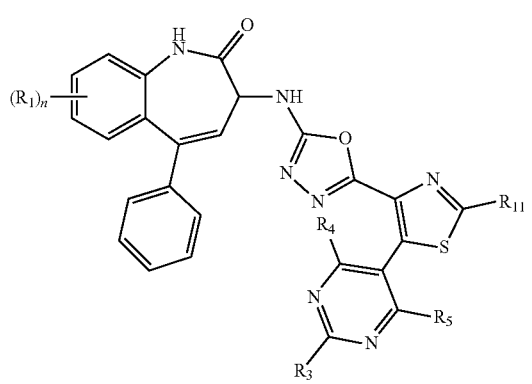
(III-5)
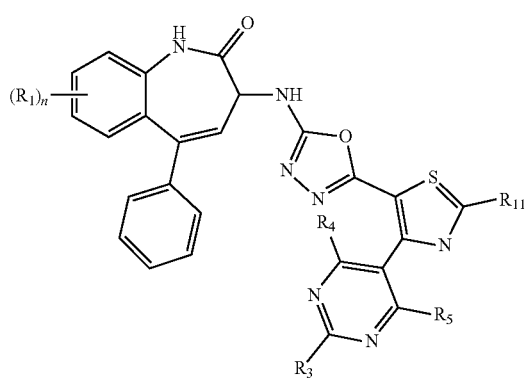
(III-6)
wherein $R_1$, $R_3$, $R_4$, $R_5$, n, $R_{11}$, $R_{12}$, and $R_{13}$, are as previously defined.
In another embodiment of the invention is a compound represented by one of Formulae (IIIb-1)~(IIIb-6), or a pharmaceutically acceptable salt, ester or prodrug thereof:
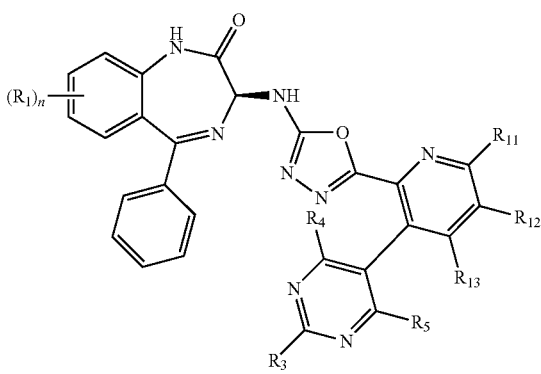
(IIIb-1)
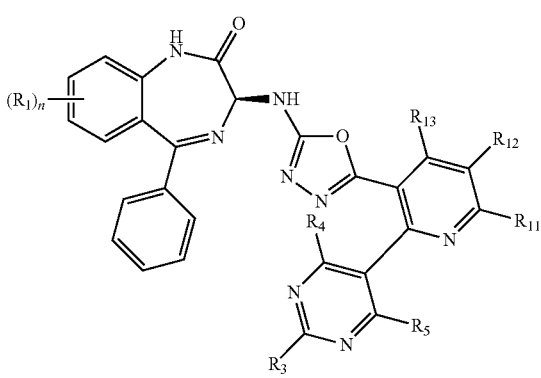
(IIIb-2)

-continued
(IIIb-3)
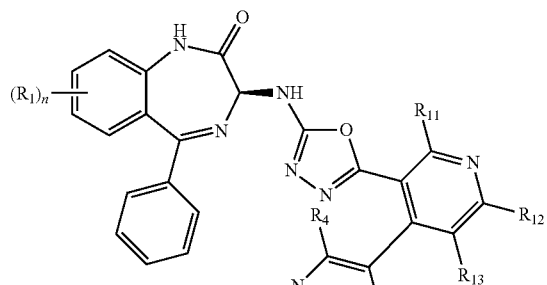
(IIIb-4)
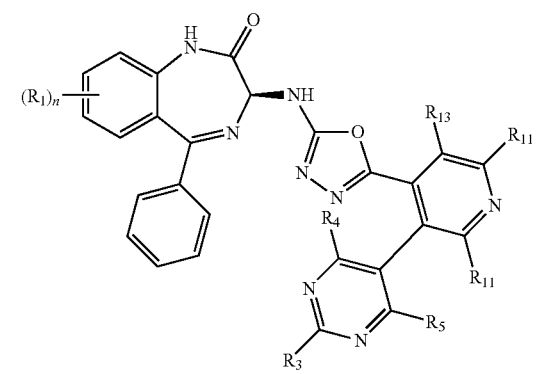
(IIIb-5)
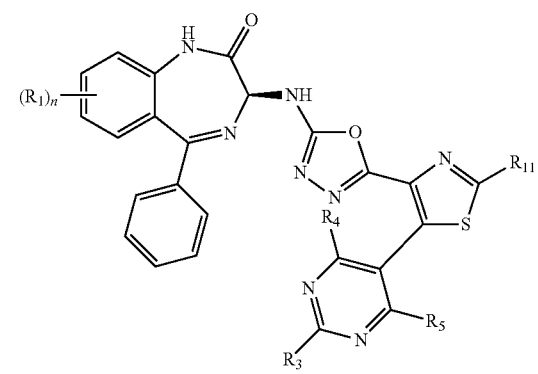
(IIIb-6)
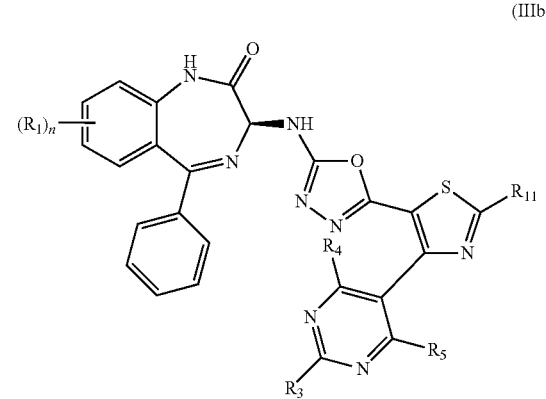
wherein $R_1$, $R_3$, $R_4$, $R_5$, n, $R_{11}$, $R_{12}$, and $R_{13}$, are as previously defined.
In another embodiment of the invention is a compound represented by one of Formulae (IV-1)~(IV-6), or a pharmaceutically acceptable salt, ester or prodrug thereof:
(IV-1)
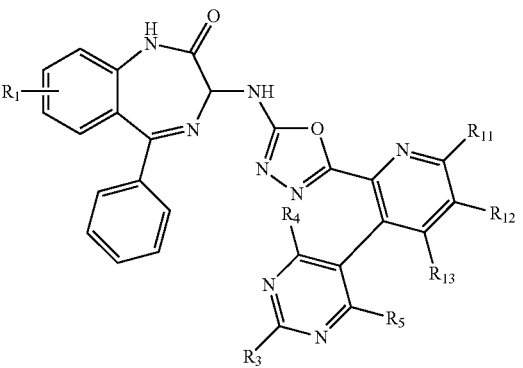
(IV-2)
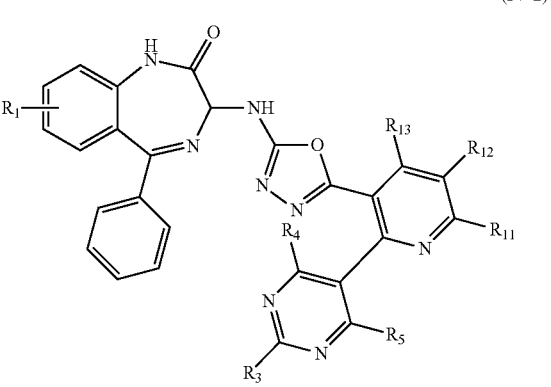
(IV-3)
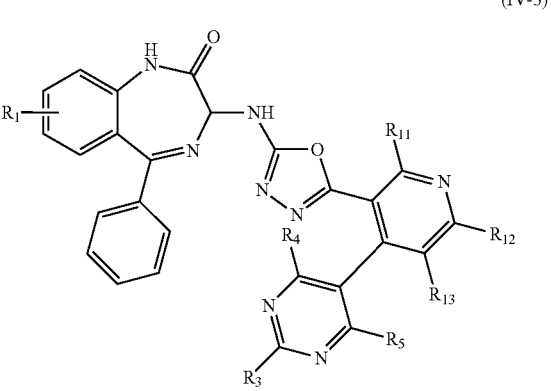
(IV-4)
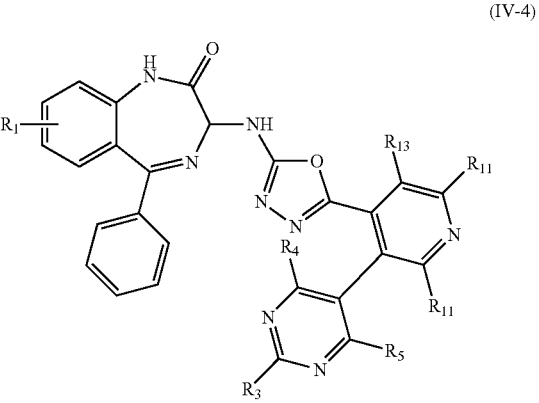

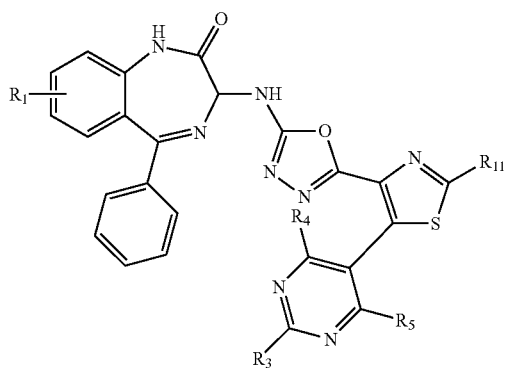
(IV-5)
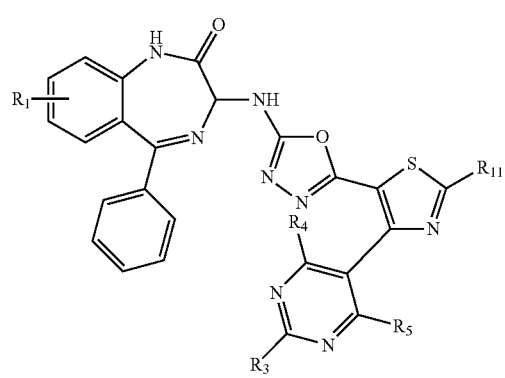
(IV-6)
wherein $R_1$, $R_3$, $R_4$, $R_5$, $R_{11}$, $R_{12}$, and $R_{13}$, are as previously defined.
In another embodiment of the invention is a compound represented by one of Formulae (IVb-1)~(IVb-6), or a pharmaceutically acceptable salt, ester or prodrug thereof:
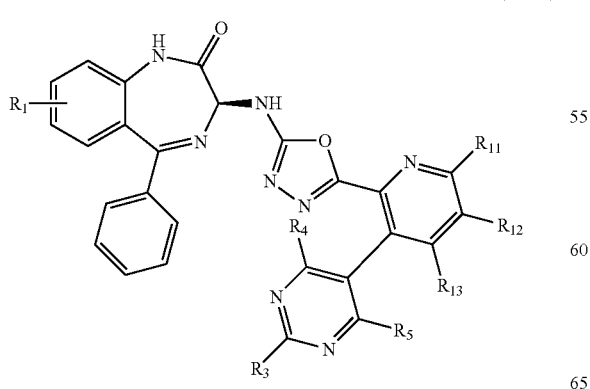
(IVb-1)
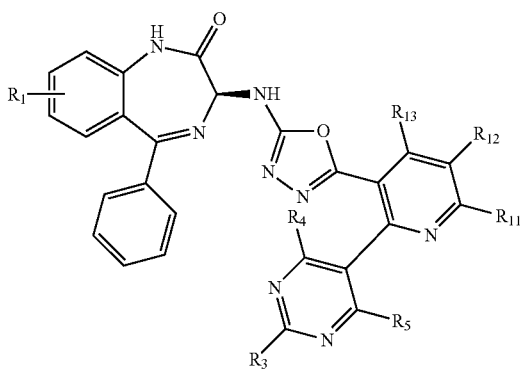
(IVb-2)
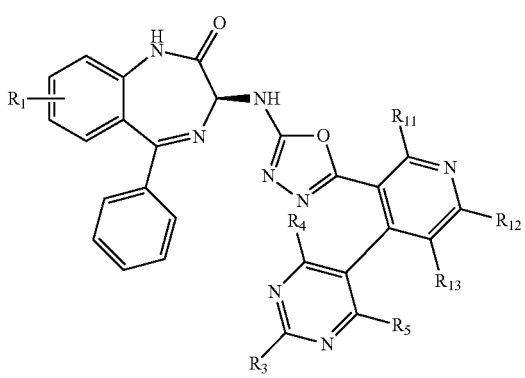
(IVb-3)
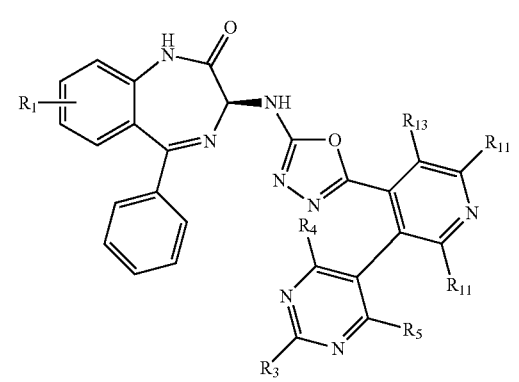
(IVb-4)
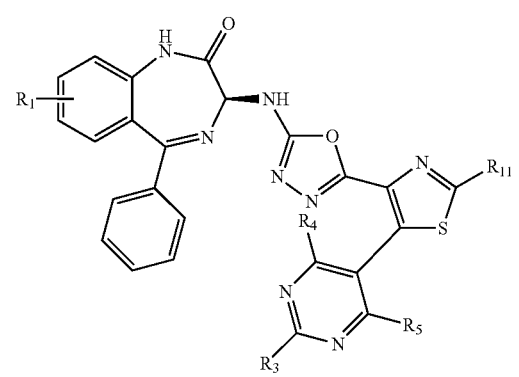
(IVb-5)

-continued
(IVb-6)
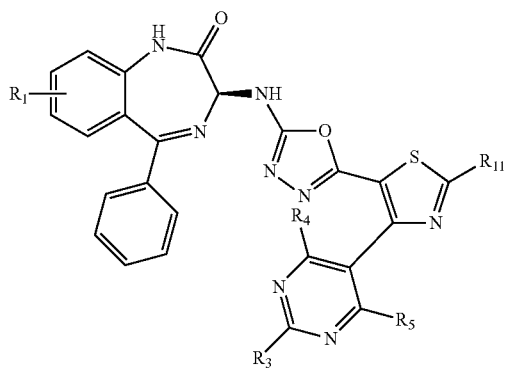
wherein R₁, R₃, R₄, R₅, R₁₁, R₁₂, and R₁₃, are as previously defined.
In one embodiment of the invention is a compound represented by one of Formulae (V-1)~(V-6), or a pharmaceutically acceptable salt, ester or prodrug thereof:
(V-1)
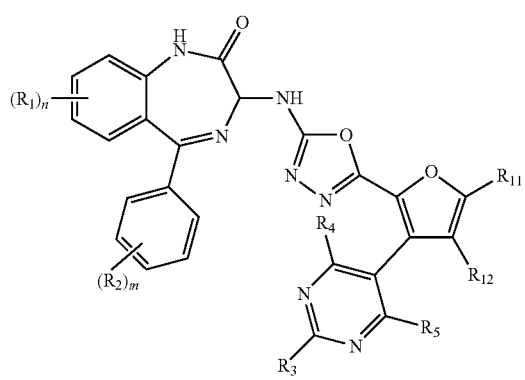
(V-2)
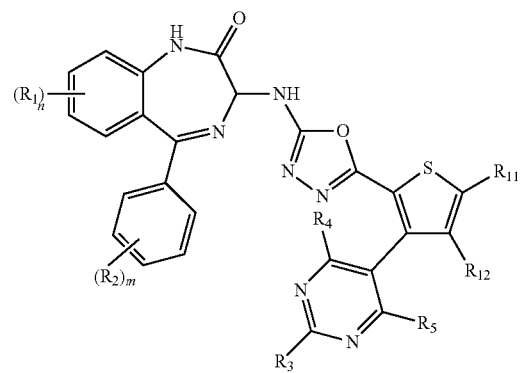
-continued
(V-3)
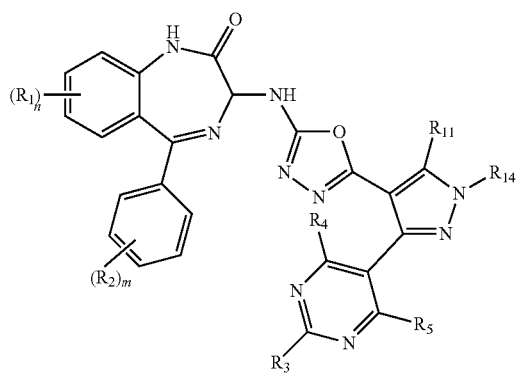
(V-4)
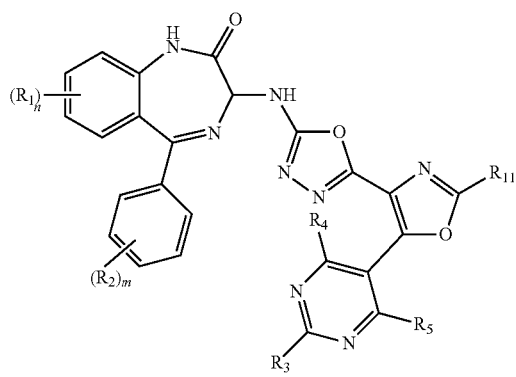
(V-5)
(V-6)
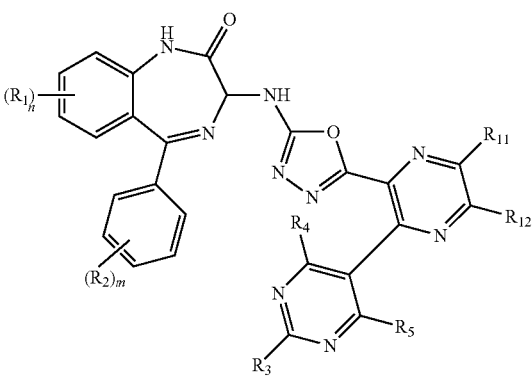
wherein R₁, R₂, R₃, R₄, R₅, n, m, R₁₁, R₁₂, and R₁₄, are as previously defined.

In one embodiment of the invention is a compound represented by one of Formulae (Vb-1)~(Vb-6), or a pharmaceutically acceptable salt, ester or prodrug thereof:

(Vb-1)
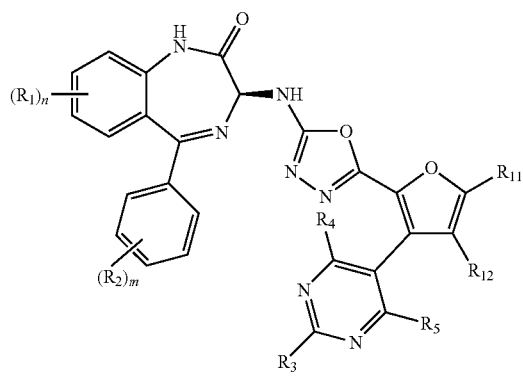

(Vb-2)
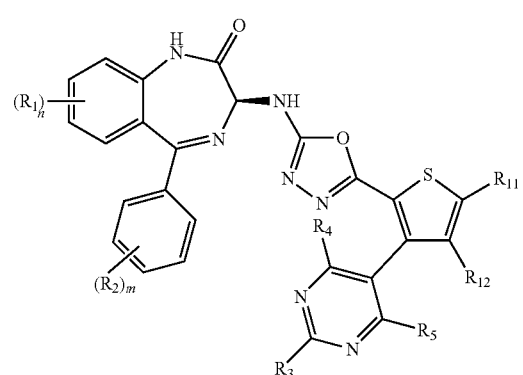

(Vb-3)
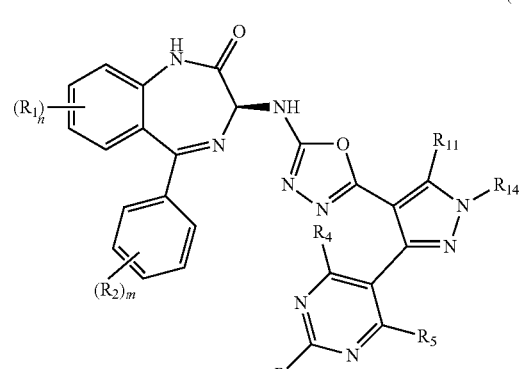

(Vb-4)
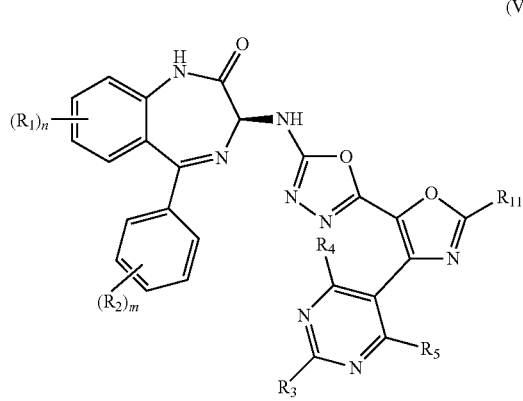

(Vb-5)
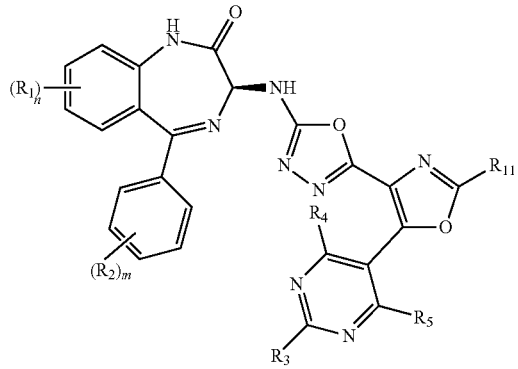

(Vb-6)
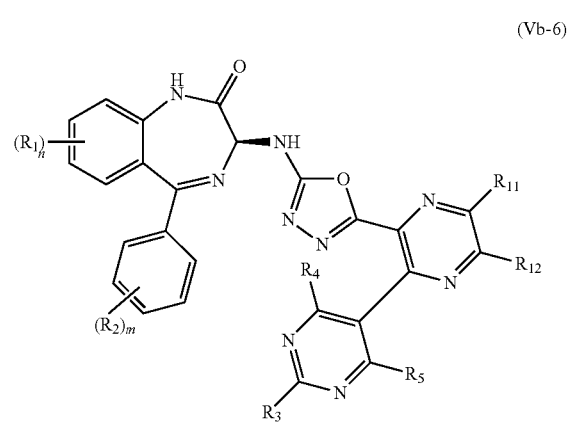

wherein $R_1$, $R_2$, $R_3$, $R_4$, $R_5$, n, m, $R_{11}$, $R_{12}$, and $R_{14}$, are as previously defined.

In one embodiment of the invention is a compound represented by one of Formulae (VI-1)~(VI-6), or a pharmaceutically acceptable salt, ester or prodrug thereof:

(VI-1)
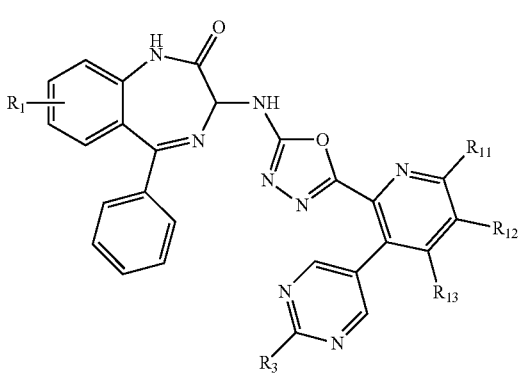

(VI-2)
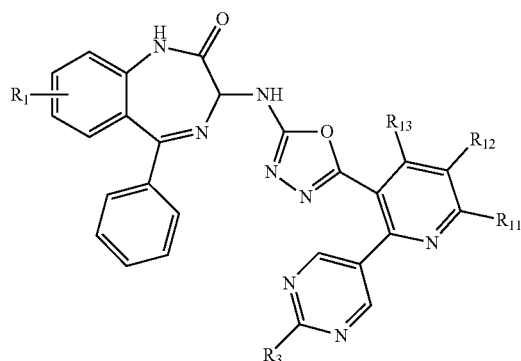
(VI-3)
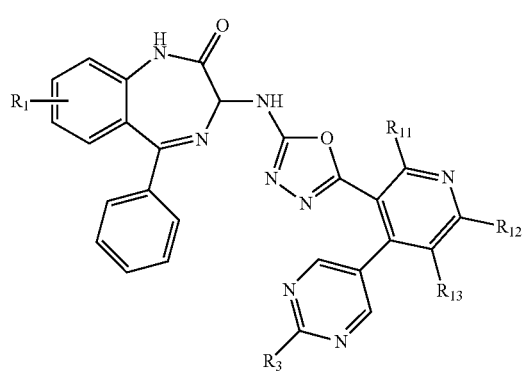
(VI-4)
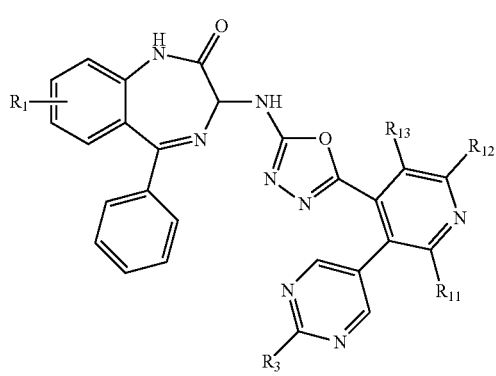
(VI-5)
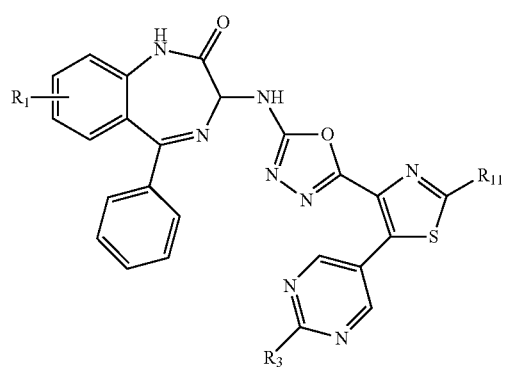
(VI-6)
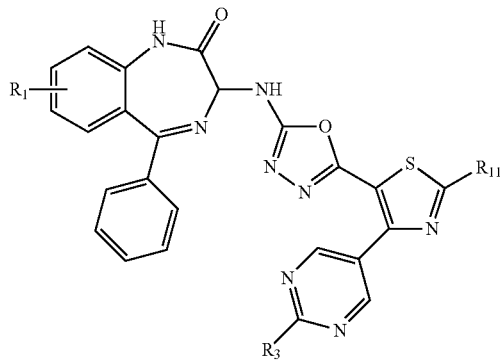
wherein $R_1$, $R_3$, $R_{11}$, $R_{12}$, and $R_{13}$, are as previously defined.
In one embodiment of the invention is a compound represented by one of Formulae (VIb-1)~(VIb-6), or a pharmaceutically acceptable salt, ester or prodrug thereof:
(VIb-1)
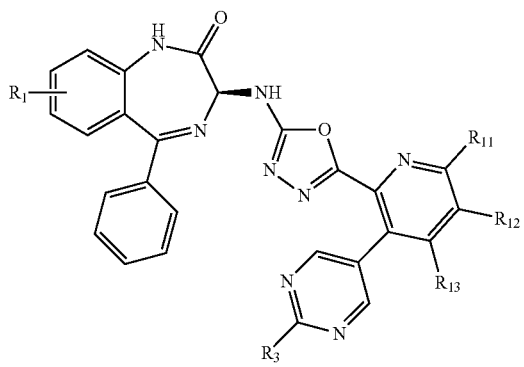
(VIb-2)
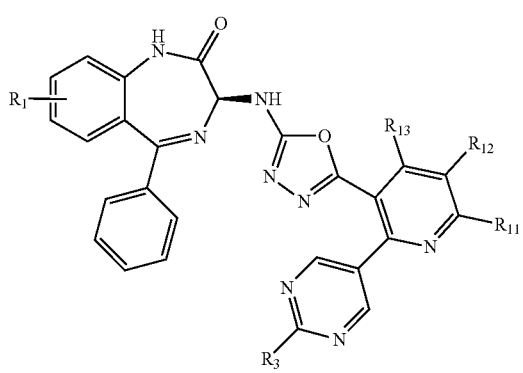

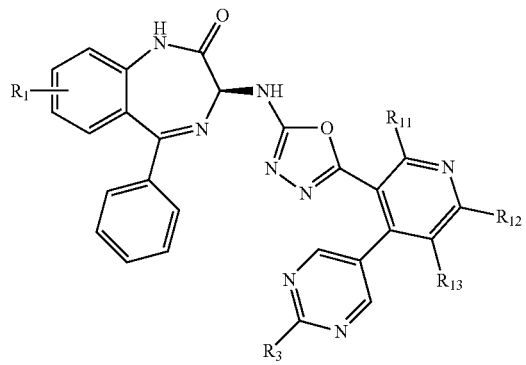
(VIb-3)
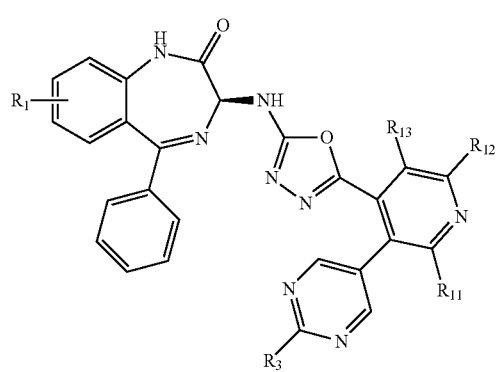
(VIb-4)
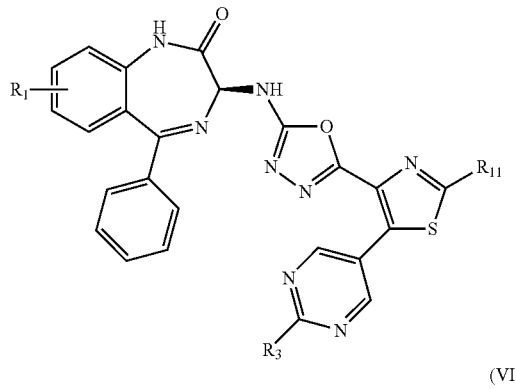
(VIb-5)
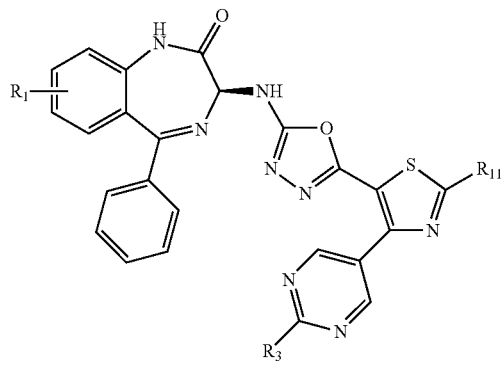
(VIb-6)
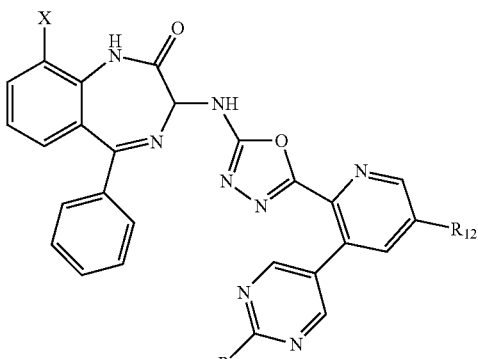
(VII-1)
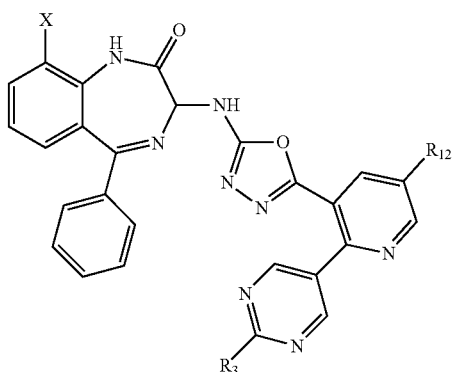
(VII-2)
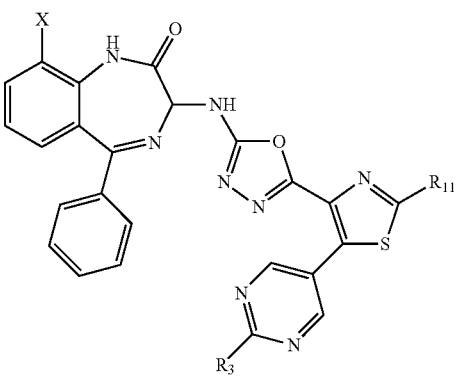
(VII-3)
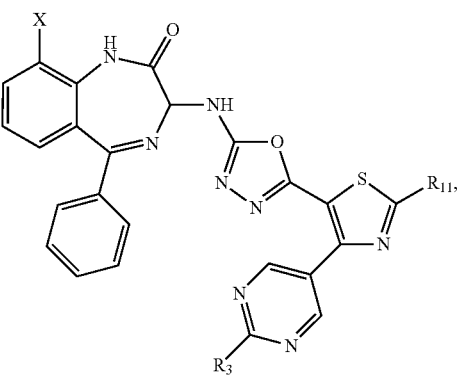
(VII-4)
wherein $R_1$, $R_3$, $R_{11}$, $R_{12}$, and $R_{13}$, are as previously defined.
In another embodiment of the invention is a compound represented by one of Formulae (VII-1)~(VII-4), or a pharmaceutically acceptable salt, ester or prodrug thereof:
wherein X is H or $R_1$, $R_3$, $R_{11}$, and $R_{12}$ are as previously defined.

In another embodiment of the invention is a compound represented by one of Formulae (VIIb-1)~(VIIb-4), or a pharmaceutically acceptable salt, ester or prodrug thereof:

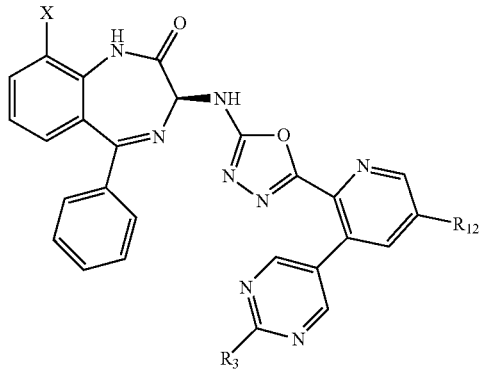

(VIIb-1)

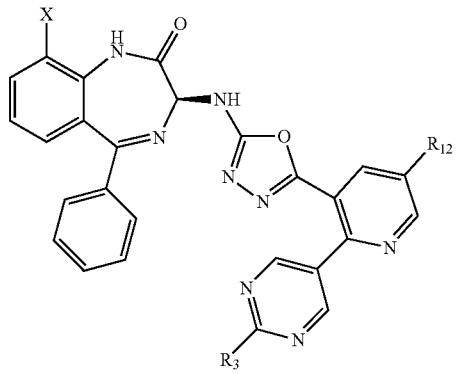

(VIIb-2)

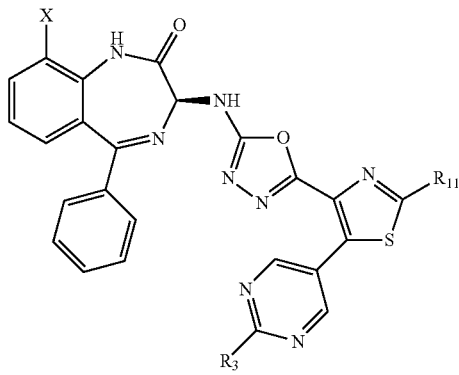

(VIIb-3)

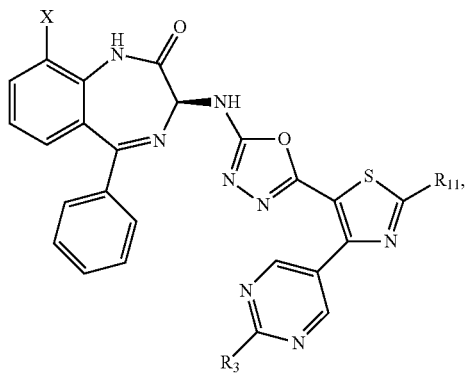

(VIIb-4)

wherein X, $R_3$, $R_{11}$, and $R_{12}$ are as previously defined.

In particular embodiments, the invention provides compounds of Formula (VII-1) and Formula (VII-2), and pharmaceutically acceptable salts, esters and prodrugs thereof, wherein X, $R_3$, and $R_{12}$ are delineated for each compound in Table 1.

TABLE 1

| Entry | X | $R_3$ | $R_{12}$ |
|---|---|---|---|
| 1-1 | H | Methyl | Methyl |
| 1-2 | H | Methyl | Ethyl |
| 1-3 | H | Methyl | Isopropyl |
| 1-4 | H | Methyl | Propyl |
| 1-5 | H | Methyl | Vinyl |
| 1-6 | H | Methyl | Allyl |
| 1-7 | H | Methyl | $CF_3$ |
| 1-8 | H | Methyl | $CHF_2$ |
| 1-9 | H | Methyl | CN |
| 1-10 | H | Methyl | ![cyclopropylmethyl] |
| 1-11 | H | Methyl | ![methylcyclopropyl] |
| 1-12 | H | Methyl | ![CF3-cyclopropyl] |
| 1-13 | H | Methyl | ![cyclopropylethyl] |
| 1-14 | H | Methyl | ![cyclobutyl] |
| 1-15 | H | Methyl | ![cyclopentyl] |
| 1-16 | H | Methyl | ![morpholinyl] |
| 1-17 | H | Ethyl | Methyl |
| 1-18 | H | Ethyl | Ethyl |
| 1-19 | H | Ethyl | Isopropyl |
| 1-20 | H | Ethyl | Propyl |
| 1-21 | H | Ethyl | Vinyl |
| 1-22 | H | Ethyl | Allyl |
| 1-23 | H | Ethyl | $CF_3$ |
| 1-24 | H | Ethyl | $CHF_2$ |
| 1-25 | H | Ethyl | CN |
| 1-26 | H | Ethyl | ![cyclopropyl] |

TABLE 1-continued

| Entry | X | R₃ | R₁₂ |
|---|---|---|---|
| 1-27 | H | Ethyl | (1,1-dimethylcyclopropyl) |
| 1-28 | H | Ethyl | (1-CF₃-cyclopropyl) |
| 1-29 | H | Ethyl | (cyclopropylmethyl) |
| 1-30 | H | Ethyl | (cyclobutyl) |
| 1-31 | H | Ethyl | (cyclopentyl) |
| 1-32 | H | Ethyl | (morpholinyl) |
| 1-33 | H | (cyclopropyl) | Methyl |
| 1-34 | H | (cyclopropyl) | Ethyl |
| 1-35 | H | (cyclopropyl) | Isopropyl |
| 1-36 | H | (cyclopropyl) | Propyl |
| 1-37 | H | (cyclopropyl) | Vinyl |
| 1-38 | H | (cyclopropyl) | Allyl |
| 1-39 | H | (cyclopropyl) | CF₃ |
| 1-40 | H | (cyclopropyl) | CHF₂ |
| 1-41 | H | (cyclopropyl) | CN |
| 1-42 | H | (cyclopropyl) | (cyclopropyl) |
| 1-43 | H | (cyclopropyl) | (1,1-dimethylcyclopropyl) |
| 1-44 | H | (cyclopropyl) | (1-CF₃-cyclopropyl) |
| 1-45 | H | (cyclopropyl) | (cyclopropylmethyl) |
| 1-46 | H | (cyclopropyl) | (cyclobutyl) |
| 1-47 | H | (cyclopropyl) | (cyclopentyl) |
| 1-48 | H | (cyclopropyl) | (morpholinyl) |
| 1-49 | F | Methyl | Methyl |
| 1-50 | F | Methyl | Ethyl |
| 1-51 | F | Methyl | Isopropyl |
| 1-52 | F | Methyl | Propyl |
| 1-53 | F | Methyl | Vinyl |
| 1-54 | F | Methyl | Allyl |
| 1-55 | F | Methyl | CF₃ |
| 1-56 | F | Methyl | CHF₂ |
| 1-57 | F | Methyl | CN |
| 1-58 | F | Methyl | 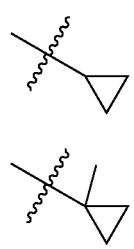 |
| 1-59 | F | Methyl | 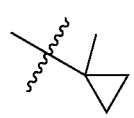 |

TABLE 1-continued

| Entry | X | R₃ | R₁₂ |
|---|---|---|---|
| 1-60 | F | Methyl | cyclopropyl-CF₃ |
| 1-61 | F | Methyl | CH₂-cyclopropyl |
| 1-62 | F | Methyl | cyclobutyl |
| 1-63 | F | Methyl | cyclopentyl |
| 1-64 | F | Methyl | morpholino |
| 1-65 | F | Ethyl | Methyl |
| 1-66 | F | Ethyl | Ethyl |
| 1-67 | F | Ethyl | Isopropyl |
| 1-68 | F | Ethyl | Propyl |
| 1-69 | F | Ethyl | Vinyl |
| 1-70 | F | Ethyl | Allyl |
| 1-71 | F | Ethyl | CF₃ |
| 1-72 | F | Ethyl | CHF₂ |
| 1-73 | F | Ethyl | CN |
| 1-74 | F | Ethyl | cyclopropyl |
| 1-75 | F | Ethyl | methylcyclopropyl |
| 1-76 | F | Ethyl | cyclopropyl-CF₃ |
| 1-77 | F | Ethyl | CH₂-cyclopropyl |
| 1-78 | F | Ethyl | cyclobutyl |
| 1-79 | F | Ethyl | cyclopentyl |

TABLE 1-continued

| Entry | X | R₃ | R₁₂ |
|---|---|---|---|
| 1-80 | F | Ethyl | morpholino |
| 1-81 | F | cyclopropyl | Methyl |
| 1-82 | F | cyclopropyl | Ethyl |
| 1-83 | F | cyclopropyl | Isopropyl |
| 1-84 | F | cyclopropyl | Propyl |
| 1-85 | F | cyclopropyl | Vinyl |
| 1-86 | F | cyclopropyl | Allyl |
| 1-87 | F | cyclopropyl | CF₃ |
| 1-88 | F | cyclopropyl | CHF₂ |
| 1-89 | F | cyclopropyl | CN |
| 1-90 | F | cyclopropyl | cyclopropyl |
| 1-91 | F | cyclopropyl | methylcyclopropyl |

TABLE 1-continued

| Entry | X | R₃ | R₁₂ |
|---|---|---|---|
| 1-92 | F | cyclopropyl | cyclopropyl-CF₃ |
| 1-93 | F | cyclopropyl | CH₂-cyclopropyl |
| 1-94 | F | cyclopropyl | cyclobutyl |
| 1-95 | F | cyclopropyl | cyclopentyl |
| 1-96 | F | cyclopropyl | morpholino |

In particular embodiments, the invention provides compounds of Formula (VII-3) and Formula (VII-4), and pharmaceutically acceptable salts, esters and prodrugs thereof, where X, $R_3$, and $R_{11}$ are delineated for each compound in Table 2.

TABLE 2

| Entry | X | R₃ | R₁₁ |
|---|---|---|---|
| 2-1 | H | Methyl | Methyl |
| 2-2 | H | Methyl | Ethyl |
| 2-3 | H | Methyl | Isopropyl |
| 2-4 | H | Methyl | Butyl |
| 2-5 | H | Methyl | t-Butyl |
| 2-6 | H | Methyl | Propyl |
| 2-7 | H | Methyl | Benzyl |
| 2-8 | H | Methyl | Vinyl |
| 2-9 | H | Methyl | Allyl |
| 2-10 | H | Methyl | CF₃ |
| 2-11 | H | Methyl | cyclopropyl |
| 2-12 | H | Methyl | methylcyclopropyl |
| 2-13 | H | Methyl | cyclopropyl-CF₃ |
| 2-14 | H | Methyl | CH₂-cyclopropyl |
| 2-15 | H | Methyl | cyclobutyl |
| 2-16 | H | Methyl | cyclopentyl |
| 2-17 | H | Ethyl | Methyl |
| 2-18 | H | Ethyl | Ethyl |
| 2-19 | H | Ethyl | Isopropyl |
| 2-20 | H | Ethyl | Butyl |
| 2-21 | H | Ethyl | t-Butyl |
| 2-22 | H | Ethyl | Propyl |
| 2-23 | H | Ethyl | Benzyl |
| 2-24 | H | Ethyl | Vinyl |
| 2-25 | H | Ethyl | Allyl |
| 2-26 | H | Ethyl | CF₃ |
| 2-27 | H | Ethyl | cyclopropyl |
| 2-28 | H | Ethyl | methylcyclopropyl |
| 2-29 | H | Ethyl | cyclopropyl-CF₃ |
| 2-30 | H | Ethyl | CH₂-cyclopropyl |
| 2-31 | H | Ethyl | cyclobutyl |
| 2-32 | H | Ethyl | cyclopentyl |
| 2-33 | H | cyclopropyl | Methyl |
| 2-34 | H | cyclopropyl | Ethyl |
| 2-35 | H | cyclopropyl | Isopropyl |

TABLE 2-continued

| Entry | X | R$_3$ | R$_{11}$ |
|---|---|---|---|
| 2-36 | H | cyclopropyl | Butyl |
| 2-37 | H | cyclopropyl | t-Butyl |
| 2-38 | H | cyclopropyl | Propyl |
| 2-39 | H | cyclopropyl | Benzyl |
| 2-40 | H | cyclopropyl | Vinyl |
| 2-41 | H | cyclopropyl | Allyl |
| 2-42 | H | cyclopropyl | CF$_3$ |
| 2-43 | H | cyclopropyl | cyclopropyl |
| 2-44 | H | cyclopropyl | methylcyclopropyl |
| 2-45 | H | cyclopropyl | CF$_3$-cyclopropyl |
| 2-46 | H | cyclopropyl | cyclopropylmethyl |
| 2-47 | H | cyclopropyl | cyclobutyl |
| 2-48 | H | cyclopropyl | cyclopentyl |

TABLE 2-continued

| Entry | X | R$_3$ | R$_{11}$ |
|---|---|---|---|
| 2-49 | F | Methyl | Methyl |
| 2-50 | F | Methyl | Ethyl |
| 2-51 | F | Methyl | Isopropyl |
| 2-52 | F | Methyl | Butyl |
| 2-53 | F | Methyl | t-Butyl |
| 2-54 | F | Methyl | Propyl |
| 2-55 | F | Methyl | Benzyl |
| 2-56 | F | Methyl | Vinyl |
| 2-57 | F | Methyl | Allyl |
| 2-58 | F | Methyl | CF$_3$ |
| 2-59 | F | Methyl | cyclopropyl |
| 2-60 | F | Methyl | methylcyclopropyl |
| 2-61 | F | Methyl | CF$_3$-cyclopropyl |
| 2-62 | F | Methyl | cyclopropylmethyl |
| 2-63 | F | Methyl | cyclobutyl |
| 2-64 | F | Methyl | cyclopentyl |
| 2-65 | F | Ethyl | Methyl |
| 2-66 | F | Ethyl | Ethyl |
| 2-67 | F | Ethyl | Isopropyl |
| 2-68 | F | Ethyl | Butyl |
| 2-69 | F | Ethyl | t-Butyl |
| 2-70 | F | Ethyl | Propyl |
| 2-71 | F | Ethyl | Benzyl |
| 2-77 | F | Ethyl | Vinyl |
| 2-73 | F | Ethyl | Allyl |
| 2-74 | F | Ethyl | CF$_3$ |
| 2-75 | F | Ethyl | cyclopropyl |
| 2-76 | F | Ethyl | methylcyclopropyl |
| 2-77 | F | Ethyl | CF$_3$-cyclopropyl |

TABLE 2-continued

| Entry | X | R₃ | R₁₁ |
|---|---|---|---|
| 2-78 | F | Ethyl | (cyclopropylmethyl) |
| 2-79 | F | Ethyl | (cyclobutyl) |
| 2-80 | F | Ethyl | (cyclopentyl) |
| 2-81 | F | (cyclopropyl) | Methyl |
| 2-82 | F | (cyclopropyl) | Ethyl |
| 2-83 | F | (cyclopropyl) | Isopropyl |
| 2-84 | F | (cyclopropyl) | Butyl |
| 2-85 | F | (cyclopropyl) | t-Butyl |
| 2-86 | F | (cyclopropyl) | Propyl |
| 2-87 | F | (cyclopropyl) | Benzyl |
| 2-88 | F | (cyclopropyl) | Vinyl |
| 2-89 | F | (cyclopropyl) | Allyl |
| 2-90 | F | (cyclopropyl) | CF₃ |
| 2-91 | F | (cyclopropyl) | (cyclopropyl) |
| 2-92 | F | (1-methylcyclopropyl) | (1-methylcyclopropyl) |
| 2-93 | F | (cyclopropyl) | (1-CF₃-cyclopropyl) |
| 2-94 | F | (cyclopropyl) | (cyclopropylmethyl) |
| 2-95 | F | (cyclopropyl) | (cyclobutyl) |
| 2-96 | F | (cyclopropyl) | (cyclopentyl) |

In another embodiment of the invention is a compound represented by one of Formulae (VIII-1)~(VIII-4), or a pharmaceutically acceptable salt, ester or prodrug thereof:

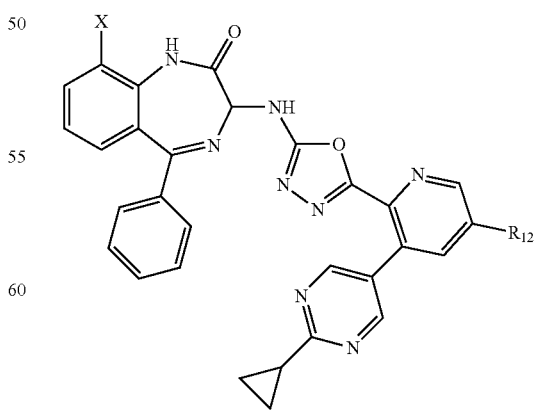

(VIII-1)

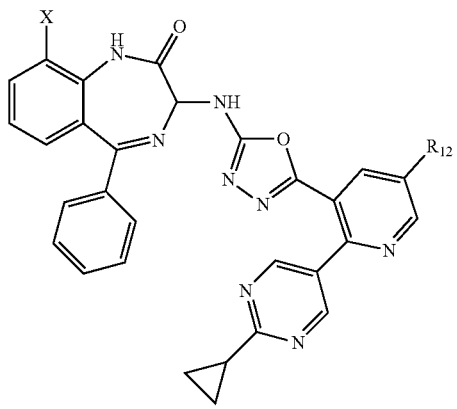
(VIII-2)
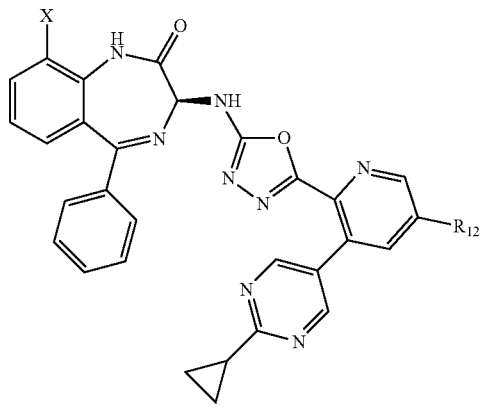
(VIIIb-1)
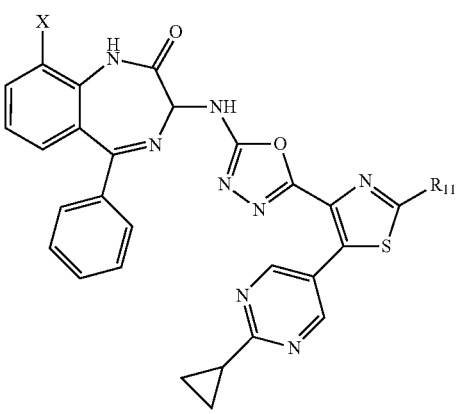
(VIII-3)
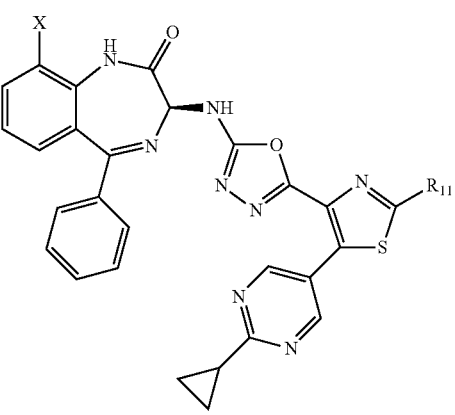
(VIIIb-2)
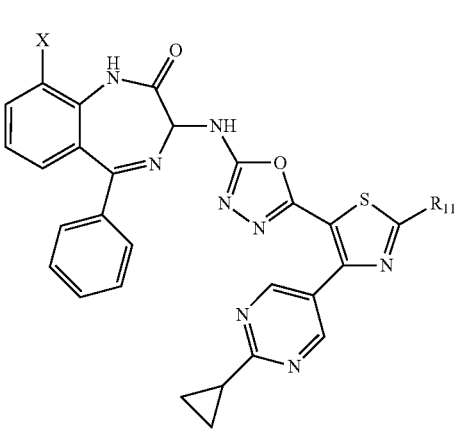
(VIII-4)
(VIIIb-3)
wherein X is H or $R_1$; $R_{11}$ and $R_{12}$ are as previously defined.
In another embodiment of the invention is a compound represented by one of Formulae (VIIb-1)~(VIIb-4), or a pharmaceutically acceptable salt, ester or prodrug thereof:

-continued (VIIIb-4)

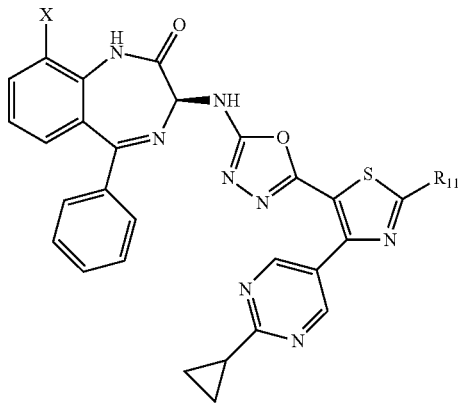

wherein X, $R_{11}$, and $R_{12}$ are as previously defined.

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule. For example, in Formula (I) when n is 2, each of the two $R_1$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection is subjects. The method comprises administering a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of Formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of Formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the Formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluant or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon radicals. Preferred alkyl radicals include $C_1$-$C_6$ alkyl and $C_1$-$C_8$ alkyl radicals. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl groups include, but are not limited to, methyl, ethyl, propyl, isopropyl, n-butyl, tert-butyl, neopentyl, n-hexyl, heptyl, and octyl radicals.

The term "alkenyl" as used herein, refers to straight- or branched-chain hydrocarbon radicals having at least one carbon-carbon double bond by the removal of a single hydrogen atom. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl" as used herein, refers to straight- or branched-chain hydrocarbon radicals having at least one carbon-carbon triple bond by the removal of a single hydrogen atom. Preferred alkynyl radicals include $C_2$-$C_6$ alkynyl and $C_2$-$C_8$ alkynyl radicals. Representative alkynyl radicals include, but are not limited to, for example, ethynyl, 1-propynyl, 1-butynyl, heptynyl, octynyl and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure, the carbocycle group can be attached to the two other elements through any two substitutable ring atoms. A $C_4$-$C_6$ carbocycle has 4-6 ring atoms.

The term "cycloalkyl", as used herein, refers to a monocyclic or polycyclic saturated carbocyclic ring compound, and the carbon atoms may be optionally oxo-substituted. A polycyclic cycloalkenyl can comprise fused rings. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "cycloalkenyl", as used herein, refers to monocyclic or polycyclic carbocyclic ring compound having at least one carbon-carbon double bond and the carbon atoms may be optionally oxo-substituted. A polycyclic cycloalkenyl can comprise fused rings, covalently attached rings or a combination thereof. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "heterocycloalkyl" and "heterocyclic" can be used interchangeably and refer to a non-aromatic 3-, 4-, 5-, 6-, 7- or 8- or 9-12 membered ring or a bi- or tri-cyclic group fused or bridged or spiro system, where: (i) each ring contains between one and three heteroatoms independently selected from oxygen, sulfur and nitrogen, (ii) each 5-membered ring has 0 to 1 double bonds and each 6-, 7-, 8-, or 9-12 membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, 8-azabicyclo[3.2.1]octyl, 5-azaspiro[2.5]octyl, 1-oxa-7-azaspiro[4.4]nonanyl, and tetrahydrofuryl. Such heterocyclic groups may be further substituted to give substituted heterocyclic. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, indenyl and the like. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. A polycyclic heteroaryl can comprise fused rings, covalently attached rings or a combination thereof.

In accordance with the invention, aromatic groups can be substituted or unsubstituted.

The term "arylalkyl," as used herein, refers to functional group wherein an alkylene chain is attached to an aryl group. Examples include, but are not limited to, benzyl, phenethyl and the like. The term "substituted arylalkyl" means an arylalkyl functional group in which the aryl group is substituted. Similarly, the term "heteroarylalkyl" means a functional group wherein an alkylene chain is attached to a heteroaryl group. Examples include, but are not limited to, pyridinylmethyl, pyrimidinylethyl and the like. The term "substituted heteroarylalkyl" means a heteroarylalkyl functional group in which the heteroaryl group is substituted.

The term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "halo" or halogen" alone or as part of another substituent, as used herein, refers to a fluorine, chlorine, bromine, or iodine atom.

The term "hydrogen" includes hydrogen and deuterium. In addition, the recitation of an atom includes other isotopes of that atom so long as the resulting compound is pharmaceutically acceptable.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_2$-cycloalkyl, —$CO_2$-aryl, $CO_2$-heteroaryl, $CO_2$-heterocyloalkyl, —$OCONH_2$, —OCONH—$C_3$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_{12}$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthio-methyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted when possible with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group, such as a substituted methyl group, is substituted with one or more halogen atoms, more preferably one or more fluorine or chlorine atoms.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethyl silyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —$C(O)CH_3$), benzoyl (Bz or —C(O)$C_6H_5$), and trimethylsilyl (TMS or —$Si(CH_3)_3$), and the like.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, including the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BzCl for benzoyl chloride;
CDI for 1,1'-carbonyldiimidazole;
DCM for dichloromethane;
DIAD for diisopropyl azodicarboxylate;
DIPEA for diisopropyl ethylamine;
DMAP for 4-(dimethylamino)pyridine;
DMEM for Dulbecco's Modified Eagles Media;
DMF for N,N-dimethyl formamide;
DMSO for dimethylsulfoxide;
EDCI or EDC for 1-(3-diethylaminopropyl)-3-ethylcarbodiimide hydrochloride;
EtOAc or EA for ethyl acetate;
EtOH for ethyl alcohol;
HATU for 0 (7-Azabenzotriazole-1-yl)-N,N,N',N'-tetramethyluronium hexafluorophosphate;
HCl for hydrochloric acid;
KHMDS is potassium bis(trimethylsilyl) amide;
LDA for Lithium diisopropylamide;
MeCN for acetonitrile;
Ms for mesyl;
NMM for N-4-methylmorpholine;
PE for petroleum ether;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethylamine;
Tf$_2$O for trifluoromethanesulfonic anhydride;
TFA for trifluoroacetic acid;
THF for tetrahydrofuran;
TLC for thin layer chromatography;
TPP or PPh$_3$ for triphenylphosphine;
TsCl for p-Toluenesulfonyl chloride;
tBOC or Boc for tert-butyloxy carbonyl.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, compounds of formula 9 are prepared starting from compounds 1 and 2. Compound 1 is coupled to a protected carbazate 2 using an appropriate coupling reagent such as, but not limited to, EDCI with HOBt or HATU to afford compound 3, wherein $R_{11}$, $R_{12}$, and $R_{13}$ are as previously defined. Compound 3 is converted to the corresponding hydrazide 4, using the appropriate conditions. Hydrazide 4 is then reacted with 5, wherein m, n, $R_1$ and $R_2$ are as previously defined, to form semicarbazide 6. Compounds of formula 6 is reacted with TsCl to afford the oxadiazole of formula 7 bearing the Br. Compound 7 is reacted further with appropriate coupling partners selected from 8, but not limited to, boronic acids, boronic esters, organotin reagents, organozinc reagents, organomagnesium reagents, organo silicon reagents, wherein $R_3$, $R_4$ and $R_5$ are as previously defined, in combination with the appropriate Pd, Ni, or Cu catalyst to afford compounds of formula 9.

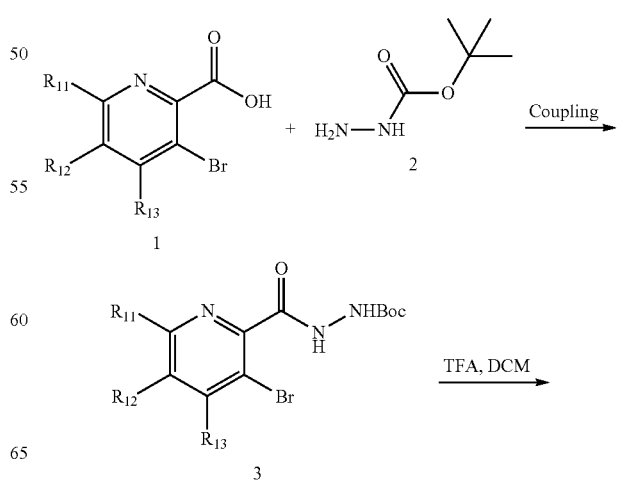

55
-continued

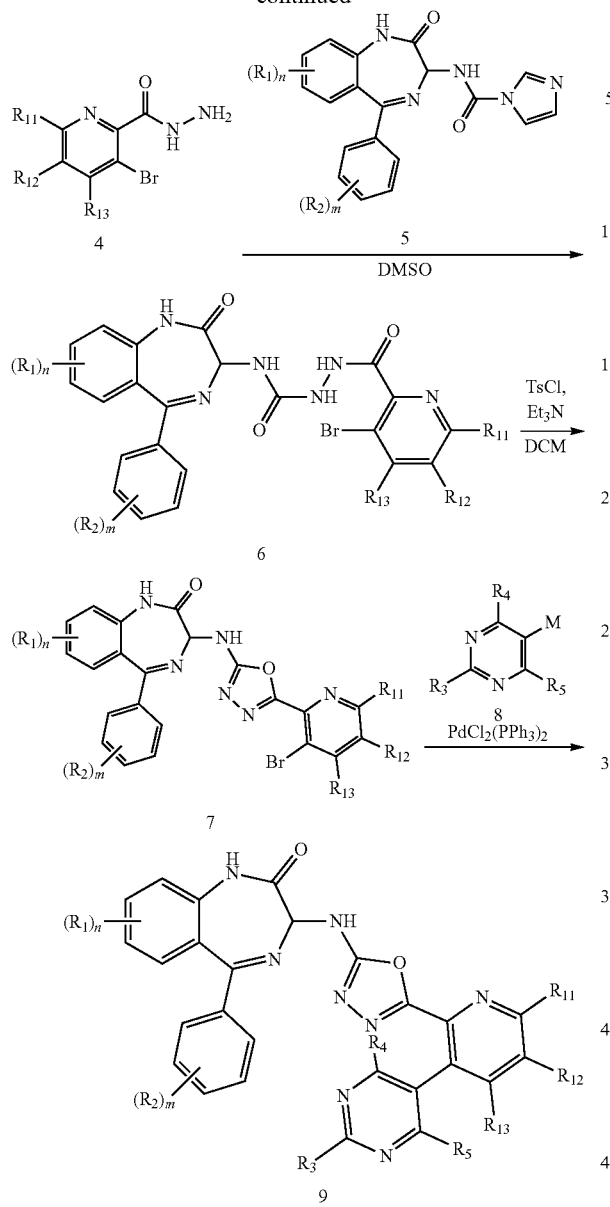

M = B(OH)₂, B(OR)₂, ZnAr, Sn(alkyl)₃, MgBr, Si(alkyl)₃

Scheme 2 illustrates alternative methods, wherein m, n, $R_1$, $R_2$, $R_3$, $R_4$, $R_5$, $R_{11}$, $R_{12}$ and $R_{13}$ are defined as previously described, to prepare compounds of formula (14). 2-Bromo pyridyl ester 10 is reacted with appropriate coupling partners selected from 8, but not limited to, boronic acids, boronic esters, organotin reagents, organozinc reagents, organomagnesium reagents, organo silicon reagents, in combination with the appropriate Pd, Ni, or Cu catalyst to afford compounds of formula 11. Compound 11 is then converted to hydrazide of formula 12. Compound 12 is then reacted with 5, to afford semicarbazide 13. Compounds of formula 13 can be further reacted with dehydrating reagents such as, but not limited to, tTsCl, POCl₃, diphenyl(2-pyridyl)phosphine dichloride to afford the oxadiazole of formula 14.

56

Scheme 2

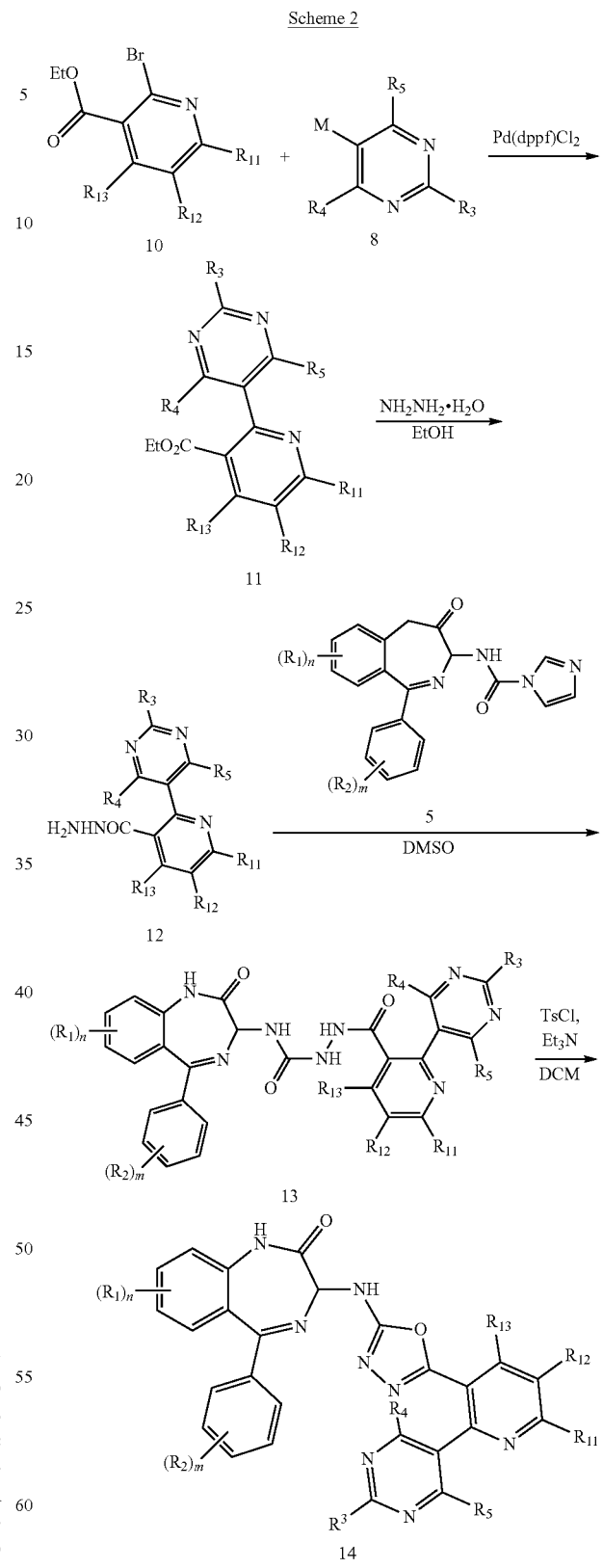

M = B(OH)₂, B(OR)₂, ZnAr, Sn(alkyl)₃, MgBr, Si(alkyl)₃

Scheme 3 illustrates alternative methods, wherein m, n, $R_1$, $R_2$, $R_3$, $R_4$, $R_5$, $R_{11}$, $R_{12}$ and $R_{13}$ are defined as previously described, to prepare compounds of formula (20). Compound 15 is reacted with appropriate coupling partners selected from 8, but not limited to, boronic acids, boronic esters, organotin reagents, organozinc reagents, organomagnesium reagents, organo silicon reagents, in combination with the appropriate Pd, Ni, or Cu catalyst to afford compounds of formula 16. Compound 16 is then converted to hydrazide of formula 17. Compound 17 is then reacted with 18, to afford semicarbazide 19. Compounds of formula 6 can be further reacted with tosyl chloride (TsCl) to afford the oxadiazole of formula 20.

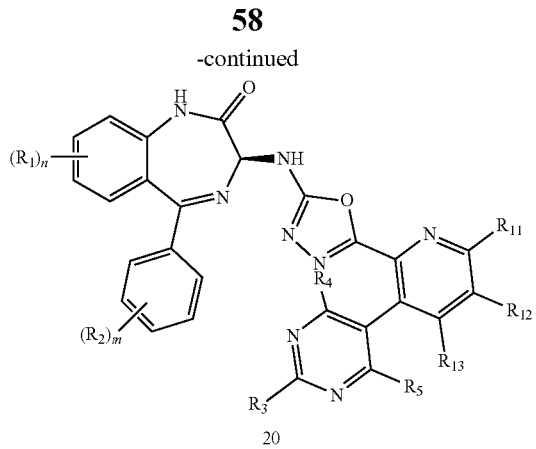

M = B(OH)$_2$, B(OR)$_2$, ZnAr, Sn(alkyl)$_3$, MgBr, Si(alkyl)$_3$

Scheme 4 illustrates methods, wherein m, n, R$_1$, R$_2$, R$_3$, R$_4$, and R$_5$ are defined as previously described, to prepare compounds of formula 28 and 29. Compound 21 is brominated to afford a compound of formula 22, wherein R$_{11}$ is methyl or trifluoromethyl group. Compound 22 is reacted with appropriate coupling partners selected from 8, but not limited to, boronic acids, boronic esters, organotin reagents, organozinc reagents, organomagnesium reagents, organo silicon reagents, in combination with the appropriate Pd, Ni, or Cu catalyst to afford compounds of formula 23, which can be converted to hydrazide of formula 24. Amine 25 is reacted with TCDI to generate the intermediate 26 that is reacted with hydrazide 24 to generate the racemic oxadiazole 27. Compound 27 is then separated by chiral method to afford compound 28 and 29, respectively.

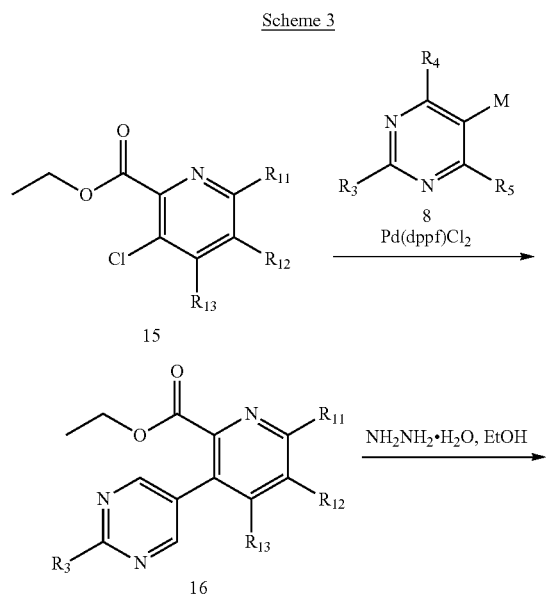

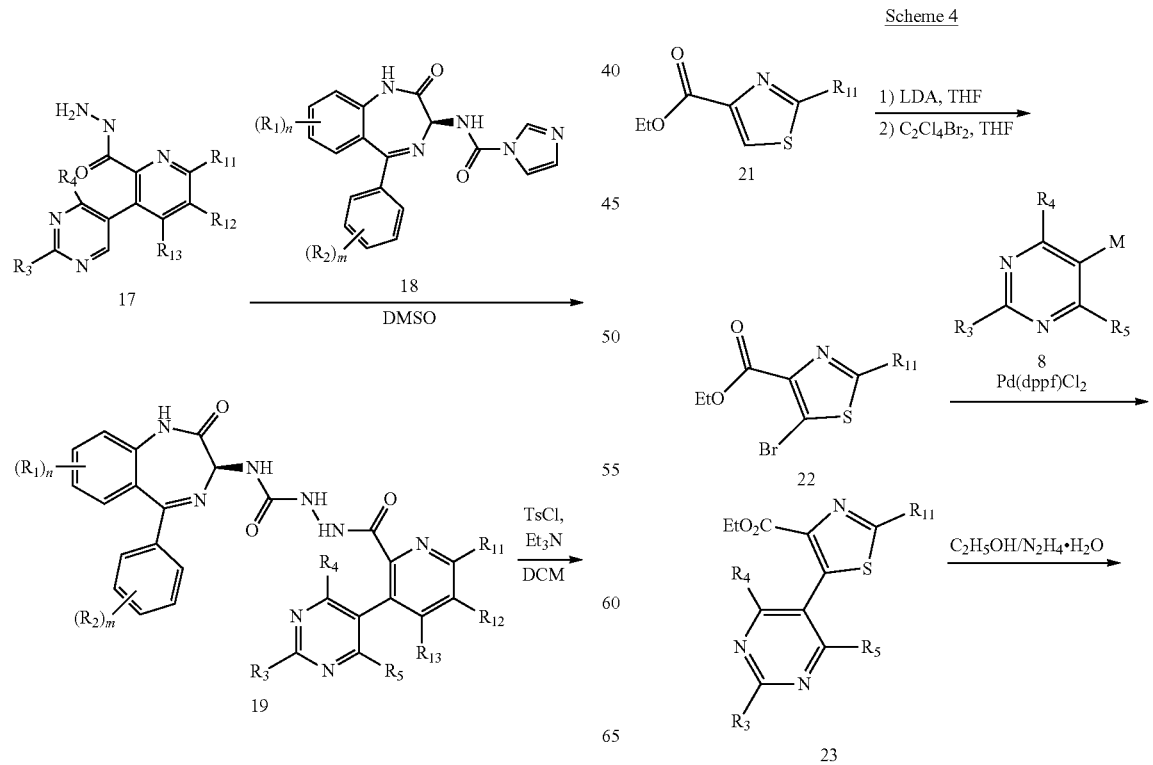

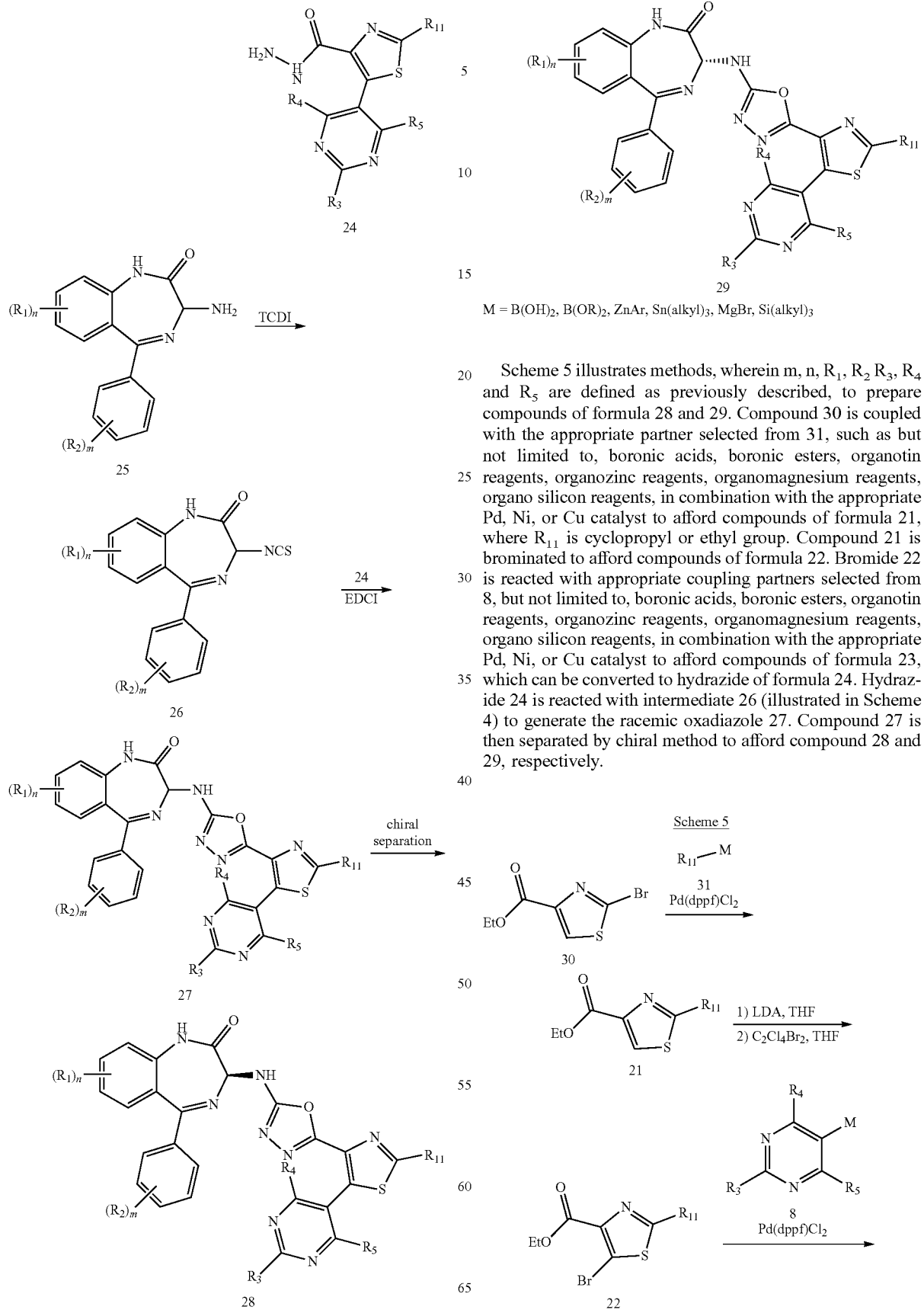

M = B(OH)$_2$, B(OR)$_2$, ZnAr, Sn(alkyl)$_3$, MgBr, Si(alkyl)$_3$

Scheme 5 illustrates methods, wherein m, n, R$_1$, R$_2$ R$_3$, R$_4$ and R$_5$ are defined as previously described, to prepare compounds of formula 28 and 29. Compound 30 is coupled with the appropriate partner selected from 31, such as but not limited to, boronic acids, boronic esters, organotin reagents, organozinc reagents, organomagnesium reagents, organo silicon reagents, in combination with the appropriate Pd, Ni, or Cu catalyst to afford compounds of formula 21, where R$_{11}$ is cyclopropyl or ethyl group. Compound 21 is brominated to afford compounds of formula 22. Bromide 22 is reacted with appropriate coupling partners selected from 8, but not limited to, boronic acids, boronic esters, organotin reagents, organozinc reagents, organomagnesium reagents, organo silicon reagents, in combination with the appropriate Pd, Ni, or Cu catalyst to afford compounds of formula 23, which can be converted to hydrazide of formula 24. Hydrazide 24 is reacted with intermediate 26 (illustrated in Scheme 4) to generate the racemic oxadiazole 27. Compound 27 is then separated by chiral method to afford compound 28 and 29, respectively.

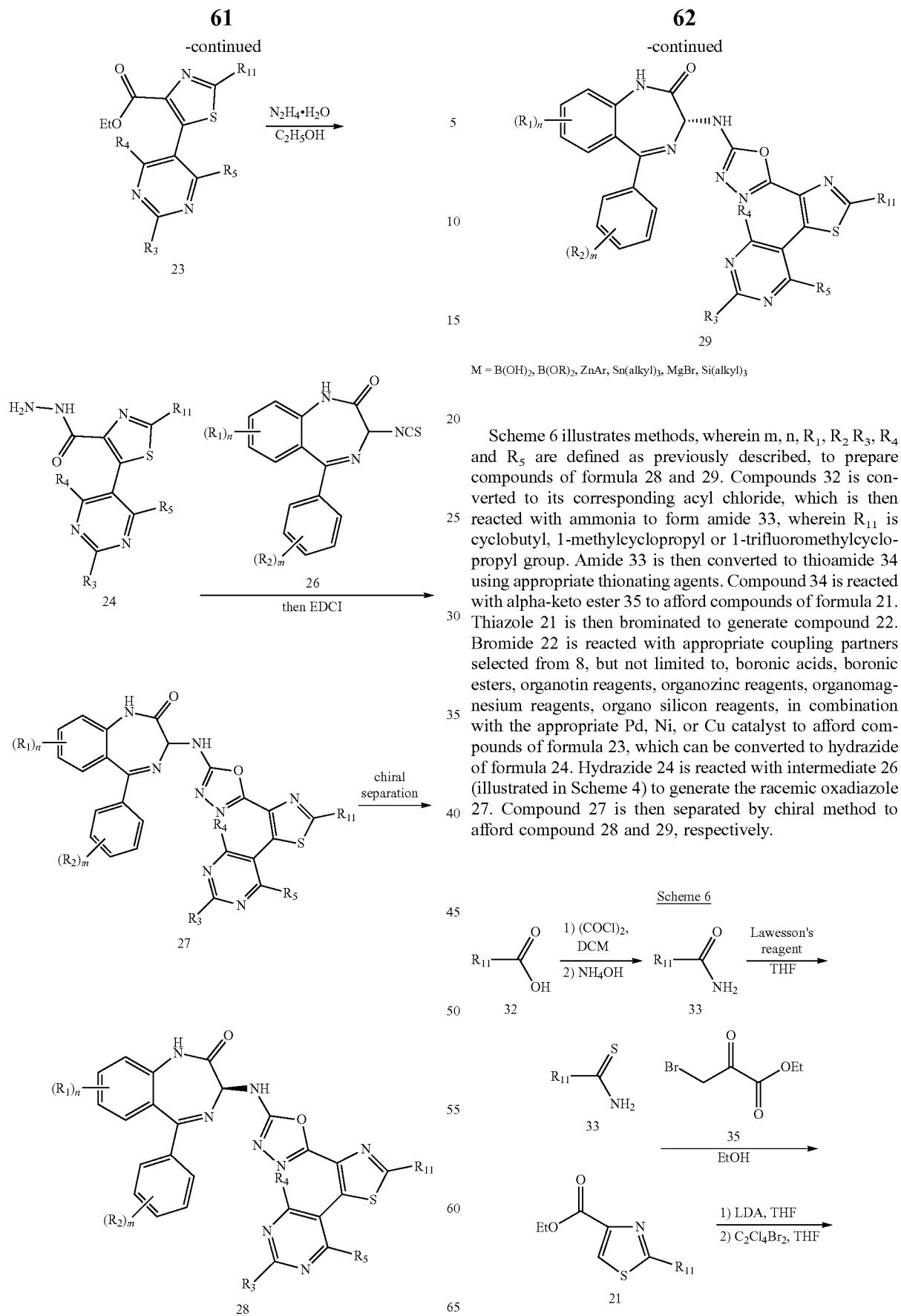

Scheme 6 illustrates methods, wherein m, n, $R_1$, $R_2$ $R_3$, $R_4$ and $R_5$ are defined as previously described, to prepare compounds of formula 28 and 29. Compounds 32 is converted to its corresponding acyl chloride, which is then reacted with ammonia to form amide 33, wherein $R_{11}$ is cyclobutyl, 1-methylcyclopropyl or 1-trifluoromethylcyclopropyl group. Amide 33 is then converted to thioamide 34 using appropriate thionating agents. Compound 34 is reacted with alpha-keto ester 35 to afford compounds of formula 21. Thiazole 21 is then brominated to generate compound 22. Bromide 22 is reacted with appropriate coupling partners selected from 8, but not limited to, boronic acids, boronic esters, organotin reagents, organozinc reagents, organomagnesium reagents, organo silicon reagents, in combination with the appropriate Pd, Ni, or Cu catalyst to afford compounds of formula 23, which can be converted to hydrazide of formula 24. Hydrazide 24 is reacted with intermediate 26 (illustrated in Scheme 4) to generate the racemic oxadiazole 27. Compound 27 is then separated by chiral method to afford compound 28 and 29, respectively.

-continued

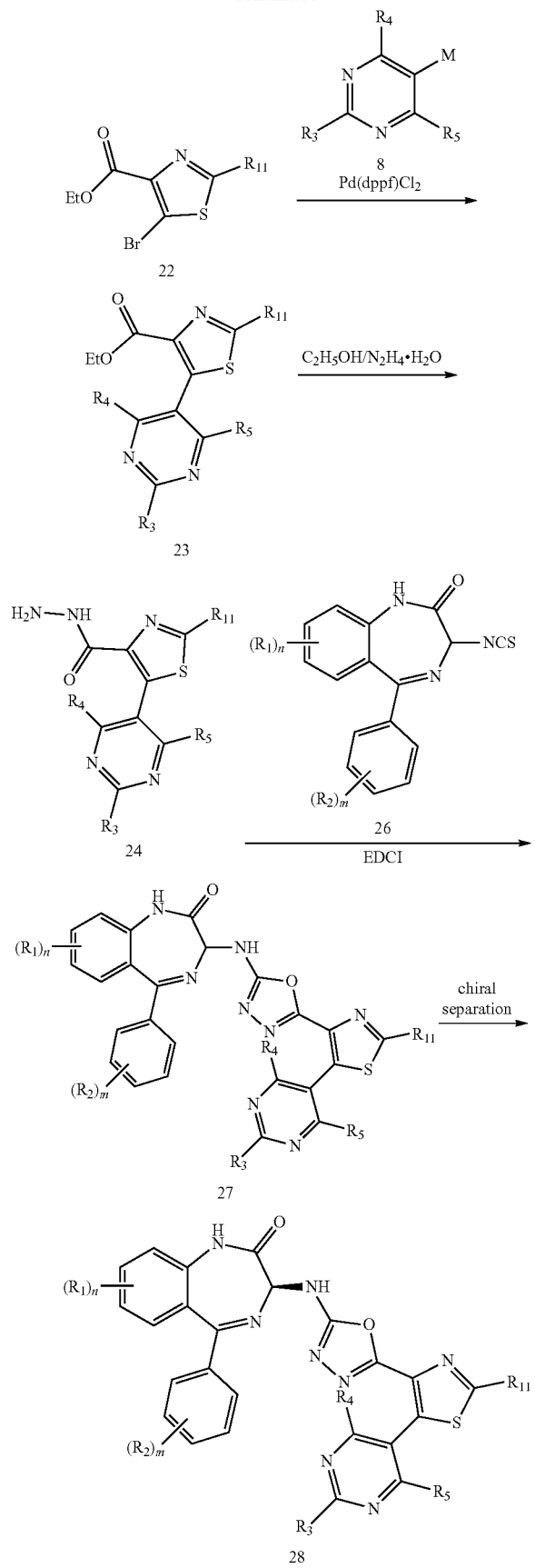

-continued

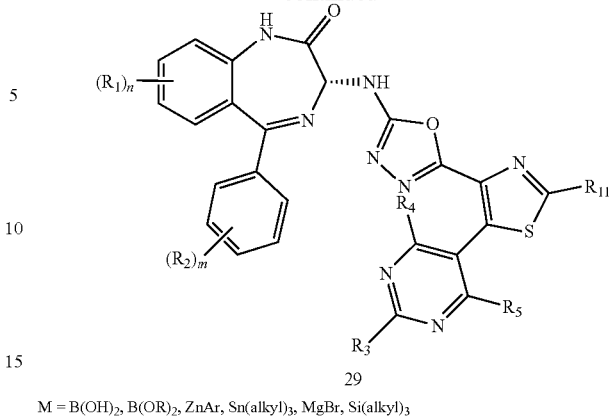

M = B(OH)₂, B(OR)₂, ZnAr, Sn(alkyl)₃, MgBr, Si(alkyl)₃

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Unless otherwise indicated, each of the compounds of the examples below was prepared and tested as a racemic mixture or, when possible, a diastereomeric mixture.

Example 1

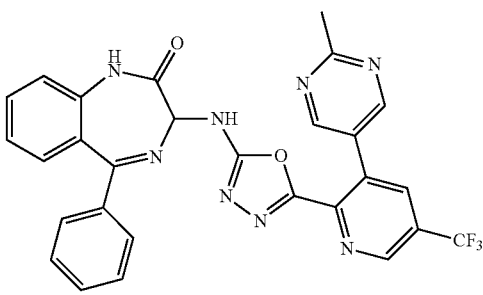 [SMILES: Cc1ncc(-c2cc(C(F)(F)F)cnc2-c2nnc(NC3N=C(c4ccccc4)c4ccccc4NC3=O)o2)cn1]

Example 1 Step a

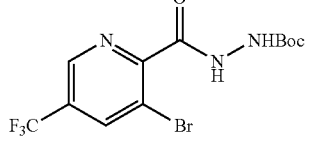

To a 50 mL round bottom flask with a stir bar, was added tert-butyl hydrazinecarboxylate (282 mg, 2.13 mmol), 3-bromo-5-(trifluoromethyl)picolinic acid (480 mg, 1.78 mmol) and HATU (811 mg, 2.13 mmol) in DMF (14.82 ml) at 0° C. DIPEA (460 mg, 3.56 mmol) was added to the resulting solution dropwise and the reaction mixture was warmed to room temperature and stirred for 2 h. The reaction was quenched by adding water/ethyl acetate and extracted with ethyl acetate. The combined organic layer was washed with water, dried (Na₂SO₄), concentrated, and purified by column chromatography (silica, Hexane: EtOAc=3:1) to give desired compound as light yellow solid (510 mg, 75% yield). ESI-MS m/z: 329.0 [M+H]⁺.

Example 1 Step b

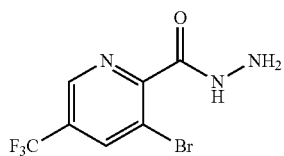

To a 25 mL round bottom flask with a stir bar, was added tert-butyl 2-(3-bromo-5-(trifluoromethyl)picolinoyl)hydrazine-1-carboxylate (510 mg, 1.33 mmol) in DCM (5 mL) at 0° C. The reaction mixture was added trifluoroacetic acid (1.5 mL, 19.9 mmol) dropwise and was stirred at 0° C. for 30 min. The reaction was then quenched with saturated sodium bicarbonate solution and then extracted with DCM. The combined organic layer was dried (Na₂SO₄), concentrated to give the desired compound (235 mg, 63%) as a white solid, which was used directly in the next step without further purification. ESI-MS m/z: 285.2 [M+H]⁺.

Example 1 Step c

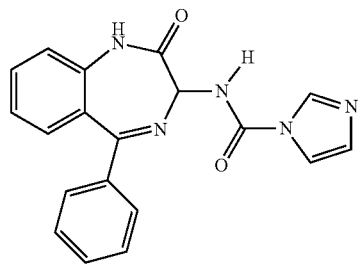 [SMILES: O=C1Nc2ccccc2C(c2ccccc2)=NC1NC(=O)n1ccnc1]

To a oven-dried round-bottomed flask was added CDI (3.87 g, 23.88 mmol) and acetonitrile (32 ml). The reaction was cooled to 0° C. 3-Amino-5-phenyl-1,3-dihydro-2H-benzo[e][1,4]diazepin-2-one (2 g, 7.96 mmol) was added to the reaction mixture portionwise over 5 mins. The reaction mixture was stirred at 0° C. for 2 hrs and then warmed to room temperature overnight. The reaction was then cooled to 0° C. and added water (0.860 g, 47.8 mmol) dropwise. The reaction was then warmed to room temperature again and the suspension was filtered to provide the desired product as the dry brownish solid (2.55 g, 93%), which can be used directly without further purification. ESI-MS m/z: 246.0 [M+H]⁺.

Example 1 Step d

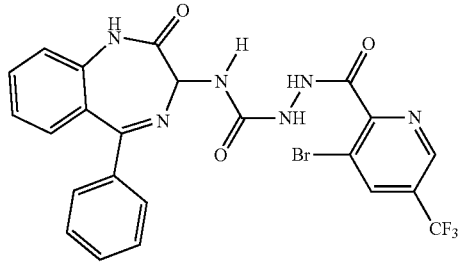 [SMILES: O=C(NNC(=O)c1ncc(C(F)(F)F)cc1Br)NC1N=C(c2ccccc2)c2ccccc2NC1=O]

To a 4 mL vial was added 3-bromo-5-(trifluoromethyl) picolinohydrazide (225 mg, 0.79 mmol, from Example 1, step b) and N-(2-oxo-5-phenyl-2,3-dihydro-1H-benzo[e][1, 4]diazepin-3-yl)-1H-imidazole-1-carboxamide (274 mg, 0.79 mmol, from Example 1, step c) in DMSO (0.53 mL). The reaction mixture was stirred at 30° C. for 48 h. The solution was then added to ice-cold water (20 mL) in 100 mL round-bottomed flask with stirring. The residue in the vial was rinsed with DMSO (1 mL) and added into the 100 mL round-bottomed flask. A pale yellow solid was immediately formed and stirring continued for additional 30 min before filtered through a fitted funnel and the solid was washed with water. The wet product was allowed to sit on the funnel while pulling vacuum for 2 h and then was further dried under high vacuum to give the desired product 2-(3-bromo-5-(trifluoromethyl)picolinoyl)-N-(2-oxo-5-phenyl-2, 3-dihydro-1H-benzo[e][1,4]diazepin-3-yl)hydrazine-1-carboxamide as a pale yellow solid (375 mg, 84%) that was used without further purification. ESI-MS m/z: 562.0 [M+H]⁺.

Example 1 Step e

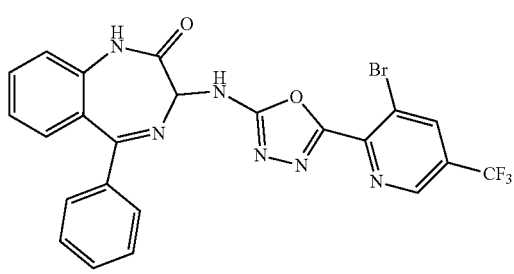 [SMILES: O=C1Nc2ccccc2C(c2ccccc2)=NC1Nc1nnc(-c2ncc(C(F)(F)F)cc2Br)o1]

2-(3-bromo-5-(trifluoromethyl)picolinoyl)-N-(2-oxo-5-phenyl-2,3-dihydro-1H-benzo[e][1,4]diazepin-3-yl)hydrazine-1-carboxamide (345 mg, 0.67 mmol) in DCM (8.3 mL) in a 50 mL round bottom flask was cooled at 0° C. Triethylamine (232 µl, 1.67 mmol) was added to the reaction dropwise followed by addition of TsCl (191 mg, 1.00 mmol). The reaction mixture was stirred at 0° C. for 1 h and slowly warmed to room temperature and stirred for additional 3 h. The reaction mixture was quenched with water and saturated sodium bicarbonate solution. The organic layer was separated and washed with brine. The organic layer was dried (Na₂SO₄), concentrated, and purified by column chromatography (silica, Hexane:Acetone=2:1) to give compound as light yellow solid (273 mg, 75% yield). ESI-MS m/z: 544.1 [M+H]⁺.

Example 1 Step f

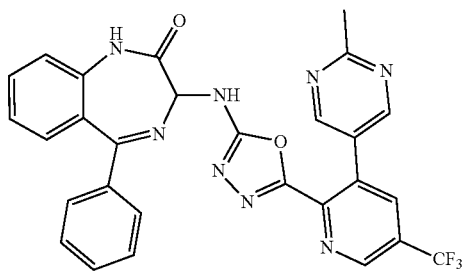 [SMILES: Cc1ncc(-c2cc(C(F)(F)F)cnc2-c2nnc(NC3N=C(c4ccccc4)c4ccccc4NC3=O)o2)cn1]

3-((5-(3-bromo-5-(trifluoromethyl)pyridin-2-yl)-1,3,4-oxadiazol-2-yl)amino)-5-phenyl-1,3-dihydro-2H-benzo[e][1,4]diazepin-2-one (55 mg, 0.1 mmol, from Example 1, step e), 2-methyl-5-(4,4,5,5-tetramethyl-1,3,2-dioxaborolan-2-yl)pyrimidine (33 mg, 0.150 mmol), Bis(triphenylphosphine)palladium(II) dichloride (7 mg, 0.01 mmol) and cesium carbonate (65 mg, 0.2 mmol) was added 1.6 mL of 1,4-dioxane and 0.4 mL of water in a 5 mL microwave tube. The reaction mixture was degassed for 5 min using nitrogen and then heated at 100° C. overnight. The reaction was quenched by adding water/ethyl acetate and extracted with ethyl acetate. The combined organic layer was washed with brine, dried ($Na_2SO_4$), concentrated, and purified by column chromatography (silica, Hexane:Acetone=2:1) to give desired compound as light yellow solid (31 mg, 56% yield). ESI-MS m/z: 557.6 [M+H]$^+$.

Examples 2-16 showed in Table 3 were prepared using a procedure similar as used to prepare Example 1 unless stated otherwise.

TABLE 3

| Example # | Structure | ESI-MS [M + H]$^+$ |
|---|---|---|
| 2 | 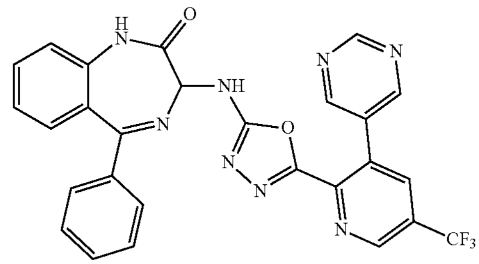 [SMILES: O=C1Nc2ccccc2C(c2ccccc2)=NC1Nc1nnc(-c2ncc(C(F)(F)F)cc2-c2cncnc2)o1] | 543.8 |
| 3 | 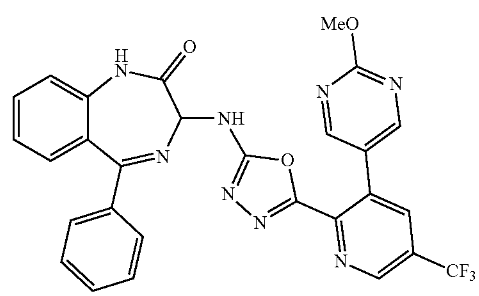 [SMILES: COc1ncc(-c2cc(C(F)(F)F)cnc2-c2nnc(NC3N=C(c4ccccc4)c4ccccc4NC3=O)o2)cn1] | 574.0 |
| 4 | 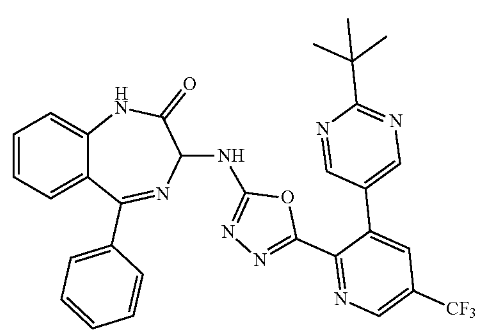 [SMILES: CC(C)(C)c1ncc(-c2cc(C(F)(F)F)cnc2-c2nnc(NC3N=C(c4ccccc4)c4ccccc4NC3=O)o2)cn1] | 601.2 |

TABLE 3-continued

| Example # | Structure | ESI-MS [M + H]+ |
|---|---|---|
| 5 | 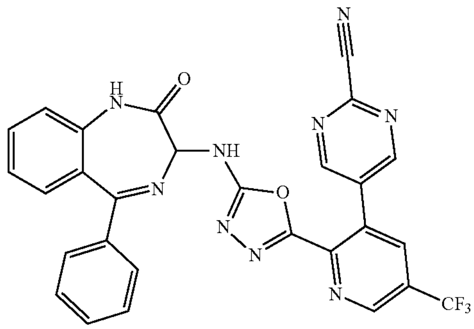 [SMILES: N#Cc1ncc(-c2cc(C(F)(F)F)cnc2-c2nnc(NC3N=C(c4ccccc4)c4ccccc4NC3=O)o2)cn1] | 567.8 |
| 6 | 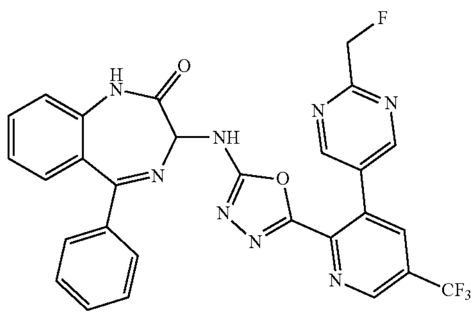 [SMILES: O=C1Nc2ccccc2C(c2ccccc2)=NC1Nc1nnc(-c2ncc(C(F)(F)F)cc2-c2cnc(CF)nc2)o1] | 576.0 |
| 7 | 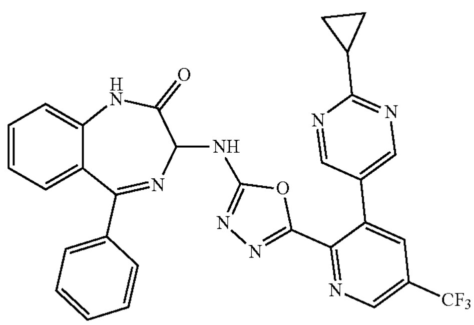 [SMILES: O=C1Nc2ccccc2C(c2ccccc2)=NC1Nc1nnc(-c2ncc(C(F)(F)F)cc2-c2cnc(C3CC3)nc2)o1] | 584.0 |
| 8 | 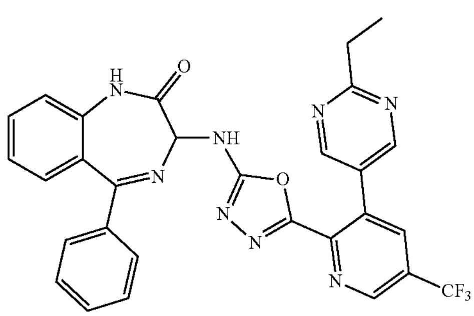 [SMILES: CCc1ncc(-c2cc(C(F)(F)F)cnc2-c2nnc(NC3N=C(c4ccccc4)c4ccccc4NC3=O)o2)cn1] | 571.0 |
| 9 | 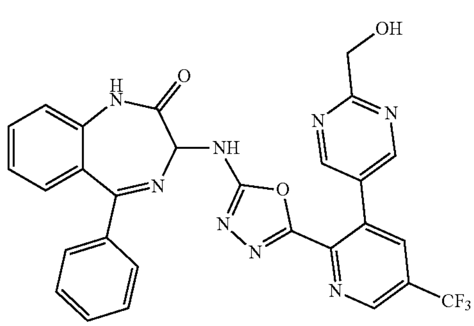 [SMILES: O=C1Nc2ccccc2C(c2ccccc2)=NC1Nc1nnc(-c2ncc(C(F)(F)F)cc2-c2cnc(CO)nc2)o1] | 574.0 |

TABLE 3-continued
| Example # | Structure | ESI-MS [M + H]+ |
|---|---|---|
| 10 | 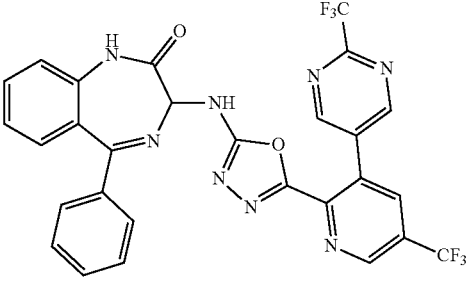 [SMILES: O=C1Nc2ccccc2C(c2ccccc2)=NC1Nc1nnc(-c2ncc(C(F)(F)F)cc2-c2cnc(C(F)(F)F)nc2)o1] | 611.0 |
| 11 | 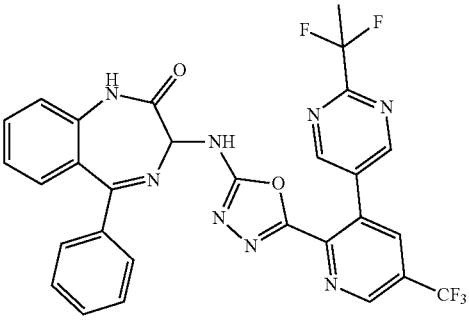 [SMILES: CC(F)(F)c1ncc(-c2cc(C(F)(F)F)cnc2-c2nnc(NC3N=C(c4ccccc4)c4ccccc4NC3=O)o2)cn1] | 607.0 |
| 12 | 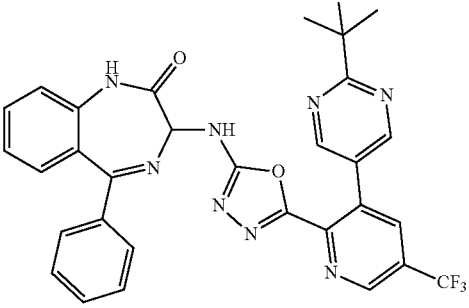 | 603.0 |
| 13 | 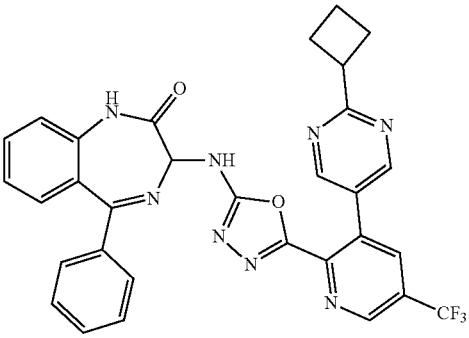 [SMILES: O=C1Nc2ccccc2C(c2ccccc2)=NC1Nc1nnc(-c2ncc(C(F)(F)F)cc2-c2cnc(C3CCC3)nc2)o1] | 597.0 |
| 14 | 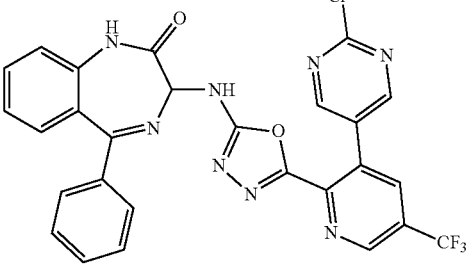 | 578.5 |

TABLE 3-continued

| Example # | Structure | ESI-MS [M + H]+ |
|---|---|---|
| 15 | 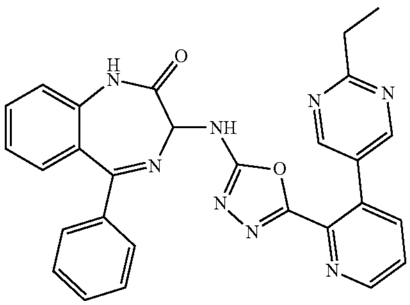 [SMILES: CCc1ncc(-c2cccnc2-c2nnc(NC3N=C(c4ccccc4)c4ccccc4NC3=O)o2)cn1] | 503.0 |
| 16 | 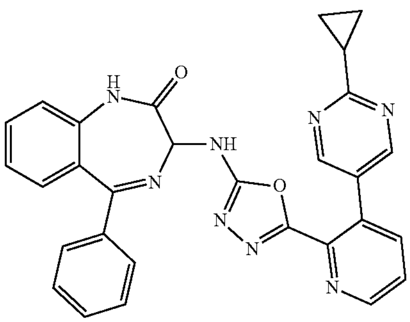 [SMILES: O=C1Nc2ccccc2C(c2ccccc2)=NC1Nc1nnc(-c2ncccc2-c2cnc(C3CC3)nc2)o1] | 515.2 |

Example 17

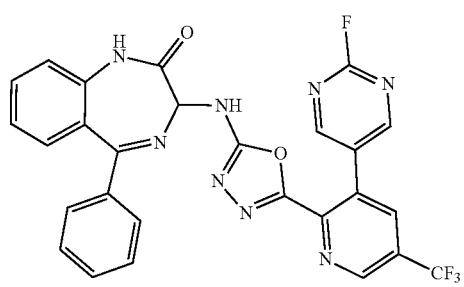 [SMILES: O=C1Nc2ccccc2C(c2ccccc2)=NC1Nc1nnc(-c2ncc(C(F)(F)F)cc2-c2cnc(F)nc2)o1]

Example 18

3-((5-(3-(2-chloropyrimidin-5-yl)-5-(trifluoromethyl)pyridin-2-yl)-1,3,4-oxadiazol-2-yl)amino)-5-phenyl-1,3-dihydro-2H-benzo[e][1,4]diazepin-2-one (45 mg, 0.078 mmol, Example 14) in acetonitrile (0.8 ml) was added 18-crown-6 (2.062 mg, 7.80 μmol) followed by potassium fluoride (13.59 mg, 0.234 mmol), the reaction mixture was heated at 60° C. overnight. The reaction mixture was added water/EtOAc and extracted with EtOAc, dried and concentrated. The residue was purified by column chromatography (silica, Hexane:EtOAc=1:4) to give the title compound as light yellow solid (3.0 mg, 7% yield). ESI-MS m/z: 562.0 [M+H]+.

3-((5-(3-(2-chloropyrimidin-5-yl)-5-(trifluoromethyl)pyridin-2-yl)-1,3,4-oxadiazol-2-yl)amino)-5-phenyl-1,3-dihydro-2H-benzo[e][1,4]diazepin-2-one (30 mg, 0.052 mmol, Example 14) in 1,4-dioxane (1 mL)/water (0.2 mL) was added potassium vinyltrifluoroborate salt (10.45 mg, 0.078 mmol), Cs$_2$CO$_3$ (33.9 mg, 0.104 mmol) and PdCl$_2$(PPh$_3$)$_2$ (3.65 mg, 5.20 μmol). The reaction mixture was degassed for 5 min and heated at 100° C. for 12 h. The reaction mixture was then added EtOAc/water, extracted with EtOAc (15 mL×3), the combined organic phase was dried, filtered and concentrated. The residue was purified by column chromatography (silica, Hexane:EtOAc=1:3) to give the title compound as light yellow solid (15 mg, 51% yield). ESI-MS m/z: 569.0 [M+H]+.

Example 19

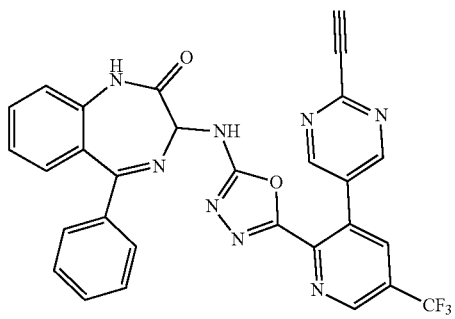 [SMILES: C#Cc1ncc(-c2cc(C(F)(F)F)cnc2-c2nnc(NC3N=C(c4ccccc4)c4ccccc4NC3=O)o2)cn1]

3-((5-(3-(2-ethynylpyrimidin-5-yl)-5-(trifluoromethyl)pyridin-2-yl)-1,3,4-oxadiazol-2-yl)amino)-5-phenyl-1,3-dihydro-2H-benzo[e][1,4]diazepin-2-one (30 mg, 0.052 mmol, from Example 14), copper (I) iodide (1.981 mg, 10.40 µmol), ethynyltrimethylsilane (7.66 mg, 0.078 mmol), triethylamine (105 mg, 1.040 mmol) and PdCl$_2$(PPh$_3$)$_2$ (3.65 mg, 5.20 µmol) in 1,4-dioxane (1 mL) was heated at 90° C. for 12 hrs. The reaction was quenched with EtOAc/water, extracted with EtOAc and concentrated. The residue in THF (0.3 mL) was then added tetrabutylammonium fluoride (1.0 M in THF, 0.3 mL) and the reaction was stirred at room temperature for 2 h. The reaction mixture was then added EtOAc and water, extracted with EtOAc, the combined organic phase was dried, filtered and concentrated. The residue was purified by column chromatography (silica, Hexane:EtOAc=1:3) to give the title compound as light yellow solid (3 mg, 17% yield). ESI-MS m/z: 567.0 [M+H]$^+$.

Example 20

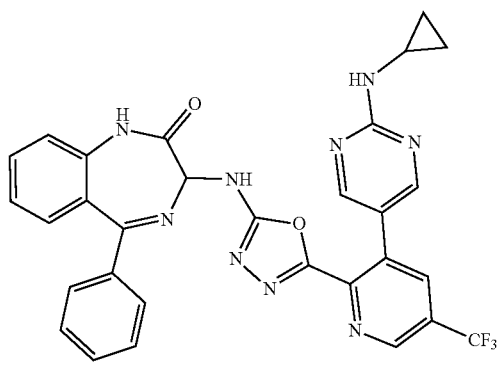 [SMILES: O=C1Nc2ccccc2C(c2ccccc2)=NC1Nc1nnc(-c2ncc(C(F)(F)F)cc2-c2cnc(NC3CC3)nc2)o1]

3-((5-(3-(2-chloropyrimidin-5-yl)-5-(trifluoromethyl)pyridin-2-yl)-1,3,4-oxadiazol-2-yl)amino)-5-phenyl-1,3-dihydro-2H-benzo[e][1,4]diazepin-2-one (33 mg, 0.057 mmol, from Example 14) in N-Methyl-2-pyrrolidinone (0.6 mL) was added cyclopropanamine (49 mg, 0.86 mmol). The reaction mixture was heated at 120° C. for 2 hrs. The reaction was quenched with EtOAc/water, extracted with EtOAc, dried and concentrated. The residue was purified by reverse phase HPLC (water/acetonitrile) to give the title compound as light yellow solid (10 mg, 29% yield). ESI-MS m/z: 599.0 [M+H]$^+$.

Example 21

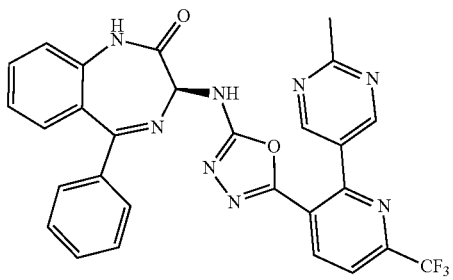 [SMILES: Cc1ncc(-c2nc(C(F)(F)F)ccc2-c2nnc(N[C@H]3N=C(c4ccccc4)c4ccccc4NC3=O)o2)cn1]

Example 21 Step a

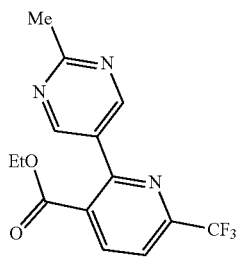 [SMILES: CCOC(=O)c1ccc(C(F)(F)F)nc1-c1cnc(C)nc1]

To a 5 ml microwave tube was added ethyl 2-bromo-6-(trifluoromethyl)nicotinate (100 mg, 0.34 mmol), (2-methylpyrimidin-5-yl)boronic acid (60 mg, 0.45 mmol), sodium bicarbonate (85 mg, 1.00 mmol) and Bis(triphenylphosphine)palladium(II) dichloride (28 mg, 0.03 mmol) in 2.4 mL of 1,4-dioxane and 0.6 mL of water. The reaction mixture was degassed for 5 min using nitrogen and then heated at 90° C. for 2 h. The reaction was quenched by adding water/ethyl acetate and extracted with ethyl acetate. The combined organic layer was washed with brine, dried (Na$_2$SO$_4$), concentrated, and purified by column chromatography (silica, Hexane:EtOAc=2:1) to give desired compound as light yellow solid (90 mg, 86% yield). ESI-MS m/z: 312.8 [M+H]$^+$.

Example 21 Step b

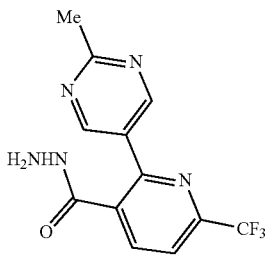

Ethyl 2-(2-methylpyrimidin-5-yl)-6-(trifluoromethyl)nicotinate (70 mg, 0.23 mmol) in EtOH (0.4 mL) and was added hydrazine hydrate (0.2 mL) at room temperature. The reaction was stirred for 2 h and added with water. The mixture was extracted with DCM, dried, filtered and concentrated. The residue was purified by column chromatography (silica, DCM:MeOH=10:1) to give the desired compound (66 mg, 99%) as a white solid. ESI-MS m/z: 297.8 [M+H]+.

Example 21 Step c

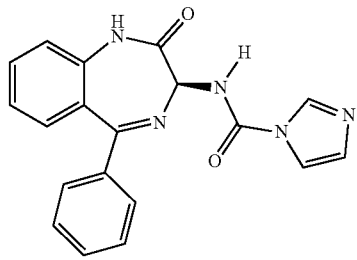 [SMILES: O=C1Nc2ccccc2C(c2ccccc2)=N[C@@H]1NC(=O)n1ccnc1]

To a oven-dried round-bottomed flask was added CDI (1.93 g, 11.94 mmol) in acetonitrile (16 ml) under nitrogen to give a white suspension. The reaction was cooled to 0° C. (S)-3-amino-5-phenyl-1,3-dihydro-2H-benzo[e][1,4]diazepin-2-one (1.0 g, 3.98 mmol) was added to the reaction mixture portionwise over 5 mins. The reaction mixture was stirred at 0° C. for 2 hrs and then warmed to room temperature overnight. The reaction was then cooled to 0° C. and added water (0.430 g, 23.9 mmol) dropwise. The reaction was then warmed to room temperature again and the suspension was filtered to provide the desired product as the pale yellow solid (1.23 g, 90%), which can be used directly without further purification. ESI-MS m/z: 246.0 [M+H]+.

Example 21 Step d

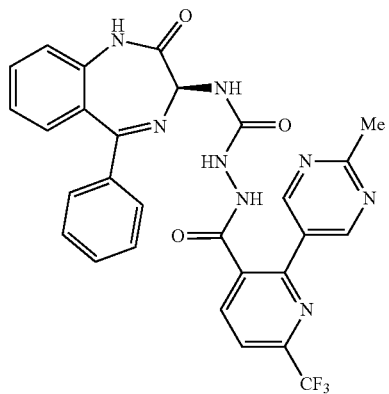 [SMILES: Cc1ncc(-c2nc(C(F)(F)F)ccc2C(=O)NNC(=O)N[C@H]2N=C(c3ccccc3)c3ccccc3NC2=O)cn1]

(S)—N-(2-oxo-5-phenyl-2,3-dihydro-1H-benzo[e][1,4]diazepin-3-yl)-1H-imidazole-1-carboxamide (37 mg, 0.11 mmol, step c) and 2-(2-methylpyrimidin-5-yl)-6-(trifluoromethyl)nicotinohydrazide (32 mg, 0.11 mmol, step b) was added DMSO (0.072 mL) in a 4 mL vial and the reaction mixture was allowed to stirred at room temperature for 30 h. Then the reaction was diluted with EtOAc (2 mL). The solution was then added to ice-cold water (20 mL) in 100 mL round-bottomed flask with stirring. The residue was rinsed with DMSO (1 mL) and added into the 100 mL round-bottomed flask. A pale yellow solid was immediately formed and stirring continued for additional 30 min before filtered through a fritted funnel and the solid was washed with water. The wet product was dried under high vacuum to give the desired product as a pale yellow solid (61 mg, 99%) that was used without further purification. ESI-MS m/z: 575.0 [M+H]+.

Example 21 Step e

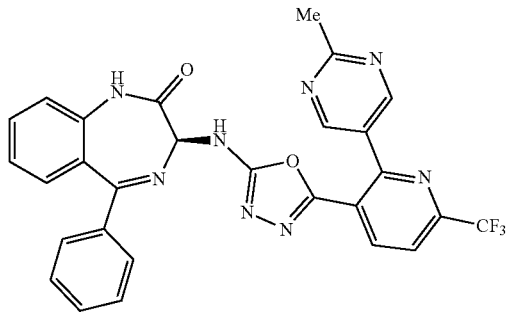 [SMILES: Cc1ncc(-c2nc(C(F)(F)F)ccc2-c2nnc(N[C@H]3N=C(c4ccccc4)c4ccccc4NC3=O)o2)cn1]

(S)-2-(2-(2-methylpyrimidin-5-yl)-6-(trifluoromethyl) nicotinoyl)-N-(2-oxo-5-phenyl-2,3-dihydro-1H-benzo[e][1,4]diazepin-3-yl)hydrazine-1-carboxamide (100 mg, 0.174 mmol, step d) in DCM (2.2 mL) in a 10 mL round bottom flask was cooled at 0° C. Triethylamine (61 µl, 0.435 mmol) was added to the reaction dropwise followed by addition of TsCl (50 mg, 0.261 mmol). The reaction mixture was stirred at 0° C. for 1 h and slowly warmed to room temperature and stirred for additional 3 h. The reaction mixture was quenched with water and saturated sodium bicarbonate solution. The organic layer was separated and washed with brine. The organic layer was dried (Na2SO4), concentrated, and purified by column chromatography (silica, Hexane:Acetone=3:1) to give the title compound as light yellow solid (47 mg, 49% yield). ESI-MS m/z: 557.0 [M+H]+.

Examples 22-23 in Table 4 were prepared using a procedure similar as used to prepare Example 21 unless stated otherwise.

TABLE 4

| Example# | Structure | ESI-MS [M + H]+ |
|---|---|---|
| 22 | 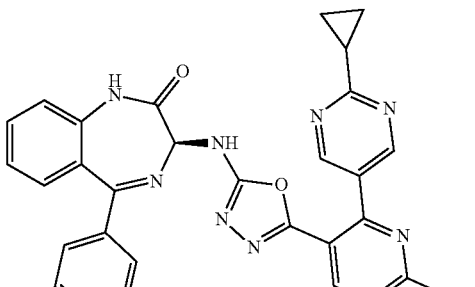 | 583.0 |
| 23 | 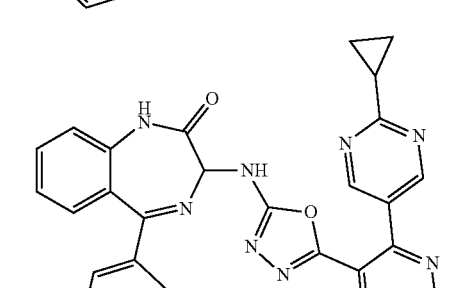 | 515.2 |

Example 24

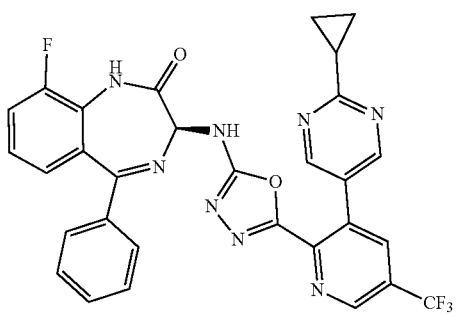 [SMILES: O=C1Nc2c(F)cccc2C(c2ccccc2)=N[C@@H]1Nc1nnc(-c2ncc(C(F)(F)F)cc2-c2cnc(C3CC3)nc2)o1]

Example 24 Step a

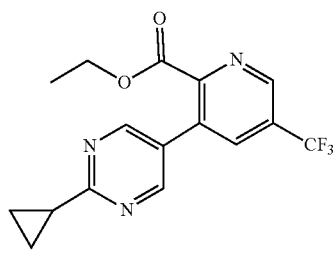 [SMILES: CCOC(=O)c1ncc(C(F)(F)F)cc1-c1cnc(C2CC2)nc1]

To a 30 ml microwave vial was added ethyl 3-chloro-5-(trifluoromethyl)picolinate (278 mg, 1.1 mmol), sodium bicarbonate (168 mg, 2 mmol), Pd(dppf)Cl$_2$·CH$_2$Cl$_2$ (83 mg, 0.1 mmol) and 2-cyclopropyl-5-(4,4,5-trimethyl-1,3,2-dioxaborolan-2-yl)pyrimidine (246 mg, 1.0 mmol) in 1,4-dioxane (4 mL) and water (1 mL). The reaction mixture was degassed using nitrogen for 5 min and then heated at 100° C. for 1 h. The reaction was added water/ethyl acetate and extracted with ethyl acetate. The combined organic layer was washed with water, dried (Na$_2$SO$_4$), concentrated, and purified by column chromatography (silica, Hexane:EtOAc=2:1) to give desired compound as light yellow solid (236 mg, 70% yield). ESI-MS m/z: 337.7 [M+H]+.

Example 24 Step b

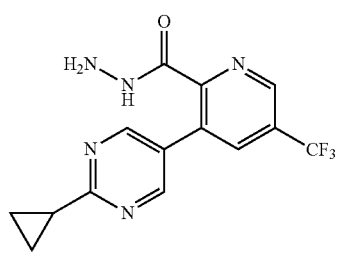 [SMILES: NNC(=O)c1ncc(C(F)(F)F)cc1-c1cnc(C2CC2)nc1]

ethyl 3-(2-cyclopropylpyrimidin-5-yl)-5-(trifluoromethyl)picolinate (337 mg, 1.0 mmol) in EtOH (1.3 mL) was added NH$_2$NH$_2$·H$_2$O (~50%, 0.65 mL) and the reaction was stirred at room temperature for 1 h. The reaction mixture was then added to cold water (10 mL) and the resulting precipitate was collected by filtration to give the desired compound (193 mg, 60%) as a white solid, which was used directly in the next step without further purification. ESI-MS m/z: 324.2 [M+H]+.

Example 24 Step c

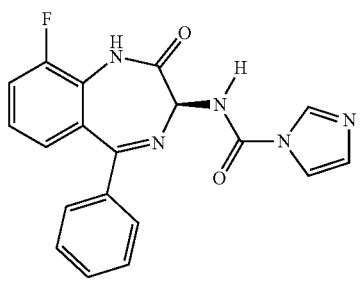 [SMILES: O=C1Nc2c(F)cccc2C(c2ccccc2)=N[C@@H]1NC(=O)n1ccnc1]

To a oven-dried round-bottomed flask was added CDI (1.95 g, 12 mmol) in acetonitrile (16 ml) under nitrogen to give a white suspension. The reaction was cooled to 0° C. (S)-3-amino-9-fluoro-5-phenyl-1,3-dihydro-2H-benzo[e][1,4]diazepin-2-one (1.07 g, 4.0 mmol) was added to the reaction mixture portionwise over 5 mins. The reaction mixture was stirred at 0° C. for 2 hrs and then warmed to room temperature overnight. The reaction was then cooled to 0° C. and added water (0.432 g, 24 mmol) dropwise. The reaction was then warmed to room temperature again and the suspension was filtered to provide the desired product as the pale yellow solid (1.32 g, 91%), which can be used directly without further purification. ESI-MS m/z: 364.1 [M+H]$^+$.

Example 24 Step d

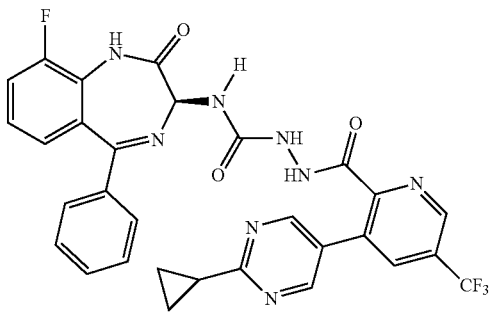 [SMILES: O=C(NNC(=O)c1ncc(C(F)(F)F)cc1-c1cnc(C2CC2)nc1)N[C@H]1N=C(c2ccccc2)c2cccc(F)c2NC1=O]

3-(2-cyclopropylpyrimidin-5-yl)-5-(trifluoromethyl)picolinohydrazide (200 mg, 0.62 mmol, step b) and (S)—N-(9-fluoro-2-oxo-5-phenyl-2,3-dihydro-1H-benzo[e][1,4]diazepin-3-yl)-1H-imidazole-1-carboxamide (228 mg, 0.62 mmol, step c) in a 4 mL vial was added DMSO (0.4 mL). The reaction mixture was allowed to stirred at room temperature for 48 h and then diluted with EtOAc (2 mL). The solution was then added to ice-cold water (20 mL) in 100 mL round-bottomed flask with stirring. The residue was rinsed with DMSO (1 mL) and added into the 100 mL round-bottomed flask. A pale yellow solid was immediately formed and stirring continued for additional 30 min before filtered through a fritted funnel and the solid was washed with water. The wet product was dried under high vacuum to give the desired product as a pale yellow solid (345 mg, 90%) that was used without further purification. ESI-MS m/z: 619.0 [M+H]$^+$.

Example 24 Step e

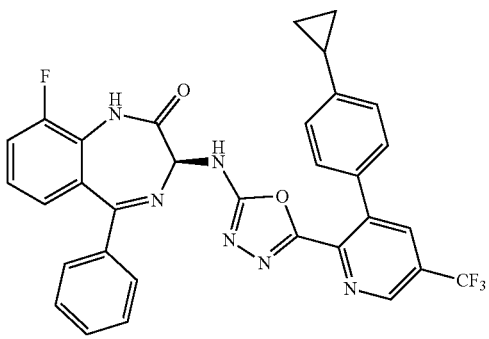 [SMILES: O=C1Nc2c(F)cccc2C(c2ccccc2)=N[C@@H]1Nc1nnc(-c2ncc(C(F)(F)F)cc2-c2ccc(C3CC3)cc2)o1]

(S)-2-(3-(2-cyclopropylpyrimidin-5-yl)-5-(trifluoromethyl)picolinoyl)-N-(9-fluoro-2-oxo-5-phenyl-2,3-dihydro-1H-benzo[e][1,4]diazepin-3-yl)hydrazine-1-carboxamide (540 mg, 0.87 mmol, step d) in DCM (8.0 mL) in a 25 mL round bottom flask was cooled at 0° C. Triethylamine (304 µl, 2.18 mmol) was added to the reaction dropwise followed by addition of TsCl (250 mg, 1.31 mmol). The reaction mixture was stirred at 0° C. for 1 h and slowly warmed to room temperature and stirred for additional 3 h. The reaction mixture was quenched with water and saturated sodium bicarbonate solution. The organic layer was separated and washed with brine. The organic layer was dried (Na$_2$SO$_4$), concentrated, and purified by column chromatography (silica, Hexane:Acetone=3:1) to give the title compound as light yellow solid (325 mg, 62% yield). ESI-MS m/z: 601.0 [M+H]$^+$.

Examples 25-31, 76 and 77 in Table 5, were prepared using a procedure similar as used to prepare Example 24 unless stated otherwise.

TABLE 5

| Example# | Structure | ESI-MS [M + H]$^+$ |
|---|---|---|
| 25 | 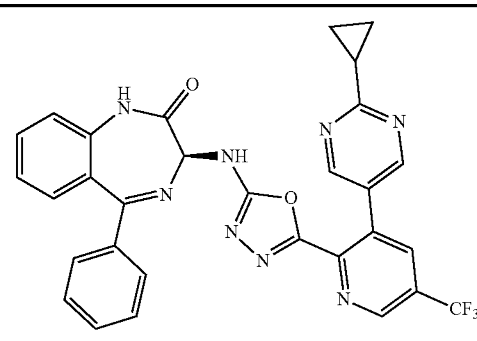 | 583.0 |

TABLE 5-continued

| Example# | Structure | ESI-MS [M + H]+ |
|---|---|---|
| 26 | 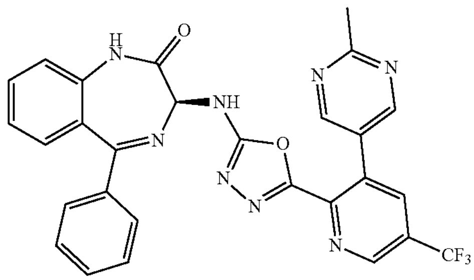 [SMILES: Cc1ncc(-c2cc(C(F)(F)F)cnc2-c2nnc(N[C@H]3N=C(c4ccccc4)c4ccccc4NC3=O)o2)cn1] | 557.0 |
| 27 | 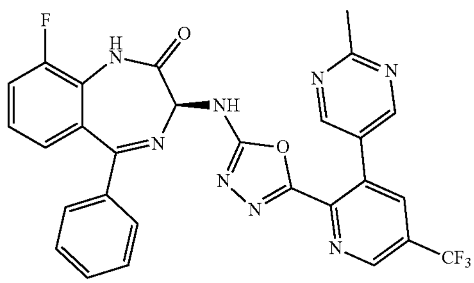 [SMILES: Cc1ncc(-c2cc(C(F)(F)F)cnc2-c2nnc(N[C@H]3N=C(c4ccccc4)c4cccc(F)c4NC3=O)o2)cn1] | 575.1 |
| 28 | 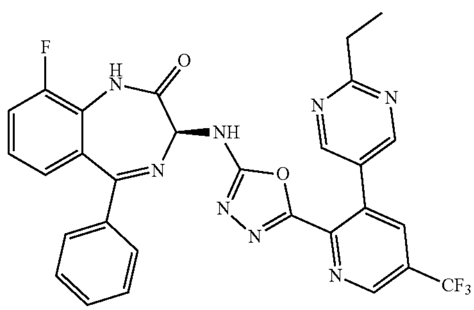 [SMILES: CCc1ncc(-c2cc(C(F)(F)F)cnc2-c2nnc(N[C@H]3N=C(c4ccccc4)c4cccc(F)c4NC3=O)o2)cn1] | 589.4 |
| 29 | 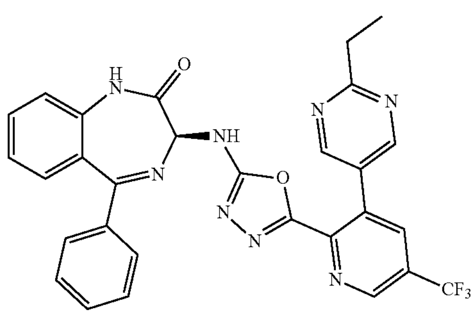 [SMILES: CCc1ncc(-c2cc(C(F)(F)F)cnc2-c2nnc(N[C@H]3N=C(c4ccccc4)c4ccccc4NC3=O)o2)cn1] | 571.4 |
| 30 | 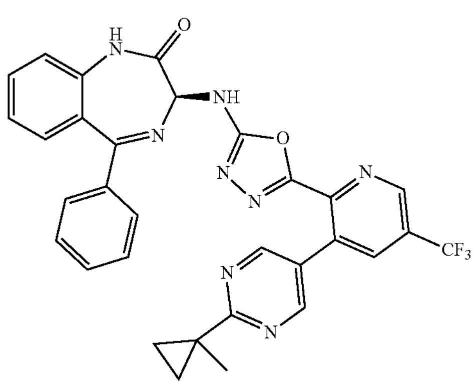 [SMILES: CC1(c2ncc(-c3cc(C(F)(F)F)cnc3-c3nnc(N[C@H]4N=C(c5ccccc5)c5ccccc5NC4=O)o3)cn2)CC1] | 597.3 |

TABLE 5-continued

| Example# | Structure | ESI-MS [M + H]+ |
|---|---|---|
| 31 | 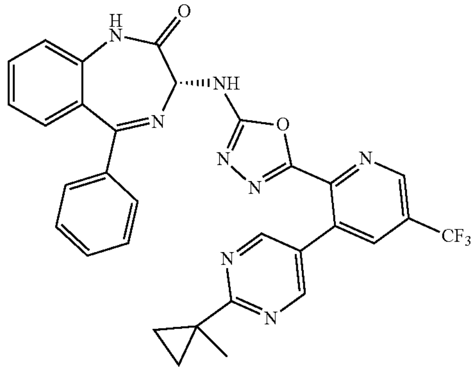 [SMILES: CC1(c2ncc(-c3cc(C(F)(F)F)cnc3-c3nnc(N[C@@H]4N=C(c5ccccc5)c5ccccc5NC4=O)o3)cn2)CC1] | 597.3 |
| 76 | 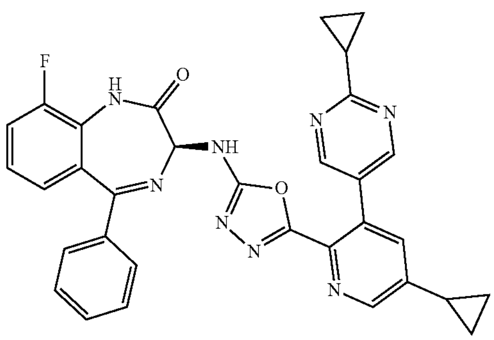 [SMILES: O=C1Nc2c(F)cccc2C(c2ccccc2)=N[C@@H]1Nc1nnc(-c2ncc(C3CC3)cc2-c2cnc(C3CC3)nc2)o1] | 573.4 |
| 77 | 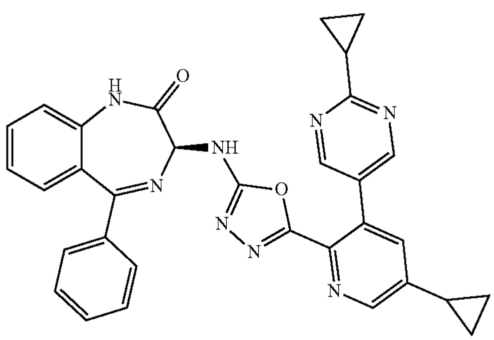 [SMILES: O=C1Nc2ccccc2C(c2ccccc2)=N[C@@H]1Nc1nnc(-c2ncc(C3CC3)cc2-c2cnc(C3CC3)nc2)o1] | 555.0 |

Example 32

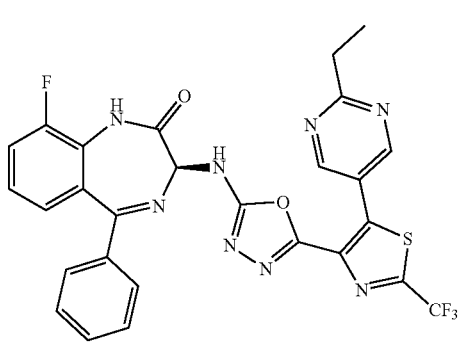 [SMILES: CCc1ncc(-c2sc(C(F)(F)F)nc2-c2nnc(N[C@H]3N=C(c4ccccc4)c4cccc(F)c4NC3=O)o2)cn1]

Example 32 Step a

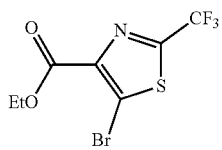

To a solution of ethyl 2-(trifluoromethyl)thiazole-4-carboxylate (1 g, 4.44 mmol) in THF (22.20 ml) was added LDA (2.442 ml, 4.88 mmol) at −78° C. under $N_2$. The mixture was stirred for 45 minutes at same temperature. To this, a solution of 1,2-dibromotetrachloroethane (2.169 g, 6.66 mmol) in THF (5 mL) was added dropwise and then warmed to room temperature over 2 hours. The reaction was quenched with saturated ammonium chloride solution. Water was added and the mixture was extracted with EtOAc (3×). The organic layer was combined, dried and concentrated. The crude product was added to a silica gel column and was eluted with ethyl acetate/hexane (0% to 50%) to give ethyl 5-bromo-2-(trifluoromethyl)thiazole-4-carboxylate (405 mg, 1.332 mmol, 30.0% yield) as a color solid. ESI-MS m/z: 304.9 [M+H]+.

Example 32 Step b

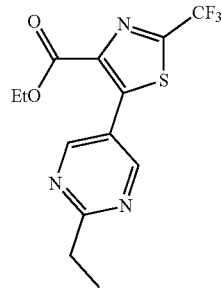 [SMILES: CCOC(=O)c1nc(C(F)(F)F)sc1-c1cnc(CC)nc1]

A solution of the compound ethyl 5-bromo-2-(trifluoromethyl)thiazole-4-carboxylate (1.6 g, 5.26 mmol) and 2-ethyl-5-(4,4,5,5-tetramethyl-1,3,2-dioxaborolan-2-yl)pyrimidine (1.2 g, 5.26 mmol), Pd(dppf)Cl₂ (385 mg, 0.53 mmol), NaHCO₃ (884 mg, 10.52 mmol) in 1,4-dioxane:H₂O=4:1 (20 mL) with an inert atmosphere of nitrogen was stirred for 4 hours at 90° C. The resulting solution was added water, extracted with EtOAc (×3), the organic layer was dried, filtered and concentrated. The crude product was purified by reverse phase C18 column chromatography (CH₃CN/H₂O) to afford desired product (1.26 g, 85%) as a yellow solid. ESI-MS m/z: 332.20 [M+H]+.

Example 32 Step c

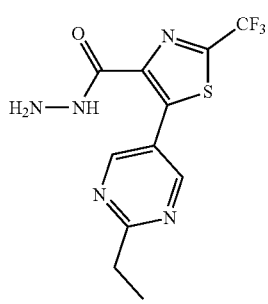 [SMILES: CCc1ncc(-c2sc(C(F)(F)F)nc2C(=O)NN)cn1]

A solution of the compound from step b (420 mg, 1.27 mmol) in NH₂NH₂·H₂O:EtOH=1:10 (11 mL) was stirred for 0.5 hour at room temperature. The resulting solution was concentrated. The crude product was purified by silica gel column (DCM/MeOH) to afford desired product (370 mg, 92%) as a yellow solid. ESI-MS m/z: 318.15 [M+H]+.

Example 32 Step d

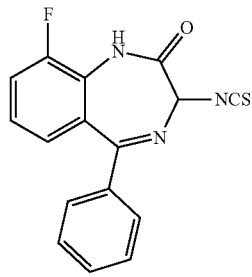

3-amino-9-fluoro-5-phenyl-1,3-dihydro-2H-benzo[e][1,4]diazepin-2-one (538 mg, 2.0 mmol) in DCM (20 mL) at 0° C. was added TCDI (356 mg, 2.0 mmol) and the reaction was stirred at room temperature for 2 h. The reaction mixture was concentrated, added cold water and the solid was filtered and dried to afford desired product (500 mg, 80%) as a yellow solid which can be used for the next step without further purification. ESI-MS m/z: 312.0 [M+H]+.

Example 32 Step e

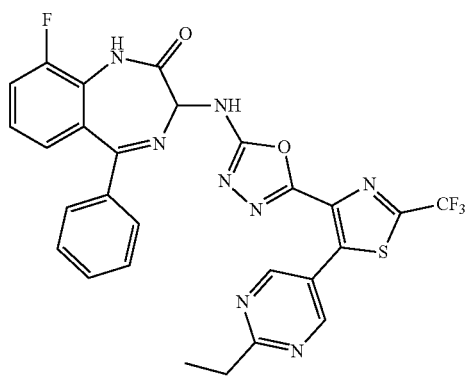 [SMILES: CCc1ncc(-c2sc(C(F)(F)F)nc2-c2nnc(NC3N=C(c4ccccc4)c4cccc(F)c4NC3=O)o2)cn1]

A solution of 5-(2-ethylpyrimidin-5-yl)-2-(trifluoromethyl)thiazole-4-carbohydrazide (150 mg, 1.16 mmol) and the compound from step d (472 mg, 1.52 mmol) in DMSO (2 mL) was stirred for 16 hours at room temperature. Then EDCI (894 mg, 4.66 mmol) was added to the solution. The resulting solution was stirred for 5 hours at 60° C. The solution was purified by Prep-HPLC (MeCN/H₂O) to give the desired compound as a white solid (130 mg, 18%). ESI-MS m/z: 595.25 [M+H]+.

Example 32 Step f
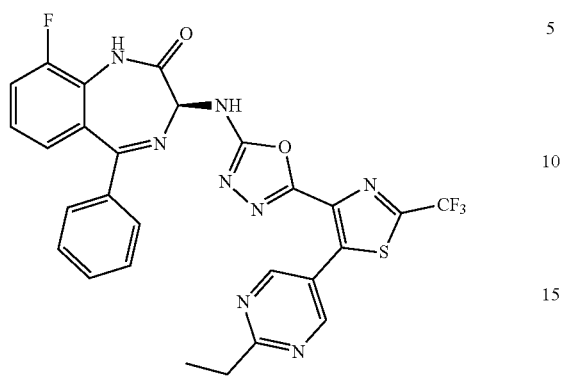
Example 32 was separated from racemic sample (Example 32, step e) using a chiral column (CHIRALPAK IE-3, Mobile phase: TBME (0.1% isopropylamine):EtOH=70:30). ESI-MS m/z: 595.2 [M+H]$^+$.
Examples 33-42 in Table 6 were prepared using a procedure similar as used to prepare Example 32 unless stated otherwise.
TABLE 6
| Example# | Structure | ESI-MS [M + H]$^+$ |
|---|---|---|
| 33 | 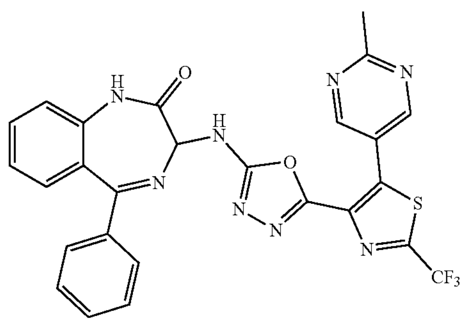 [SMILES: Cc1ncc(-c2sc(C(F)(F)F)nc2-c2nnc(NC3N=C(c4ccccc4)c4ccccc4NC3=O)o2)cn1] | 563.0 |
| 34 | 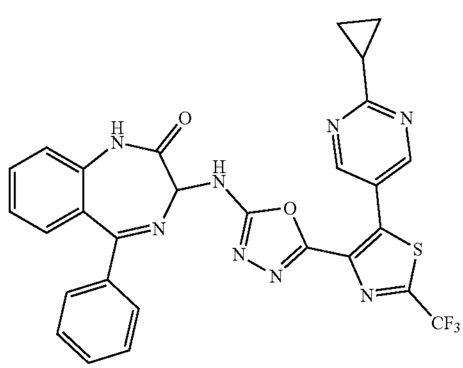 [SMILES: O=C1Nc2ccccc2C(c2ccccc2)=NC1Nc1nnc(-c2nc(C(F)(F)F)sc2-c2cnc(C3CC3)nc2)o1] | 589.0 |

TABLE 6-continued

| Example# | Structure | ESI-MS [M + H]+ |
|---|---|---|
| 35 | 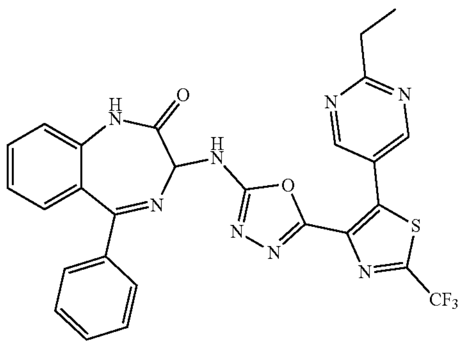 [SMILES: CCc1ncc(-c2sc(C(F)(F)F)nc2-c2nnc(NC3N=C(c4ccccc4)c4ccccc4NC3=O)o2)cn1] | 577.0 |
| 36 | 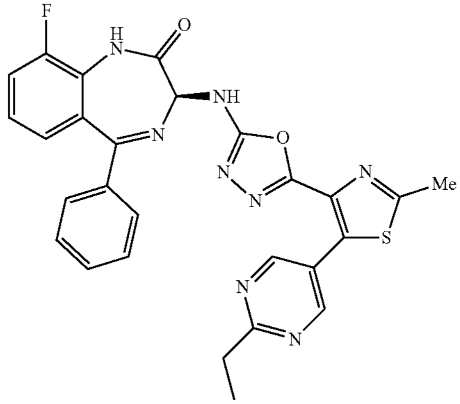 [SMILES: CCc1ncc(-c2sc(C)nc2-c2nnc(N[C@H]3N=C(c4ccccc4)c4cccc(F)c4NC3=O)o2)cn1] | 541.0 |
| 37 | 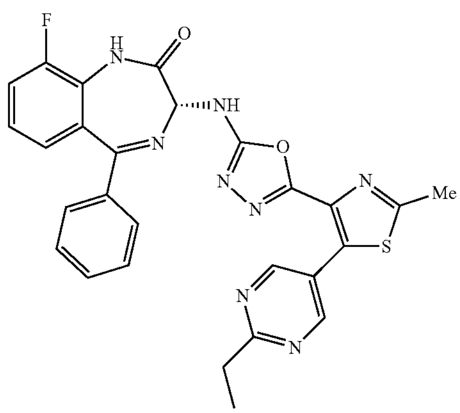 [SMILES: CCc1ncc(-c2sc(C)nc2-c2nnc(N[C@@H]3N=C(c4ccccc4)c4cccc(F)c4NC3=O)o2)cn1] | 541.0 |
| 38 | 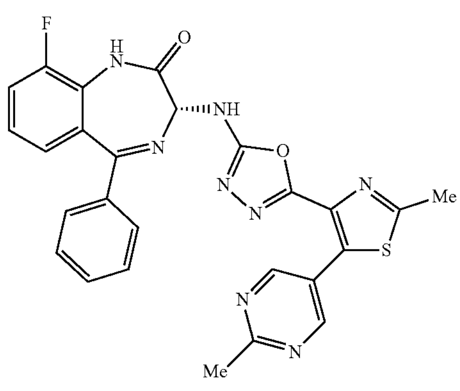 [SMILES: Cc1ncc(-c2sc(C)nc2-c2nnc(N[C@@H]3N=C(c4ccccc4)c4cccc(F)c4NC3=O)o2)cn1] | 527.3 |

TABLE 6-continued

| Example# | Structure | ESI-MS [M + H]+ |
|---|---|---|
| 39 | 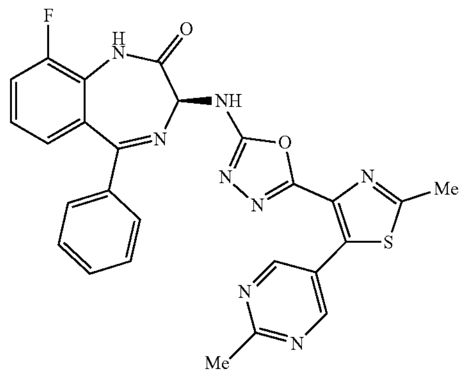 [SMILES: Cc1ncc(-c2sc(C)nc2-c2nnc(N[C@H]3N=C(c4ccccc4)c4cccc(F)c4NC3=O)o2)cn1] | 527.3 |
| 40 | 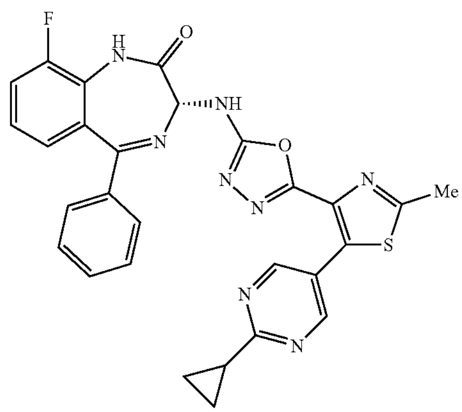 [SMILES: Cc1nc(-c2nnc(N[C@@H]3N=C(c4ccccc4)c4cccc(F)c4NC3=O)o2)c(-c2cnc(C3CC3)nc2)s1] | 553.3 |
| 41 | 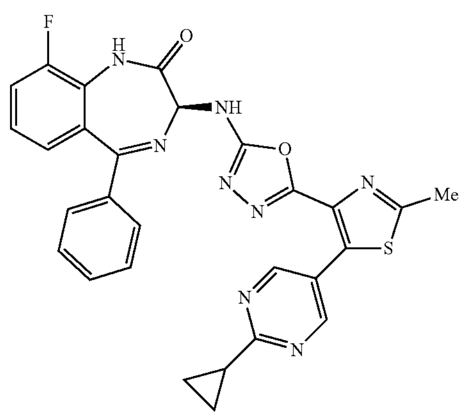 [SMILES: Cc1nc(-c2nnc(N[C@H]3N=C(c4ccccc4)c4cccc(F)c4NC3=O)o2)c(-c2cnc(C3CC3)nc2)s1] | 553.3 |
| 42 | 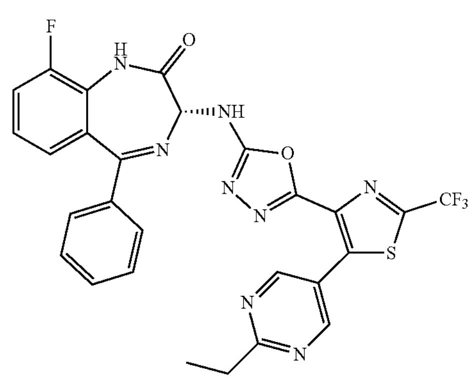 [SMILES: CCc1ncc(-c2sc(C(F)(F)F)nc2-c2nnc(N[C@@H]3N=C(c4ccccc4)c4cccc(F)c4NC3=O)o2)cn1] | 595.2 |

Example 43

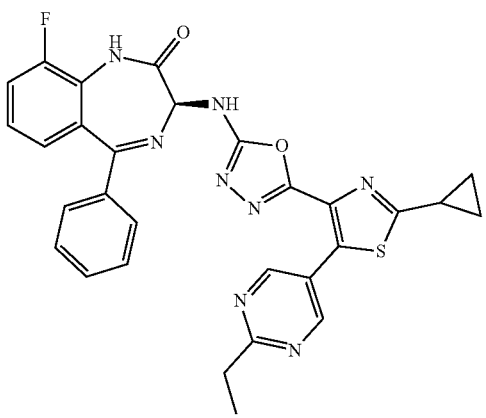 [SMILES: CCc1ncc(-c2sc(C3CC3)nc2-c2nnc(N[C@H]3N=C(c4ccccc4)c4cccc(F)c4NC3=O)o2)cn1]

Example 43 Step a

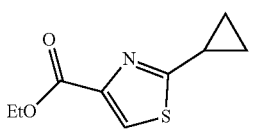 [SMILES: CCOC(=O)c1csc(C2CC2)n1]

A mixture of ethyl 2-bromo-1,3-thiazole-4-carboxylate (15.00 g, 63.53 mmol), Cs$_2$CO$_3$ (41.40 g, 127.06 mmol), Pd(dppf)Cl$_2$ (9.30 g, 12.70 mmol) and cyclopropylboronic acid (8.19 g, 95.30 mmol) in Toluene/H$_2$O (4:1) (250 mL) was stirred for 1 h at 100° C. under nitrogen atmosphere. The mixture was allowed to cool down to room temperature. The resulting mixture was diluted with water (100 mL). The aqueous layer was extracted with EtOAc (3×200 mL), dried, filtered and concentrated. The residue was purified by silica gel column chromatography, eluted with PE/EtOAc (7:1) to afford ethyl 2-cyclopropyl-1,3-thiazole-4-carboxylate (4.4 g, 35.11%) as a brown oil. ESI-MS m/z: 198.05 [M+H]$^+$.

Example 43 Step b

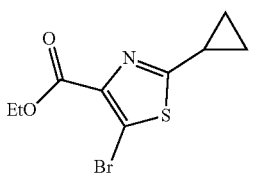 [SMILES: CCOC(=O)c1nc(C2CC2)sc1Br]

To a stirred solution of ethyl 2-cyclopropyl-1,3-thiazole-4-carboxylate (1.00 g, 5.07 mmol) in THF was added LDA (3.80 mL, 7.60 mmol) dropwise at −90° C. under nitrogen atmosphere. After 5 mins, to the above mixture was added 1,2-dibromo-1,1,2,2-tetrachloroethane (2.81 g, 8.61 mmol) dropwise at −90° C. The resulting mixture was stirred for additional 0.5 h at −90° C. The reaction was quenched with sat. NH$_4$C$_1$ (aq.) at room temperature. The aqueous layer was extracted with EtOAc (3×20 mL). The residue was purified by silica gel column chromatography, eluted with PE/EtOAc (5:1) to afford ethyl 5-bromo-2-cyclopropyl-1,3-thiazole-4-carboxylate (810 mg, 57.86%) as a light yellow solid. ESI-MS m/z: 275.85 [M+H]$^+$.

Example 43 Step c

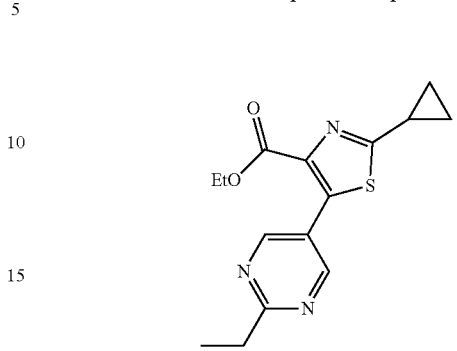

A solution of compound from step b (560 mg, 2.02 mmol) and 2-ethyl-5-(4,4,5,5-tetramethyl-1,3,2-dioxaborolan-2-yl)pyrimidine (474 mg, 2.02 mmol), Pd(dppf)Cl$_2$·CH$_2$Cl$_2$ (165 mg, 0.20 mmol) and NaHCO$_3$ (340 mg, 4.05 mmol) in 1,4-dioxane (20 mL)/H$_2$O (5 mL) was stirred for 1 h at 100° C. The resulting mixture was concentrated under reduced pressure. The residue was purified by reverse phase column chromatography with the following conditions (MeCN/H$_2$O=45%) to give the desired compound as a yellow solid (520 mg, 84%). ESI-MS m/z: 304.15 [M+H]$^+$.

Example 43 Step d

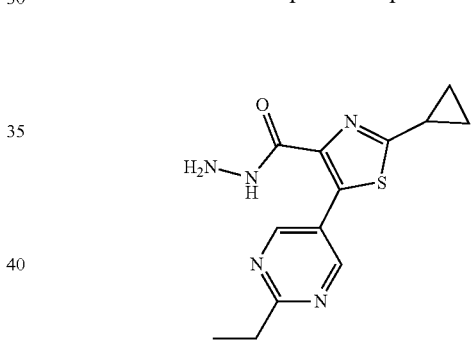

A solution of the compound from step c (520 mg, 1.71 mmol) and NH$_2$NH$_2$·H$_2$O (10 mL) in EtOH (10 mL) was stirred for 1 hour at 80° C. The resulting mixture was concentrated under reduced pressure. The residue product was purified by reverse phase column chromatography with the following conditions (MeCN/H$_2$O=35%) to give the titled compound as a light yellow solid (480 mg, 96%). ESI-MS m/z: 290.15 [M+H]$^+$.

Example 43 Step e

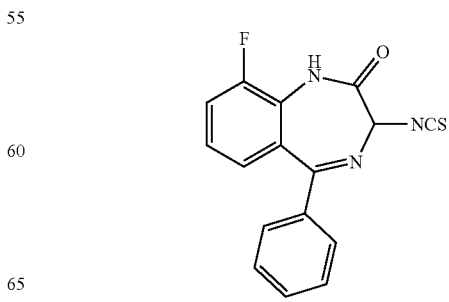

3-amino-9-fluoro-5-phenyl-1,3-dihydro-2H-benzo[e][1,4]diazepin-2-one (538 mg, 2.0 mmol) in DCM (20 mL) at 0° C. was added TCDI (356 mg, 2.0 mmol) and the reaction was stirred at room temperature for 2 h. The reaction mixture was concentrated, added cold water and the solid was filtered and dried to afford desired product (500 mg, 80%) as a yellow solid which can be used for the next step without further purification. ESI-MS m/z: 312.0 [M+H]+.

Example 43 Step f

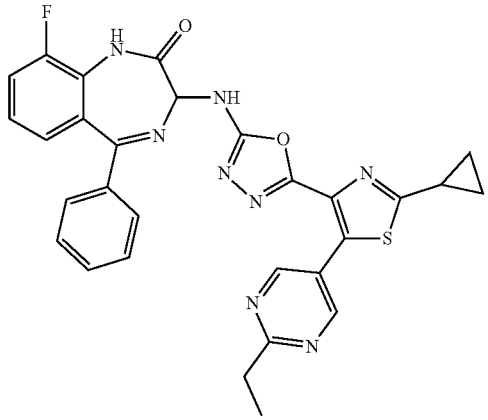 [SMILES: CCc1ncc(-c2sc(C3CC3)nc2-c2nnc(NC3N=C(c4ccccc4)c4cccc(F)c4NC3=O)o2)cn1]

A solution of the compound from step d (336 mg, 1.16 mmol) and the compound from step e (472 mg, 1.52 mmol) in DMSO (2 mL) was stirred for 16 hours at room temperature. Then EDCI (894 mg, 4.66 mmol) was added to the solution. The resulting solution was stirred for 5 hours at 60° C. The solution was purified by Prep-HPLC (MeCN/H₂O) to give the desired compound as a white solid (150 mg, 25%). ESI-MS m/z: 595.25 [M+H]+.

Example 43 Step g

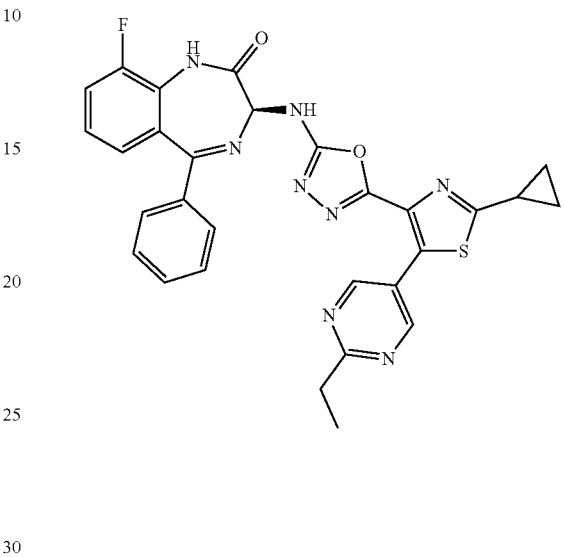

Example 43 was separated from racemic sample (Example 43, step f) using a chiral column (CHIRALPAK IE-3, Mobile phase: TBME (0.1% isopropylamine):EtOH=70:30). ESI-MS m/z: 567.1 [M+H]+.

Examples 44-57 in Table 7 were prepared using a procedure similar as used to prepare Example 43 unless stated otherwise.

TABLE 7

| Example# | Structure | ESI-MS [M + H]+ |
|---|---|---|
| 44 | 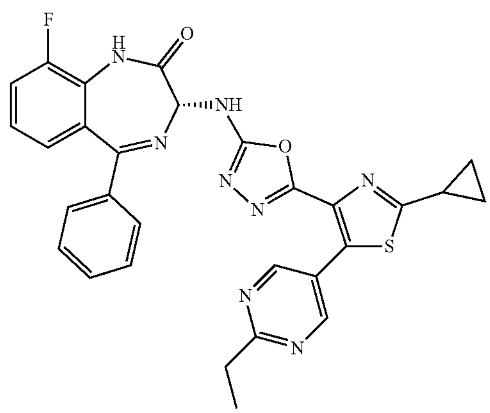 [SMILES: CCc1ncc(-c2sc(C3CC3)nc2-c2nnc(N[C@@H]3N=C(c4ccccc4)c4cccc(F)c4NC3=O)o2)cn1] | 567.1 |

TABLE 7-continued
| Example# | Structure | ESI-MS [M + H]+ |
|---|---|---|
| 45 | 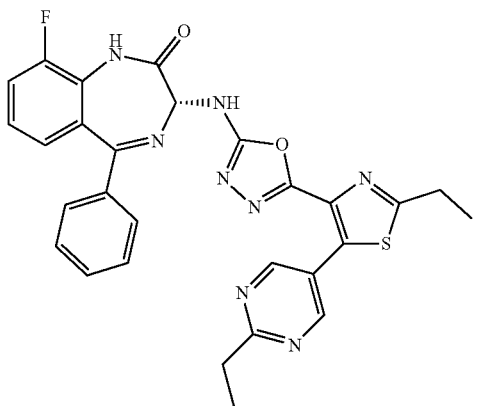 [SMILES: CCc1ncc(-c2sc(CC)nc2-c2nnc(N[C@@H]3N=C(c4ccccc4)c4cccc(F)c4NC3=O)o2)cn1] | 552.2 |
| 46 | 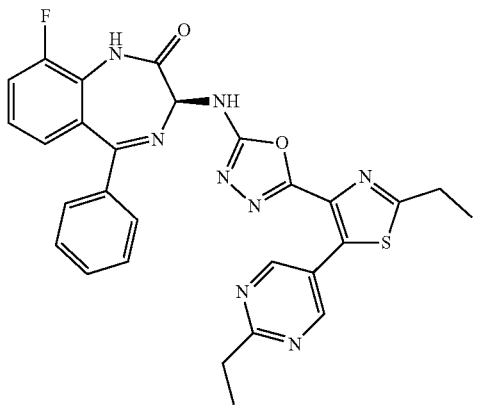 [SMILES: CCc1ncc(-c2sc(CC)nc2-c2nnc(N[C@H]3N=C(c4ccccc4)c4cccc(F)c4NC3=O)o2)cn1] | 552.2 |
| 47 | 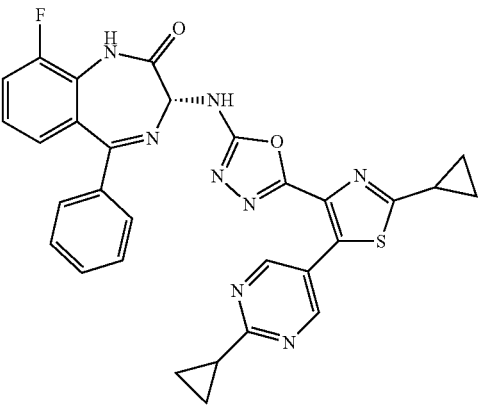 [SMILES: O=C1Nc2c(F)cccc2C(c2ccccc2)=N[C@H]1Nc1nnc(-c2nc(C3CC3)sc2-c2cnc(C3CC3)nc2)o1] | 579.3 |

TABLE 7-continued

| Example# | Structure | ESI-MS [M + H]+ |
|---|---|---|
| 48 | 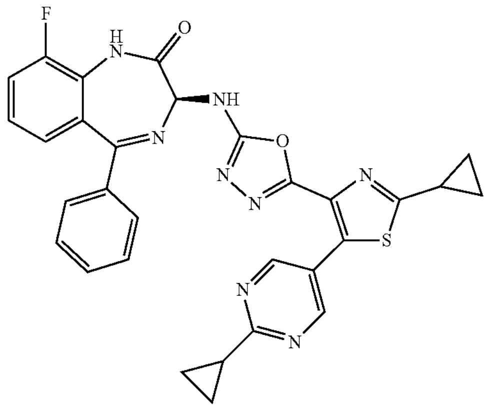 [SMILES: O=C1Nc2c(F)cccc2C(c2ccccc2)=N[C@@H]1Nc1nnc(-c2nc(C3CC3)sc2-c2cnc(C3CC3)nc2)o1] | 579.3 |
| 49 | 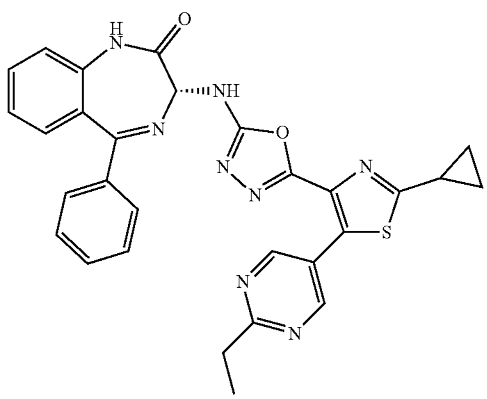 [SMILES: CCc1ncc(-c2sc(C3CC3)nc2-c2nnc(N[C@@H]3N=C(c4ccccc4)c4ccccc4NC3=O)o2)cn1] | 549.2 |
| 50 | 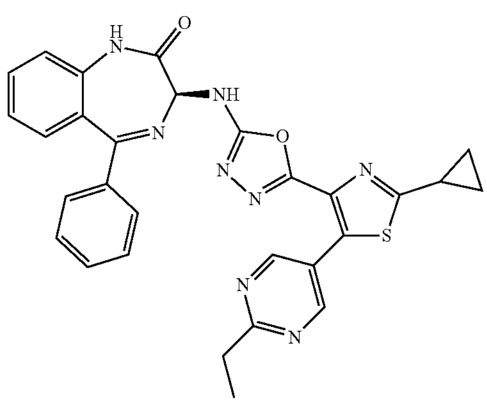 [SMILES: CCc1ncc(-c2sc(C3CC3)nc2-c2nnc(N[C@H]3N=C(c4ccccc4)c4ccccc4NC3=O)o2)cn1] | 549.2 |
| 51 | 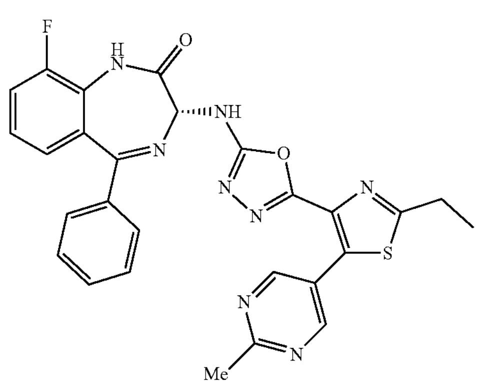 [SMILES: CCc1nc(-c2nnc(N[C@@H]3N=C(c4ccccc4)c4cccc(F)c4NC3=O)o2)c(-c2cnc(C)nc2)s1] | 541.3 |

TABLE 7-continued

| Example# | Structure | ESI-MS [M + H]+ |
|---|---|---|
| 52 | 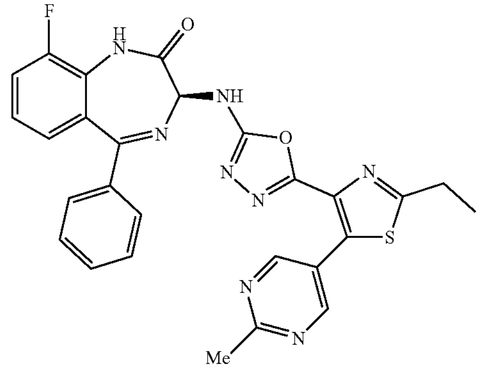 [SMILES: CCc1nc(-c2nnc(N[C@H]3N=C(c4ccccc4)c4cccc(F)c4NC3=O)o2)c(-c2cnc(C)nc2)s1] | 541.3 |
| 53 | 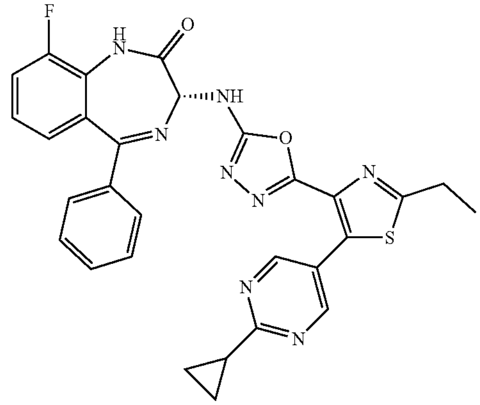 [SMILES: CCc1nc(-c2nnc(N[C@@H]3N=C(c4ccccc4)c4cccc(F)c4NC3=O)o2)c(-c2cnc(C3CC3)nc2)s1] | 567.3 |
| 54 | 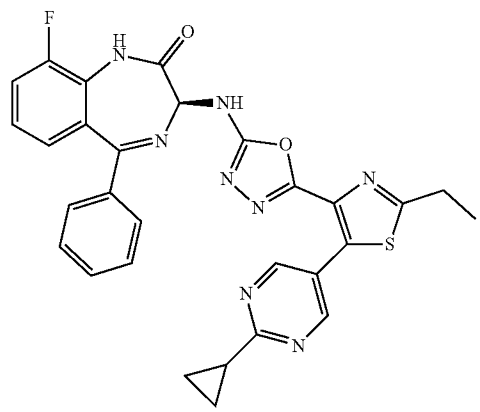 [SMILES: CCc1nc(-c2nnc(N[C@H]3N=C(c4ccccc4)c4cccc(F)c4NC3=O)o2)c(-c2cnc(C3CC3)nc2)s1] | 567.3 |
| 55 | 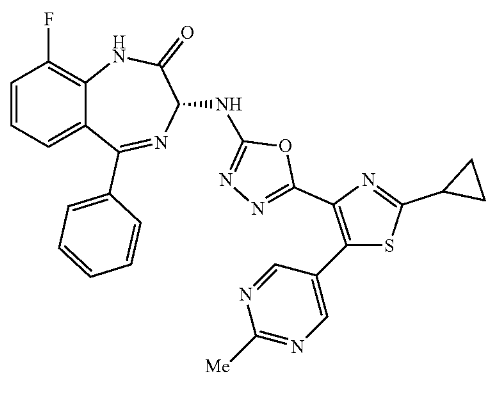 [SMILES: Cc1ncc(-c2sc(C3CC3)nc2-c2nnc(N[C@@H]3N=C(c4ccccc4)c4cccc(F)c4NC3=O)o2)cn1] | 553.2 |

TABLE 7-continued

| Example# | Structure | ESI-MS [M + H]+ |
|---|---|---|
| 56 | 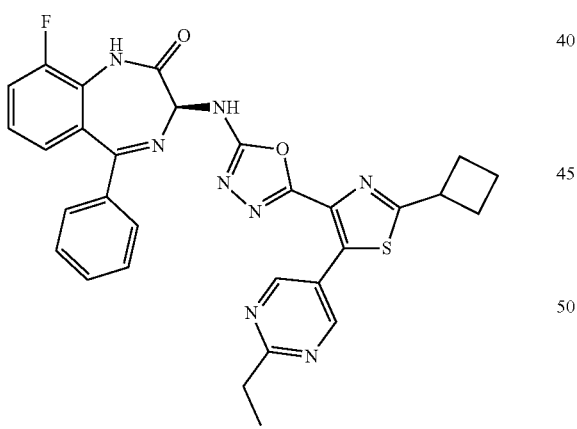 | 553.2 |
| 57 | 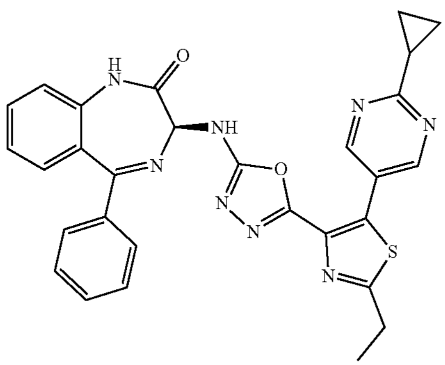 [SMILES: CCc1nc(-c2nnc(N[C@H]3N=C(c4ccccc4)c4ccccc4NC3=O)o2)c(-c2cnc(C3CC3)nc2)s1] | 537.2 |

Example 58

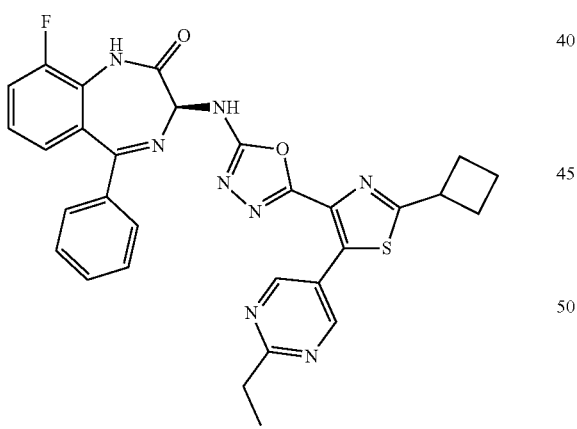

Example 58 Step a

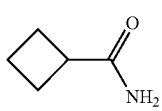

A solution of cyclobutanecarboxylic acid (87.00 g, 0.869 mol), oxalyl chloride (220.58 g, 1737.94 mmol)) in DCM (300 mL) was added DMF (10 mL) and the reaction mixture was stirred for 2 hours at room temperature. To $NH_3·H_2O$ (300 mL) was added the mixture dropwise over 1 h at 0° C. The aqueous layer was extracted with DCM (60 L), dried and filtered. The resulting mixture was concentrated under reduced pressure to get the desired product (75 g, 87.06%).

Example 58 Step b

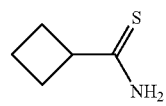

A solution of the compound from step a (9.00 g, 90.78 mmol) and Lawesson Reagent (22.03 g, 54.46 mmol) in THF (150 mL) was stirred for 3 hours at room temperature. The reaction was quenched by the addition of sat. $NaHCO_3$ (aq.) (200 mL) at room temperature. The aqueous layer was extracted with EtOAc (3×100 mL), dried and filtered. The resulting mixture was concentrated under reduced pressure. The residue was purified by silica gel column chromatography, eluted with PE/EtOAc (2:1) to afford the desired product as an off-white solid (6 g, 57.37%). ESI-MS m/z: 116.05 [M+H]+.

Example 58 Step c

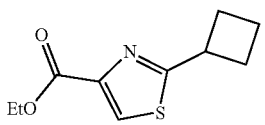 [SMILES: CCOC(=O)c1csc(C2CCC2)n1]

Into a 250 mL round-bottom flask were added the compound from step b (6.00 g, 52.08 mmol), ethyl 3-bromo-2-oxopropanoate (19.30 g, 98.96 mmol) and EtOH (100 mL) at room temperature. The resulting mixture was stirred for 2 hours at 80° C. The resulting mixture was extracted with EtOAc (3×100 mL), dried, filtered and concentrated. The residue was purified by reverse phase column chromatography to afford the product as a dark orange liquid (8.8 g, 79.96%). ESI-MS m/z: 212.10 [M+H]$^+$.

Example 58 Step d

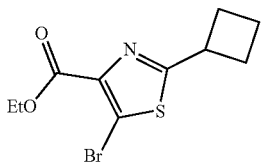 [SMILES: CCOC(=O)c1nc(C2CCC2)sc1Br]

Into a 500 mL 3-necked round-bottom flask were added the compound from step c (4.00 g, 18.93 mmol) and THF (200 mL) at room temperature under nitrogen atmosphere, the mixture was cool down to −90° C., then LDA (2.43 g, 22.72 mmol) was added to the mixture and stirred for 20 min at −90° C. 1,2-dibromo-1,1,2,2-tetrachloroethane (10.48 g, 32.18 mmol) in THF (20 mL) was added to the mixture at −90° C., the resulting mixture was stirred for additional 1 h at room temperature. The reaction was quenched with water/EtOAc, extracted with EtOAc, filtered and concentrated. The residue was purified by reverse phase column chromatography to afford the desired product as a brown liquid (3.8 g, 69.17%). ESI-MS m/z: 290.85 [M+H]$^+$.

Example 58 Step e

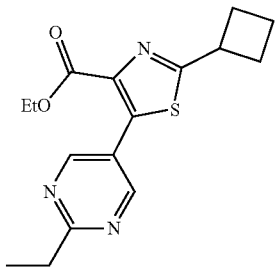 [SMILES: CCOC(=O)c1nc(C2CCC2)sc1-c1cnc(CC)nc1]

A mixture of the compound from 2-ethyl-5-(4,4,5,5-tetramethyl-1,3,2-dioxaborolan-2-yl)pyrimidine (500 mg, 2.13 mmol) and ethyl 5-bromo-2-cyclobutyl-1,3-thiazole-4-carboxylate (619 mg, 2.13 mmol, step d), NaHCO$_3$ (358 mg, 4.27 mmol and Pd(dppf)Cl$_2$ (156 mg, 0.21 mmol) in 1,4-dioxane (10 mL) and H$_2$O (4 mL) was stirred for 1 h at 100° C. under nitrogen atmosphere. The residue was purified by silica gel column chromatography, eluted with PE/EA (1:1) to afford crude product as a brown solid (1 g), which was used directly without further purification. ESI-MS m/z: 318.20 [M+H]$^+$.

Example 58 Step f

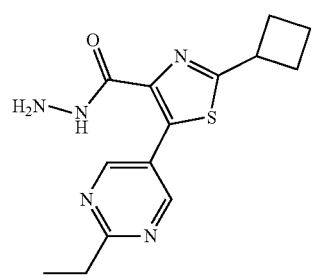 [SMILES: CCc1ncc(-c2sc(C3CCC3)nc2C(=O)NN)cn1]

Into a 100 mL round-bottom flask were added the compound from step e (1.00 g, 3.15 mmol), NH$_2$NH$_2$·H$_2$O (5 mL, 102.87 mmol) and EtOH (20 mL) at room temperature. The resulting mixture was stirred for 2 hours at 80° C. The mixture was allowed to cool down to room temperature to get the solid, the precipitated solids were collected by filtration and washed with water (4×20 mL) to get the desired product as a brown solid. ESI-MS m/z: 304.20 [M+H]$^+$.

Example 58 Step g

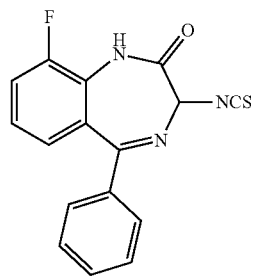

3-amino-9-fluoro-5-phenyl-1,3-dihydro-2H-benzo[e][1,4]diazepin-2-one (538 mg, 2.0 mmol) in DCM (20 mL) at 0° C. was added TCDI (356 mg, 2.0 mmol) and the reaction was stirred at room temperature for 2 h. The reaction mixture was concentrated, added cold water and the solid was filtered and dried to afford desired product (500 mg, 80%) as a yellow solid which can be used for the next step without further purification. ESI-MS m/z: 312.0 [M+H]$^+$.

Example 58 Step h

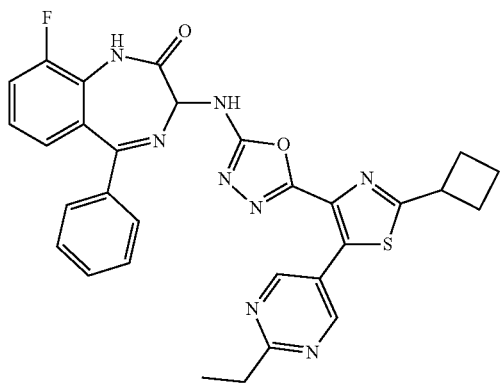 [SMILES: CCc1ncc(-c2sc(C3CCC3)nc2-c2nnc(NC3N=C(c4ccccc4)c4cccc(F)c4NC3=O)o2)cn1]

A solution of the compound from step f (304 mg, 1.0 mmol) and the compound from step g (405 mg, 1.3 mmol) in DMSO (2 mL) was stirred for 16 hours at room temperature. Then EDCI (788 mg, 4.0 mmol) was added to the solution. The resulting solution was stirred for 5 hours at 60° C. The solution was purified by Prep-HPLC (MeCN/H$_2$O) to give the desired compound as a white solid (133 mg, 23%). ESI-MS m/z: 581.4 [M+H]$^+$.

Example 58 Step i

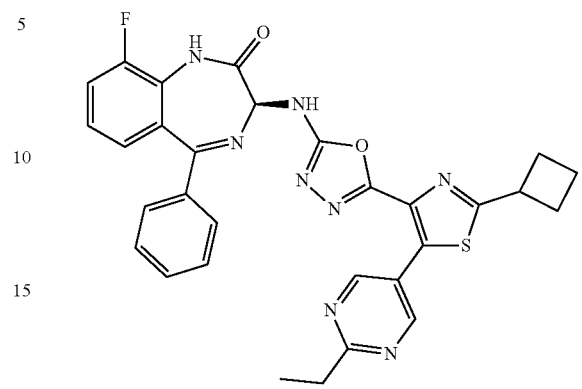

Example 58 was separated from racemic sample (Example 58, step h) using a chiral column (CHIRALPAK IE-3, Mobile phase: TBME (0.1% isopropylamine): EtOH=70:30). ESI-MS m/z: 581.4 [M+H]$^+$.

Example 59-75 in Table 8 were prepared using a procedure similar as used to prepare Example 58 unless stated otherwise.

TABLE 8

| Example# | Structure | ESI-MS [M + H]$^+$ |
|---|---|---|
| 59 | 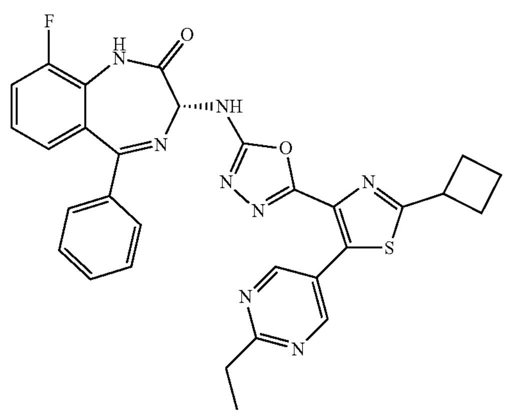 [SMILES: CCc1ncc(-c2sc(C3CCC3)nc2-c2nnc(N[C@@H]3N=C(c4ccccc4)c4cccc(F)c4NC3=O)o2)cn1] | 581.4 |
| 60 | 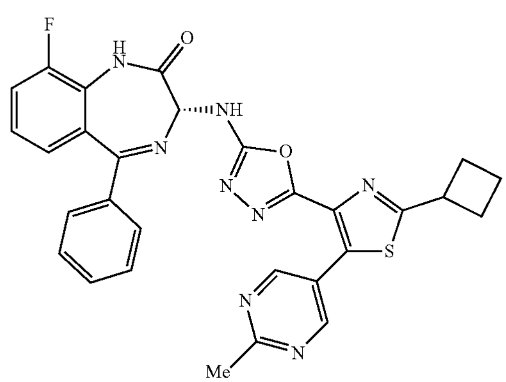 [SMILES: Cc1ncc(-c2sc(C3CCC3)nc2-c2nnc(N[C@@H]3N=C(c4ccccc4)c4cccc(F)c4NC3=O)o2)cn1] | 567.2 |

TABLE 8-continued

| Example# | Structure | ESI-MS [M + H]+ |
|---|---|---|
| 61 | 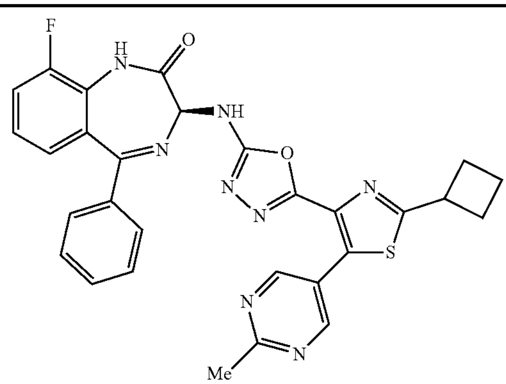 | 567.2 |
| 62 | 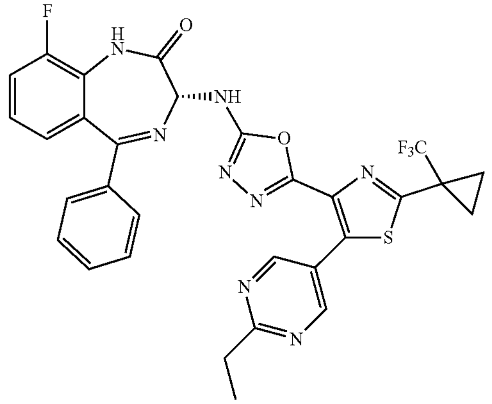 [SMILES: CCc1ncc(-c2sc(C3(C(F)(F)F)CC3)nc2-c2nnc(N[C@@H]3N=C(c4ccccc4)c4cccc(F)c4NC3=O)o2)cn1] | 635.2 |
| 63 | 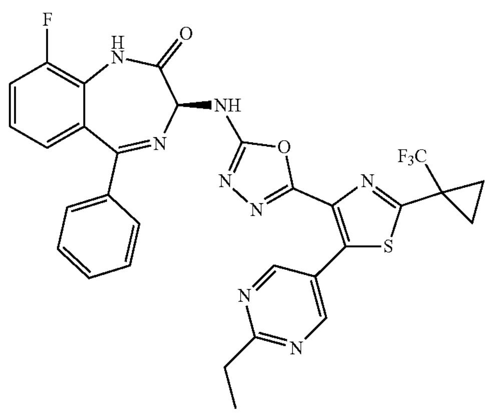 [SMILES: CCc1ncc(-c2sc(C3(C(F)(F)F)CC3)nc2-c2nnc(N[C@H]3N=C(c4ccccc4)c4cccc(F)c4NC3=O)o2)cn1] | 635.2 |
| 64 | 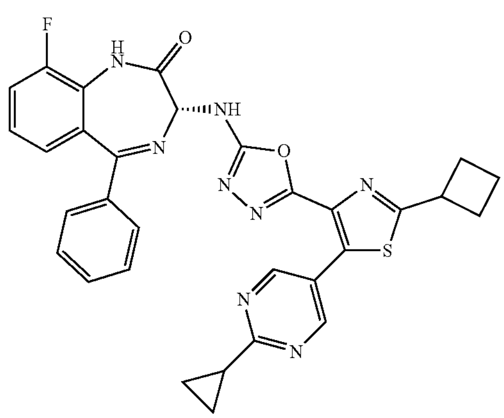 [SMILES: O=C1Nc2c(F)cccc2C(c2ccccc2)=N[C@H]1Nc1nnc(-c2nc(C3CCC3)sc2-c2cnc(C3CC3)nc2)o1] | 593.3 |

TABLE 8-continued
| Example# | Structure | ESI-MS [M + H]+ |
|---|---|---|
| 65 | 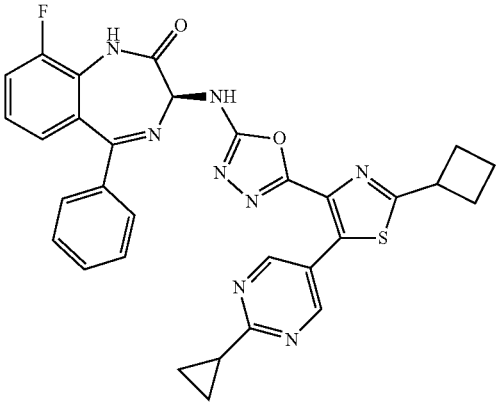 [SMILES: O=C1Nc2c(F)cccc2C(c2ccccc2)=N[C@@H]1Nc1nnc(-c2nc(C3CCC3)sc2-c2cnc(C3CC3)nc2)o1] | 593.3 |
| 66 | 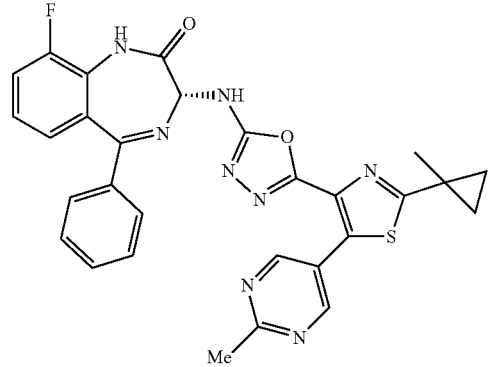 [SMILES: Cc1ncc(-c2sc(C3(C)CC3)nc2-c2nnc(N[C@@H]3N=C(c4ccccc4)c4cccc(F)c4NC3=O)o2)cn1] | 567.1 |
| 67 | 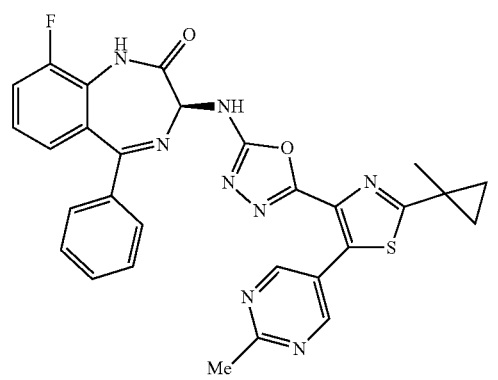 [SMILES: Cc1ncc(-c2sc(C3(C)CC3)nc2-c2nnc(N[C@H]3N=C(c4ccccc4)c4cccc(F)c4NC3=O)o2)cn1] | 567.1 |
| 68 | 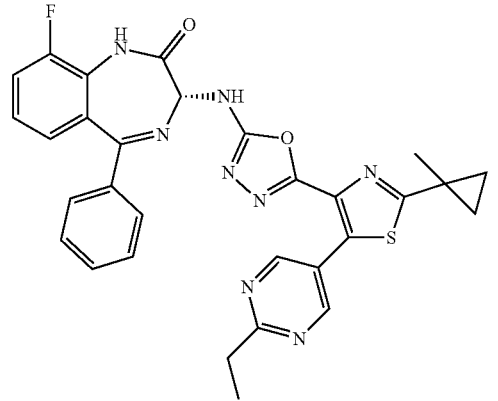 [SMILES: CCc1ncc(-c2sc(C3(C)CC3)nc2-c2nnc(N[C@@H]3N=C(c4ccccc4)c4cccc(F)c4NC3=O)o2)cn1] | 581.2 |

TABLE 8-continued

| Example# | Structure | ESI-MS [M + H]+ |
|---|---|---|
| 69 | 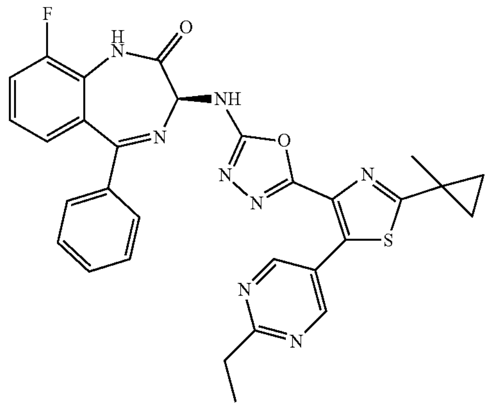 [SMILES: CCc1ncc(-c2sc(C3(C)CC3)nc2-c2nnc(N[C@H]3N=C(c4ccccc4)c4cccc(F)c4NC3=O)o2)cn1] | 581.2 |
| 70 | 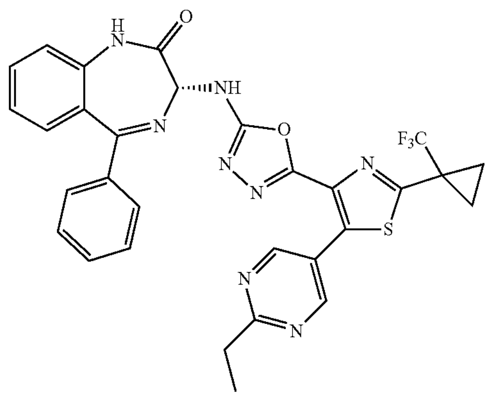 [SMILES: CCc1ncc(-c2sc(C3(C(F)(F)F)CC3)nc2-c2nnc(N[C@@H]3N=C(c4ccccc4)c4ccccc4NC3=O)o2)cn1] | 617.2 |
| 71 | 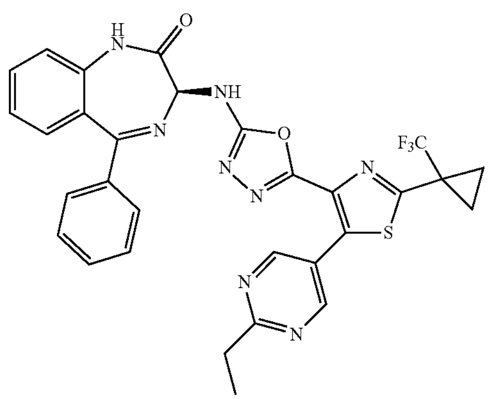 [SMILES: CCc1ncc(-c2sc(C3(C(F)(F)F)CC3)nc2-c2nnc(N[C@H]3N=C(c4ccccc4)c4ccccc4NC3=O)o2)cn1] | 617.2 |
| 72 | 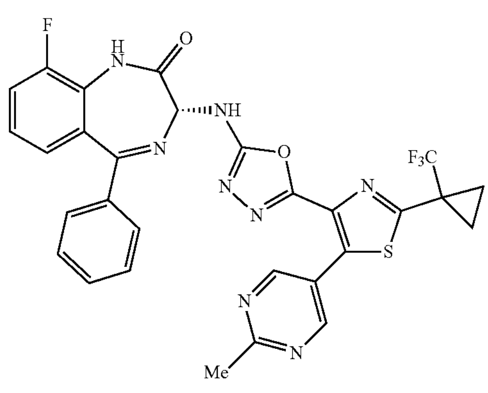 [SMILES: Cc1ncc(-c2sc(C3(C(F)(F)F)CC3)nc2-c2nnc(N[C@@H]3N=C(c4ccccc4)c4cccc(F)c4NC3=O)o2)cn1] | 621.3 |

TABLE 8-continued

| Example# | Structure | ESI-MS [M + H]+ |
|---|---|---|
| 73 | 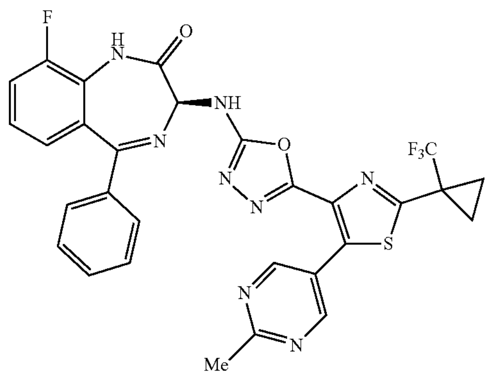 [SMILES: Cc1ncc(-c2sc(C3(C(F)(F)F)CC3)nc2-c2nnc(N[C@H]3N=C(c4ccccc4)c4cccc(F)c4NC3=O)o2)cn1] | 621.3 |
| 74 | 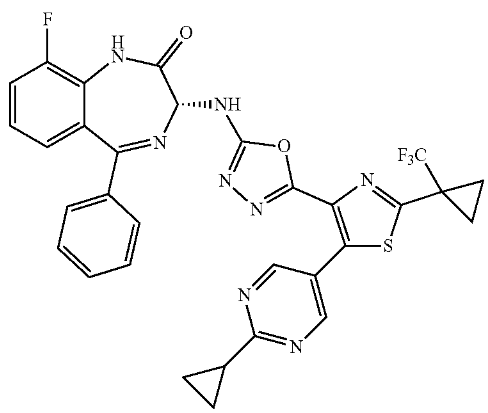 [SMILES: O=C1Nc2c(F)cccc2C(c2ccccc2)=N[C@H]1Nc1nnc(-c2nc(C3(C(F)(F)F)CC3)sc2-c2cnc(C3CC3)nc2)o1] | 647.1 |
| 75 | 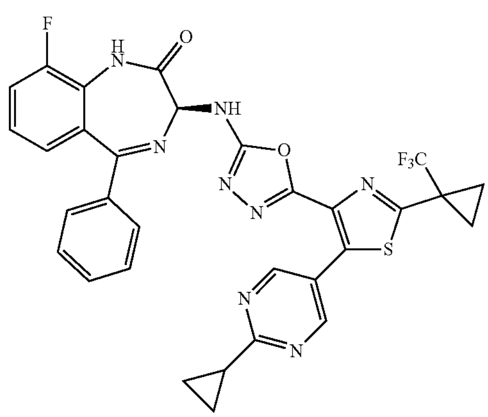 [SMILES: O=C1Nc2c(F)cccc2C(c2ccccc2)=N[C@@H]1Nc1nnc(-c2nc(C3(C(F)(F)F)CC3)sc2-c2cnc(C3CC3)nc2)o1] | 647.1 |

Example 96

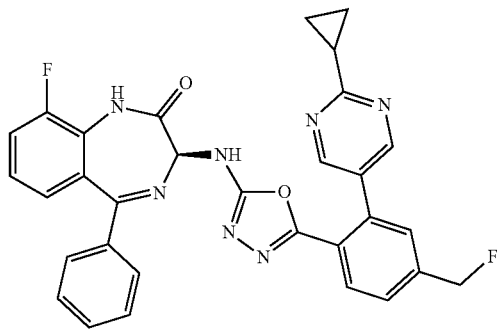 [SMILES: O=C1Nc2c(F)cccc2C(c2ccccc2)=N[C@@H]1Nc1nnc(-c2ccc(CF)cc2-c2cnc(C3CC3)nc2)o1]

Example 96 Step a

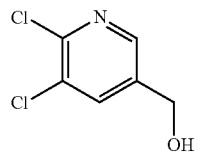

A solution of methyl 5,6-dichloropyridine-3-carboxylate (7.00 g, 33.97 mmol) and diisobutylaluminium hydride (68 mL, 101.9 mmol) in tetrahydrofuran (100 mL) was stirred for 40 min at −20° C. The reaction was quenched with 1N HCl (aq.) at 0° C. The resulting mixture was extracted with EtOAc. The combined organic layers were washed with brine, dried over anhydrous Na$_2$SO$_4$. After filtration, the filtrate was concentrated under reduced pressure. The residue was purified by silica gel column chromatography, eluted with petroleum ether/EtOAc (10:1) to afford desired product (5.8 g, 95.9%) as a white solid. ESI-MS m/z: 178.00 [M+H]$^+$.

Example 96 Step b

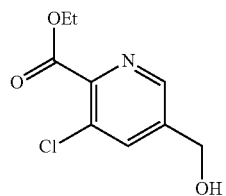 [SMILES: CCOC(=O)c1ncc(CO)cc1Cl]

A solution of the compound from step a (2.00 g, 11.23 mmol), (acetyloxy)palladio acetate (0.25 g, 1.12 mmol), sodium acetate (1.84 g, 22.47 mmol) and Pd(dppf)Cl$_2$ (0.82 g, 1.12 mmol) in ethyl alcohol (20 mL, 0.43 mmol) was stirred for 3 h at 80° C. under 30 atm atmosphere. The resulting mixture was concentrated under reduced pressure. The residue was purified by silica gel column chromatography, eluted with petroleum ether/EtOAc (1:1) to afford desired product (1.85 g, 76.36%) as a yellow solid. ESI-MS m/z: 216.05 [M+H]$^+$.

Example 96 Step c

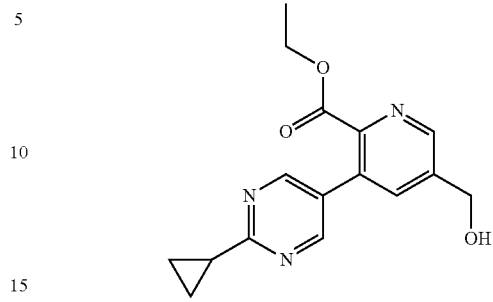

A solution of compound from step b (1.80 g, 8.34 mmol), 2-cyclopropyl-5-(4,4,5,5-tetramethyl-1,3,2-dioxaborolan-2-yl)pyrimidine (2.47 g, 10.00 mmol), NaHCO$_3$ (1.40 g, 0.017 mol) and Pd(dppf)Cl$_2$ (0.61 g, 0.001 mol) in dioxane (40 mL) and water (10 mL) was stirred for 4 h at 100° C. under nitrogen atmosphere. The resulting mixture was extracted with EtOAc. The combined organic layers were washed with H$_2$O, the aqueous phase was concentrated under reduced pressure. The crude product was purified by reverse phase C18 column chromatography, eluted with MeCN/H$_2$O to afford desired product (860 mg, 38.0%) as a light brown solid. ESI-MS m/z: 300.15 [M+H]$^+$.

Example 96 Step d

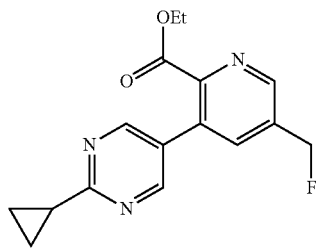 [SMILES: CCOC(=O)c1ncc(CF)cc1-c1cnc(C2CC2)nc1]

A solution of compound from step c (850 mg, 3.13 mmol) and diethylaminosulfur trifluoride (1.51 g, 9.40 mmol) in CH$_2$Cl$_2$ (20 mL) was stirred for 1 h at room temperature. The reaction was quenched with MeOH at room temperature. The resulting mixture was extracted with CH$_2$Cl$_2$. The combined organic layers were washed with H$_2$O, dried over anhydrous Na$_2$SO$_4$. After filtration, the filtrate was concentrated under reduced pressure to afford desired product (700 mg, 77.8%) as a yellow crude solid. ESI-MS m/z: 302.10 [M+H]$^+$.

Example 96 Step e

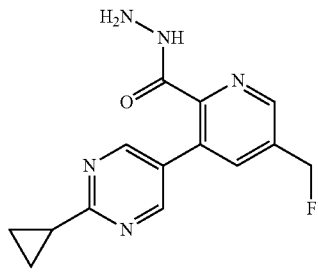 [SMILES: NNC(=O)c1ncc(CF)cc1-c1cnc(C2CC2)nc1]

A solution of compound from step d (690 mg) and NH₂NH₂·H₂O (2 mL) in ethyl alcohol (10 mL) was stirred for 2 h at room temperature. The resulting mixture was extracted with EtOAc. The combined organic layers were washed with brine, dried over anhydrous Na₂SO₄. After filtration, the filtrate was concentrated under reduced pressure. The residue was purified by silica gel column chromatography, eluted with MeOH/DCM to afford desired product (350 mg, 50.7%) as a brown solid. ESI-MS m/z: 288.20 [M+H]⁺.

Example 96 Step f

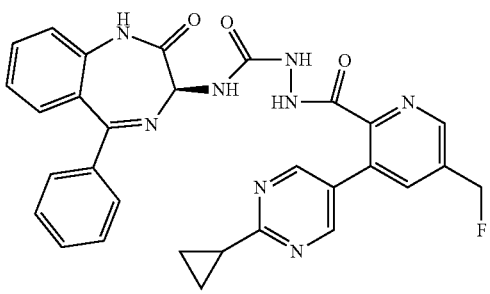 [SMILES: O=C(NNC(=O)c1ncc(CF)cc1-c1cnc(C2CC2)nc1)N[C@H]1N=C(c2ccccc2)c2ccccc2NC1=O]

A solution of compound from step e (200 mg, 0.69 mmol) and (S)—N-(2-oxo-5-phenyl-2,3-dihydro-1H-benzo[e][1,4]diazepin-3-yl)-1H-imidazole-1-carboxamide (step c from example 23, 288 mg, 0.83 mmol) in DMSO (10 mL) was stirred overnight at room temperature. The crude product was purified by reverse phase C18 column chromatography, eluted with MeCN/H₂O to afford desired product (370 mg, 94.1%) as a yellow solid. ESI-MS m/z: 565.20 [M+H]⁺.

Example 96 Step g

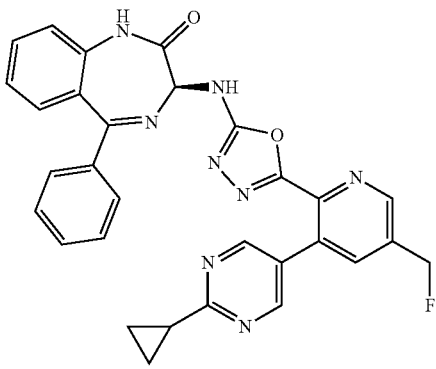 [SMILES: O=C1Nc2ccccc2C(c2ccccc2)=N[C@@H]1Nc1nnc(-c2ncc(CF)cc2-c2cnc(C3CC3)nc2)o1]

A solution of compound from step f (350 mg, 0.62 mmol), triethylamine (188 mg, 1.86 mmol) and p-toluenesulfonyl chloride (177 mg, 0.93 mmol) in DCM (20 mL) was stirred for 3 h at 20° C. The resulting mixture was concentrated under vacuum. The crude product was purified by reverse phase C18 column chromatography, eluted with MeCN/H₂O to afford desired product (200 mg, 59.0%) as a light yellow solid. ESI-MS m/z: 547.15 [M+H]⁺.

Example 97

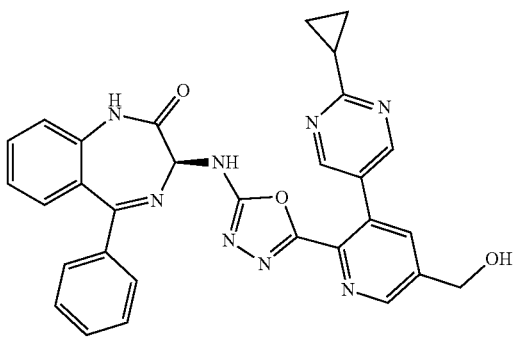 [SMILES: O=C1Nc2ccccc2C(c2ccccc2)=N[C@@H]1Nc1nnc(-c2ncc(CO)cc2-c2cnc(C3CC3)nc2)o1]

Example 97 Step a

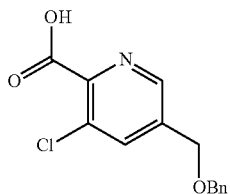 [SMILES: O=C(O)c1ncc(COCc2ccccc2)cc1Cl]

A solution of ethyl 3-chloro-5-(hydroxymethyl)picolinate compound (a compound from example 96, step b, 3.20 g, 14.84 mmol) and NaH (1.07 g, 44.52 mmol) in dimethylformamide (20 mL) was stirred for 30 min at 0° C., then benzyl bromide (3.81 g, 22.26 mmol) was added. It was warmed to room temperature and stirred for 1 h. The reaction was quenched with 1N HCl (aq.) at 0° C. The resulting mixture was extracted with EtOAc. The combined organic layers were washed with brine, dried over anhydrous Na₂SO₄. After filtration, the filtrate was concentrated under reduced pressure. The residue was purified by silica gel column chromatography, eluted with petroleum ether/EtOAc (1:1) to afford desired product (1.2 g, 29.1%) as a yellow solid. ESI-MS m/z: 278.05 [M+H]⁺.

Example 97 Step b

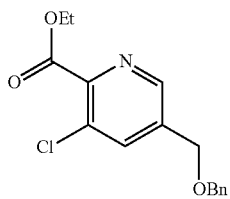 [SMILES: CCOC(=O)c1ncc(COCc2ccccc2)cc1Cl]

A solution of compound from step a (1.10 g, 3.96 mmol), ethyl iodide (0.80 g, 5.14 mmol) and Cs₂CO₃ (2.59 g, 7.92 mmol) in dimethylformamide (30 mL) was stirred for 2 h at room temperature. The resulting mixture was extracted with EtOAc. The combined organic layers were washed with brine, dried over anhydrous Na₂SO₄. After filtration, the filtrate was concentrated under reduced pressure. The residue was purified by silica gel column chromatography, eluted with petroleum ether/EtOAc (1:1) to afford desired product (950 mg, 78.4%) as a yellow solid. ESI-MS m/z: 306.10 [M+H]+.

Example 97 Step c

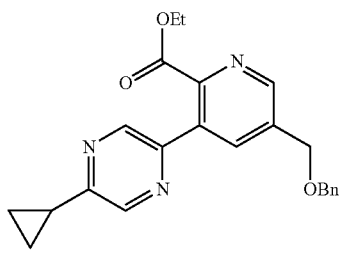 [SMILES: CCOC(=O)c1ncc(COCc2ccccc2)cc1-c1cnc(C2CC2)cn1]

A solution of compound from step b (930 mg, 3.04 mmol), 2-cyclopropyl-5-(4,4,5,5-tetramethyl-1,3,2-dioxaborolan-2-yl)pyrimidine (973 mg, 3.95 mmol), NaHCO₃ (511 mg, 6.08 mmol) and Pd(dppf)Cl₂ (222 mg, 0.30 mmol) in water (2.50 mL) and dioxane (10 mL) was stirred for 2 h at 100° C. under nitrogen atmosphere. The resulting mixture was concentrated under reduced pressure. The residue was purified by silica gel column chromatography, eluted with petroleum ether/EtOAc (1:1) to afford desired product (800 mg, 67.5%) as a yellow oil. ESI-MS m/z: 390.20 [M+H]+.

Example 97 Step d

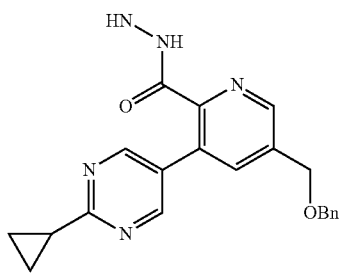 [SMILES: NNC(=O)c1ncc(COCc2ccccc2)cc1-c1cnc(C2CC2)nc1]

A solution of compound from step c (780 mg) and NH₂NH₂·H₂O (3 mL) in ethyl alcohol (10 mL) was stirred for 4 h at room temperature. The resulting mixture was concentrated under reduced pressure. The residue was purified by silica gel column chromatography, eluted with MeCN/water to afford desired product (420 mg, 55.9%) as a yellow solid. ESI-MS m/z: 376.20 [M+H]+.

Example 97 Step e

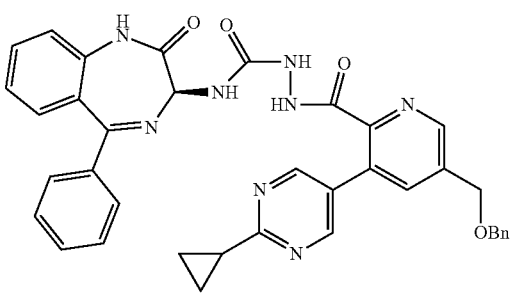 [SMILES: O=C(NNC(=O)c1ncc(COCc2ccccc2)cc1-c1cnc(C2CC2)nc1)N[C@H]1N=C(c2ccccc2)c2ccccc2NC1=O]

A solution of compound from step d (200 mg, 0.53 mmol) and (S)—N-(2-oxo-5-phenyl-2,3-dihydro-1H-benzo[e][1,4]diazepin-3-yl)-1H-imidazole-1-carboxamide (step c from example 23, 202 mg, 0.58 mmol) in DMSO (1 mL) was stirred overnight at room temperature. The residue was purified by silica gel column chromatography, eluted with MeCN/H₂O to afford desired product (320 mg, 92.1%) as a yellow solid. ESI-MS m/z: 653.20 [M+H]+.

Example 97 Step f

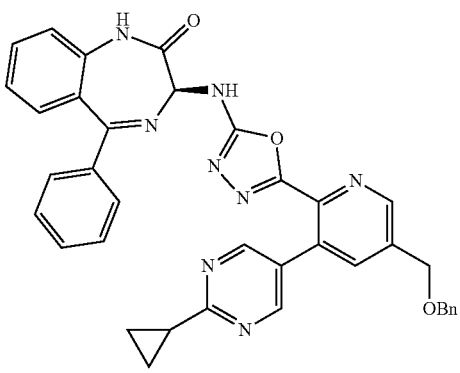 [SMILES: O=C1Nc2ccccc2C(c2ccccc2)=N[C@@H]1Nc1nnc(-c2ncc(COCc3ccccc3)cc2-c2cnc(C3CC3)nc2)o1]

A solution of compound from step e (320 mg, 0.49 mmol) and TEA (148 mg, 1.47 mmol) in DCM (10 mL) was stirred at 0° C., then p-toluenesulfonyl chloride (140 mg, 0.73 mmol) was added, it was stirred for 3 h at room temperature. The resulting mixture was concentrated under reduced pressure. The residue was purified by silica gel column chromatography, eluted with MeCN/H₂O to afford desired product (270 mg, 86.8%) as a yellow solid. ESI-MS m/z: 635.20 [M+H]+.

Example 97 Step g

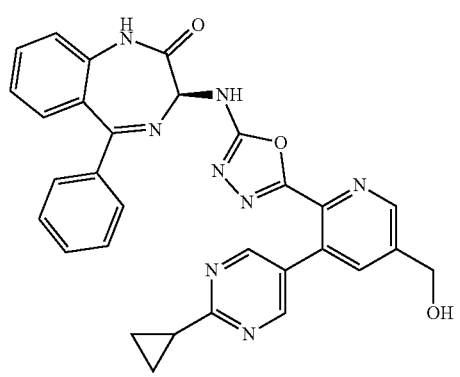 [SMILES: O=C1Nc2ccccc2C(c2ccccc2)=N[C@@H]1Nc1nnc(-c2ncc(CO)cc2-c2cnc(C3CC3)nc2)o1]

Into a 50 mL round-bottom flask were added the compound from step f (120 mg, 0.19 mmol) and DCM (10 mL) at room temperature. To the reaction mixture was filled with nitrogen, boron trichloride (1.5 mL) was added and stirred for 1 h at room temperature. The reaction was quenched with sat. NaHCO₃ (aq.) at room temperature, extracted with EtOAc, purified by Prep-HPLC to afford the product as a white solid. ESI-MS m/z: 545.10 [M+H]+.

Example 98

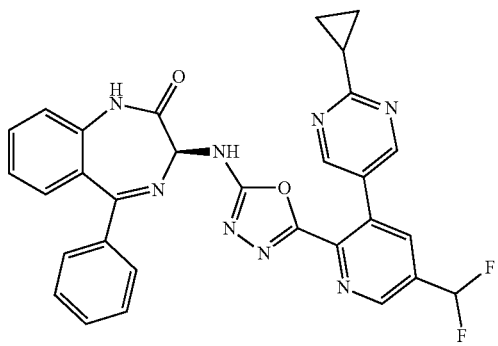 [SMILES: O=C1Nc2ccccc2C(c2ccccc2)=N[C@@H]1Nc1nnc(-c2ncc(C(F)F)cc2-c2cnc(C3CC3)nc2)o1]

Example 98 Step a

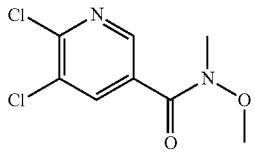

A solution of 5,6-dichloropyridine-3-carboxylic acid (12.00 g, 62.50 mmol), hydroxybenzotriazole (16.89 g, 125.00 mmol), EDC.HCl (23.96 g, 125.00 mmol) and TEA (18.97 g, 187.50 mmol) in DCM (250 mL) was stirred for 30 mins at 0° C., then added N,O-dimethylhydroxylamine (12.01 g, 125.00 mmol). It was stirred at room temperature for 4 h. The resulting mixture was extracted with $CH_2Cl_2$. The combined organic layers were washed with brine, dried over anhydrous $Na_2SO_4$. After filtration, the filtrate was concentrated under reduced pressure to afford desired product (14 g, 95.3%) as a yellow solid. ESI-MS m/z: 235.00 [M+H]$^+$.

Example 98 Step b

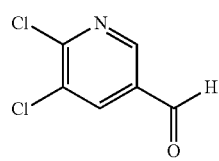

A solution of compound from step a (13.9 g, 59.1 mmol) in THF (120 mL) was stirred at 0° C., diisobutylaluminium hydride (59.0 mL, 59.1 mmol) was added, it was stirred at 0° C. for 2 h. The reaction was quenched with 1N HCl (aq.) at 0° C. The resulting mixture was extracted with ethyl acetate. The combined organic layers were washed with brine, dried over anhydrous $Na_2SO_4$. After filtration, the filtrate was concentrated under reduced pressure. The residue was purified by silica gel column chromatography, eluted with petroleum ether/EtOAc (10:1) to afford desired product (9.5 g, 91.3%) as a white solid. ESI-MS m/z: 176.00 [M+H]$^+$.

Example 98 Step c

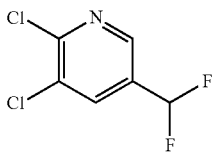 [SMILES: FC(F)c1cnc(Cl)c(Cl)c1]

A solution of compound from step b (5.10 g, 29.0 mmol) in DCM (100 mL) was stirred at −30° C., then diethylaminosulfur trifluoride (14.01 g, 86.9 mmol) was added, it was warmed to room temperature and stirred for 2 h. The reaction was quenched with sat. $NaHCO_3$ (aq.) at 0° C. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with petroleum ether/EtOAc (10:1) to afford desired product (4.8 g, 83.7%) as a brown yellow liquid. ESI-MS m/z: 198.00 [M+H]$^+$.

Example 98 Step d

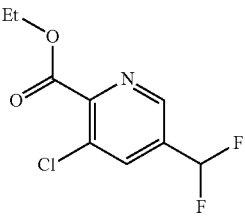 [SMILES: CCOC(=O)c1ncc(C(F)F)cc1Cl]

A solution of compound from step c (2.70 g, 13.6 mmol), sodium acetate (1.68 g, 20.45 mmol), Pd(AcO)$_2$ (0.40 g, 1.77 mmol) and Pd(dppf)Cl$_2$ (1.00 g, 1.36 mmol) in ethyl alcohol (20 mL) was stirred overnight at 80° C. under 30 atm carbon monoxide atmosphere. The resulting mixture was concentrated under reduced pressure. The residue was purified by silica gel column chromatography, eluted with petroleum ether/EtOAc (10:1) to afford desired product (3.1 g, 96.5%) as a yellow oil. ESI-MS m/z: 236.00 [M+H]$^+$.

Example 98 Step e

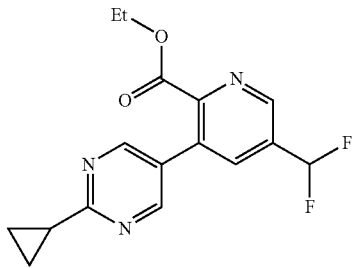 [SMILES: CCOC(=O)c1ncc(C(F)F)cc1-c1cnc(C2CC2)nc1]

A solution of compound from step d (1.50 g, 6.36 mmol), 2-cyclopropyl-5-(4,4,5,5-tetramethyl-1,3,2-dioxaborolan-2-yl)pyrimidine (1.88 g, 7.64 mmol), NaHCO$_3$ (1.07 g, 12.73 mmol) and Pd(dppf)Cl$_2$ (0.23 g, 0.31 mmol) in dioxane (80 mL) and water (20 mL) was stirred for 3 h at 80° C. under nitrogen atmosphere. The resulting mixture was concentrated under vacuum. The residue was purified by silica gel column chromatography, eluted with petroleum ether/EtOAc (10:1) to afford desired product (2.1 g, 103.3%) as a yellow crude oil. This crude ESI-MS m/z: 320.10 [M+H]⁺.

Example 98 Step f

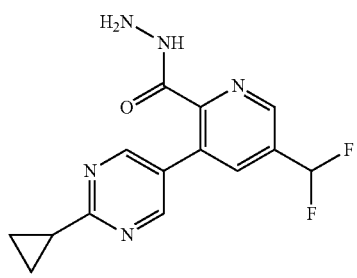 [SMILES: NNC(=O)c1ncc(C(F)F)cc1-c1cnc(C2CC2)nc1]

A solution of compound from step e (2.05 g, 6.42 mmol) in ethyl alcohol (40 mL) and NH₂NH₂·H₂O (5 mL) was stirred for 2 h at room temperature. The resulting mixture was extracted with EtOAc. The combined organic layers were washed with brine. After filtration, the filtrate was concentrated under reduced pressure. The residue was purified by silica gel column chromatography, eluted with MeCN/H₂O to afford desired product (1.02 g, 52.0%) as a light yellow solid. ESI-MS m/z: 306.10 [M+H]⁺.

Example 98 Step g

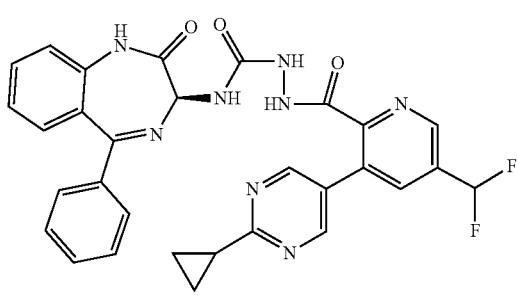 [SMILES: O=C(NNC(=O)c1ncc(C(F)F)cc1-c1cnc(C2CC2)nc1)N[C@H]1N=C(c2ccccc2)c2ccccc2NC1=O]

A solution of compound from step f (200 mg, 0.65 mmol) and (S)—N-(2-oxo-5-phenyl-2,3-dihydro-1H-benzo[e][1,4]diazepin-3-yl)-1H-imidazole-1-carboxamide (step c from example 23, 271 mg, 0.78 mmol) in dimethylformamide (10 mL) was stirred overnight at room temperature. The residue was purified by silica gel column chromatography, eluted with CH₃CN/H₂O to afford desired product (400 mg, 104.8%) as a yellow crude solid. ESI-MS m/z: 583.20 [M+H]⁺.

Example 98 Step h

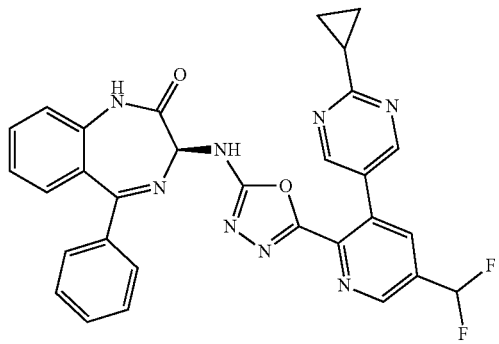 [SMILES: O=C1Nc2ccccc2C(c2ccccc2)=N[C@@H]1Nc1nnc(-c2ncc(C(F)F)cc2-c2cnc(C3CC3)nc2)o1]

A solution of compound from step g (380 mg, 0.65 mmol), TsCl (186.53 mg, 0.97 mmol) and TEA (198 mg, 1.95 mmol) in DCM (20 mL) was stirred for 3 h at 10° C. The residue was purified by silica gel column chromatography, eluted with petroleum ether/EtOAc (1:4) to afford desired product (300 mg) as a yellow solid. The crude product (300 mg) was purified by Prep-HPLC with the following conditions (MeCN/H₂O) to afford desired product (142.3 mg, 38.64%) as a white solid. ESI-MS m/z: 565.15 [M+H]⁺.

Example 99

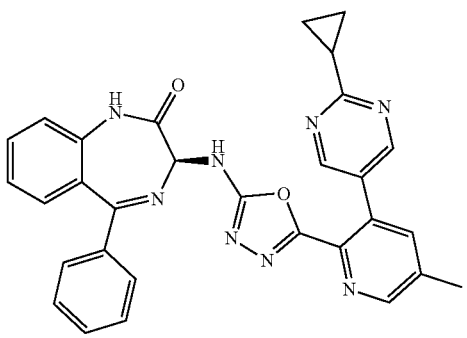 [SMILES: Cc1cnc(-c2nnc(N[C@H]3N=C(c4ccccc4)c4ccccc4NC3=O)o2)c(-c2cnc(C3CC3)nc2)c1]

Example 99 Step a

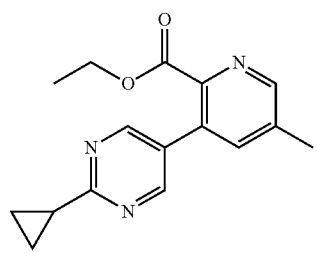 [SMILES: CCOC(=O)c1ncc(C)cc1-c1cnc(C2CC2)nc1]

To a 30 ml microwave vial was added ethyl 3-bromo-5-methylpicolinate (244 mg, 1.0 mmol), sodium bicarbonate (168 mg, 2 mmol), Pd(dppf)Cl₂·CH₂Cl₂ (83 mg, 0.1 mmol) and 2-cyclopropyl-5-(4,4,5-trimethyl-1,3,2-dioxaborolan-2- yl)pyrimidine (246 mg, 1.0 mmol) in 1,4-dioxane (4 mL) and water (1 mL). The reaction mixture was degassed using nitrogen for 5 min and then heated at 100° C. for 1 h. The reaction was added water/ethyl acetate and extracted with ethyl acetate. The combined organic layer was washed with water, dried (Na₂SO₄), concentrated, and purified by column chromatography (silica, Hexane:EtOAc=2:1) to give desired compound as light yellow solid (255 mg, 90% yield). ESI-MS m/z: 284.35 [M+H]⁺.

Example 99 Step b

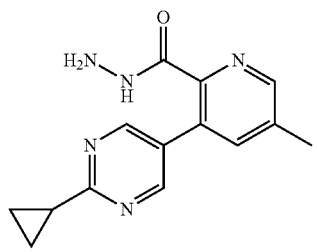 [SMILES: Cc1cnc(C(=O)NN)c(-c2cnc(C3CC3)nc2)c1]

A solution of compound from step a (283 mg, 1.0 mmol) in EtOH (1.3 mL) was added NH₂NH₂·H₂O (~50%, 0.65 mL) and the reaction was stirred at 30° C. for 2 h. The reaction mixture was then added to cold water (3 mL) and the resulting precipitate was collected by filtration to give the desired compound (135 mg, 50%) as a white solid, which was used directly in the next step without further purification. ESI-MS m/z: 270.15 [M+H]⁺.

Example 99 Step c

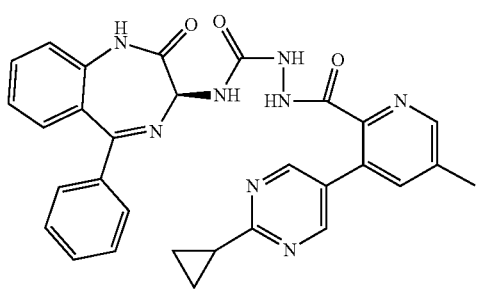 [SMILES: Cc1cnc(C(=O)NNC(=O)N[C@H]2N=C(c3ccccc3)c3ccccc3NC2=O)c(-c2cnc(C3CC3)nc2)c1]

A solution of compound from step b (270 mg, 1.0 mmol) and (S)—N-(2-oxo-5-phenyl-2,3-dihydro-1H-benzo[e][1,4] diazepin-3-yl)-1H-imidazole-1-carboxamide (step c from example 23, 269 mg, 1.0 mmol) in a 4 mL vial was added DMSO (1 mL). The reaction mixture was stirred at room temperature for 48 h and then added to ice-cold water (10 mL) in 25 mL round-bottomed flask with stirring. The residue was rinsed with DMSO (1 mL) and added into the 25 mL round-bottomed flask. A pale yellow solid was immediately formed and stirring continued for additional 30 min before filtered through a fritted funnel and the solid was washed with water. The wet product was dried under high vacuum to give the desired product as a pale yellow solid (540 mg, 99%) that was used without further purification. ESI-MS m/z: 547.35 [M+H]⁺.

Example 99 Step d

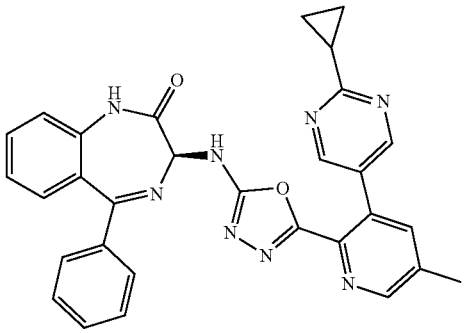 [SMILES: Cc1cnc(-c2nnc(N[C@H]3N=C(c4ccccc4)c4ccccc4NC3=O)o2)c(-c2cnc(C3CC3)nc2)c1]

(S)-2-(3-(2-cyclopropylpyrimidin-5-yl)-5-methylpi-colinoyl)-N-(2-oxo-5-phenyl-2,3-dihydro-1H-benzo[e][1,4] diazepin-3-yl)hydrazine-1-carboxamide (437 mg, 0.8 mmol, step c) in DCM (8 mL) in a 25 mL round bottom flask was cooled at 0° C. Triethylamine (304 μl, 2.18 mmol) was added to the reaction dropwise followed by addition of TsCl (250 mg, 1.31 mmol). The reaction mixture was stirred at 0° C. for 1 h and slowly warmed to room temperature and stirred for additional 3 h. The reaction mixture was quenched with water and saturated sodium bicarbonate solution. The organic layer was separated and washed with brine. The organic layer was dried (Na₂SO₄), concentrated, and purified by column chromatography (silica, Hexane: Acetone=1:1) to give the title compound as light yellow solid (127 mg, 30% yield). ESI-MS m/z: 529.20 [M+H]⁺.

Examples 78-95 in Table 10 are prepared by using the procedures similar to those described above.

TABLE 10

| Example# | Structure |
| --- | --- |
| 78 | 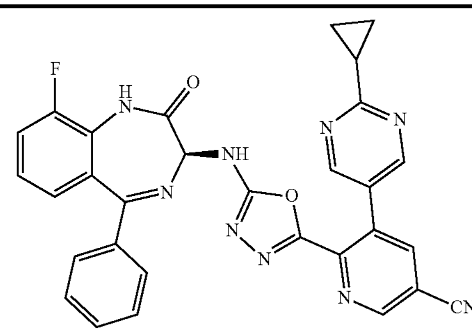 |
| 79 | 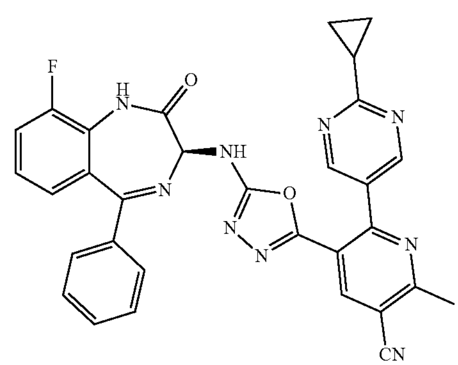 [SMILES: Cc1nc(-c2cnc(C3CC3)nc2)c(-c2nnc(N[C@H]3N=C(c4ccccc4)c4cccc(F)c4NC3=O)o2)cc1C#N] |

TABLE 10-continued
| Example# | Structure |
|---|---|
| 80 | 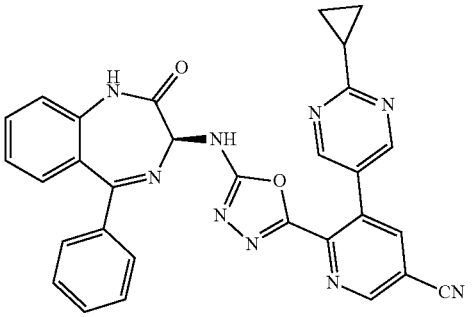 [SMILES: N#Cc1cnc(-c2nnc(N[C@H]3N=C(c4ccccc4)c4ccccc4NC3=O)o2)c(-c2cnc(C3CC3)nc2)c1] |
| 81 | 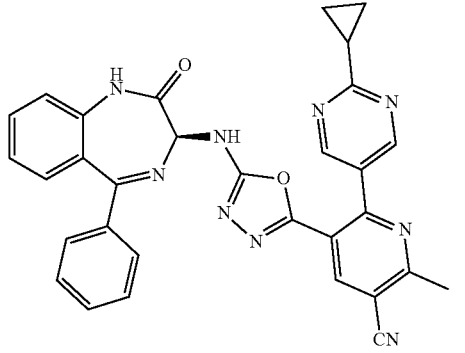 [SMILES: Cc1nc(-c2cnc(C3CC3)nc2)c(-c2nnc(N[C@H]3N=C(c4ccccc4)c4ccccc4NC3=O)o2)cc1C#N] |
| 82 | 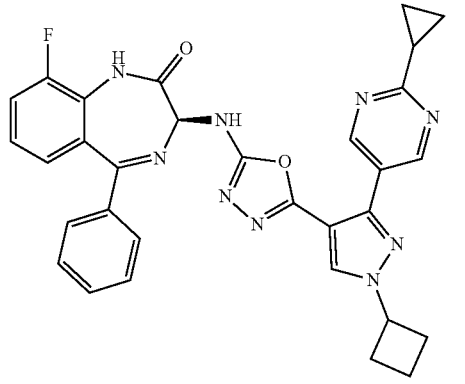 [SMILES: O=C1Nc2c(F)cccc2C(c2ccccc2)=N[C@@H]1Nc1nnc(-c2cn(C3CCC3)nc2-c2cnc(C3CC3)nc2)o1] |
| 83 | 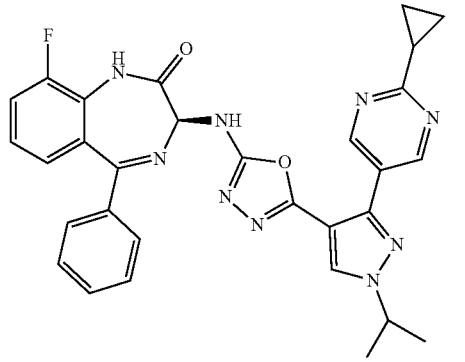 [SMILES: CC(C)n1cc(-c2nnc(N[C@H]3N=C(c4ccccc4)c4cccc(F)c4NC3=O)o2)c(-c2cnc(C3CC3)nc2)n1] |
| 84 | 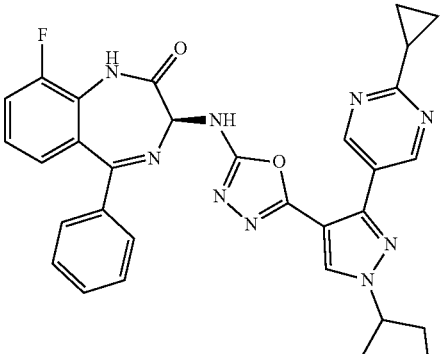 |
| 85 | 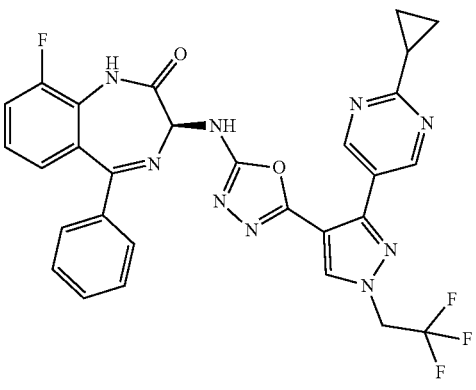 [SMILES: O=C1Nc2c(F)cccc2C(c2ccccc2)=N[C@@H]1Nc1nnc(-c2cn(CC(F)(F)F)nc2-c2cnc(C3CC3)nc2)o1] |
| 86 | 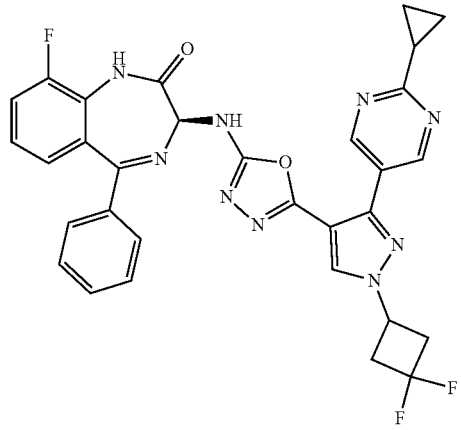 [SMILES: O=C1Nc2c(F)cccc2C(c2ccccc2)=N[C@@H]1Nc1nnc(-c2cn(C3CC(F)(F)C3)nc2-c2cnc(C3CC3)nc2)o1] |
| 87 | 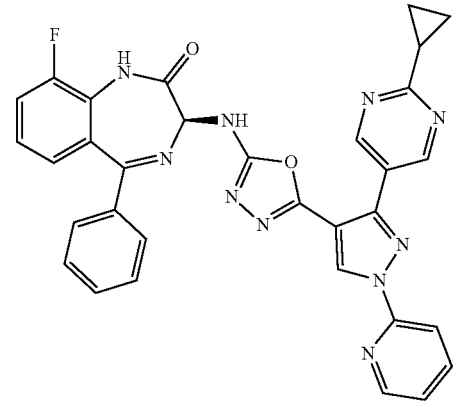 [SMILES: O=C1Nc2c(F)cccc2C(c2ccccc2)=N[C@@H]1Nc1nnc(-c2cn(-c3ccccn3)nc2-c2cnc(C3CC3)nc2)o1] |

TABLE 10-continued
| Example# | Structure |
|---|---|
| 88 | 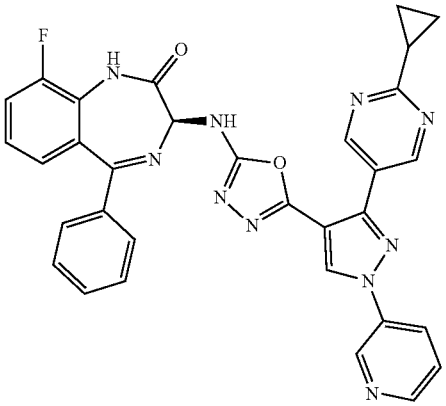 [SMILES: O=C1Nc2c(F)cccc2C(c2ccccc2)=N[C@@H]1Nc1nnc(-c2cn(-c3cccnc3)nc2-c2cnc(C3CC3)nc2)o1] |
| 89 | 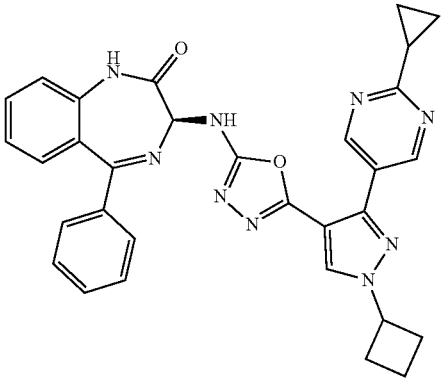 [SMILES: O=C1Nc2ccccc2C(c2ccccc2)=N[C@@H]1Nc1nnc(-c2cn(C3CCC3)nc2-c2cnc(C3CC3)nc2)o1] |
| 90 | 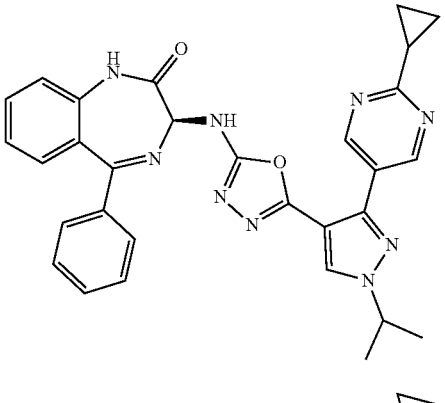 |
| 91 | 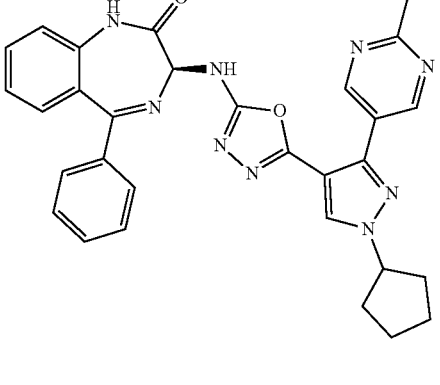 |
| 92 | 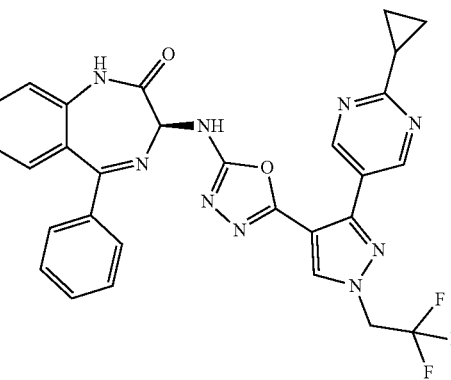 |
| 93 | 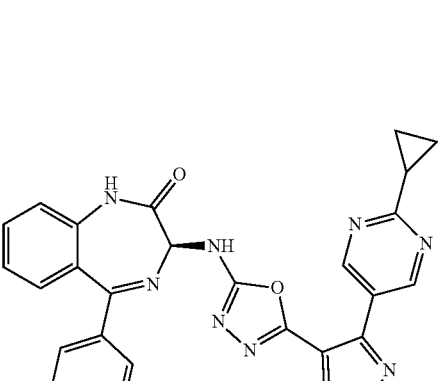 |
| 94 | 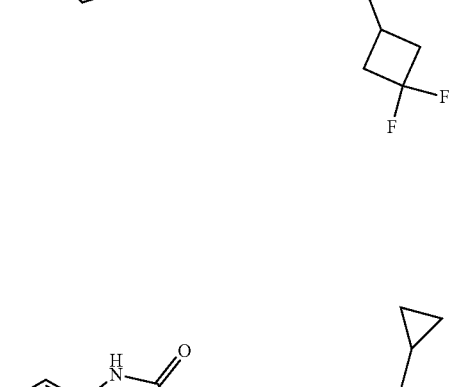 |

TABLE 10-continued

| Example# | Structure |
|---|---|
| 95 | (structure shown) |

Assays

Methods for RSV-A Assay

Hep-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 µL. Viral stock is then added to the wells at a multiplicity of infection (MOI) of 0.1 in a volume of 25 µL, bringing the total volume of each well to 100 µL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 µL of growth media containing an equal quantity of sucrose as those wells receiving the viral stock in order to keep consistent in media and volume conditions. The outer wells of the plate are filled with 125 µL of moat media (DMEM, 1% Penn/Strep) to act as a thermal and evaporative moat around the test wells. Following a 5-day incubation period, the plates are read using ATPlite (50 µL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 µL of viral stock for 25 µL of growth media. These data are used to calculate the $EC_{50}$ and $CC_{50}$ of each compound (Table 11). $EC_{50}$ ranges are as follows: A<0.4 µM; B 0.4-0.8 µM; C>0.8 µM.

TABLE 11

Summary of Activities for RSV-A

| Example | Human RSV-A ("Long" strain) $EC_{50}$ |
|---|---|
| 1 | A |
| 2 | C |
| 3 | B |
| 4 | C |
| 5 | C |
| 6 | A |
| 7 | A |
| 8 | A |
| 9 | C |
| 10 | C |
| 11 | C |
| 12 | C |
| 13 | B |
| 14 | C |
| 15 | C |
| 16 | B |
| 17 | C |
| 18 | B |
| 19 | C |
| 20 | B |
| 21 | B |
| 22 | B |
| 23 | C |
| 24 | A |
| 25 | A |
| 26 | A |
| 27 | A |
| 28 | A |
| 29 | A |
| 30 | — |
| 31 | — |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | B |
| 50 | A |
| 51 | B |
| 52 | A |
| 53 | B |
| 54 | A |
| 55 | C |
| 56 | A |
| 57 | A |
| 58 | A |
| 59 | A |
| 60 | A |
| 61 | A |
| 62 | B |
| 63 | A |
| 64 | C |
| 65 | A |
| 66 | B |
| 67 | A |
| 68 | A |
| 69 | A |
| 70 | C |

TABLE 11-continued

Summary of Activities for RSV-A

| Example | Human RSV-A ("Long" strain) $EC_{50}$ |
|---|---|
| 71 | A |
| 72 | C |
| 73 | A |
| 74 | C |
| 75 | A |
| 76 | A |
| 77 | A |
| 96 | A |
| 97 | A |
| 98 | A |
| 99 | A |

Methods for RSV-B Assay

Hep-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype B, strain 9320. Flasks were inoculated with RSV-B and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 5-fold viral dilutions across a 96-well plate, cultured for 4 days. Viral stock titers were also quantified by a plaque forming unit assay, as described elsewhere.

The assay is run as follows: A549 cells (originally derived through explant culture from a 58 year old male's carcinomatous lung tissue) are seeded into the inner 60 wells of a 96-well plate at 3,000 cells per well in a volume of 50 μL using A549 growth media (F-12K Media, 1% Penn/Strep, 1% nonessential amino acids, 10% heat-inactivated FBS). 2-fold serial dilutions of control and test compounds are added to the wells in duplicate in a total volume of 25 μL. Viral stock is then added to the wells at a multiplicity of infection (MOI) of 0.5 in a volume of 25 μL, bringing the total volume of each well to 100 μL. The MOI is calculated using the PFU/mL, or TCID50 if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 μL of growth media containing an equal quantity of sucrose as those wells receiving the viral stock in order to keep consistent in media and volume conditions. The outer wells of the plate are filled with 125 μL of moat media (DMEM, 1% Penn/Strep) to act as a thermal and evaporative moat around the test wells. 6 days post infection, the plates are read using qPCR or ATP lite (50 μL added per well), which quantifies the amount of ATP (a measure of cell health) present in each well. Assay plates treated with APTlite are read using the Envision luminometer. These data are used to calculate the $EC_{50}$ of each compound (Table 11). $EC_{50}$ ranges are as follows: A<0.4 μM; B 0.4-0.8 μM; C>0.8 μM.

TABLE 11

Summary of Activities for RSV-B

| Example | Human RSV-B $EC_{50}$ |
|---|---|
| 1 | A |
| 2 | C |
| 3 | B |
| 4 | — |
| 5 | — |
| 6 | — |
| 7 | A |
| 8 | A |
| 9 | C |
| 10 | C |
| 11 | B |
| 12 | C |
| 13 | A |
| 14 | C |
| 15 | A |
| 16 | A |
| 17 | C |
| 18 | A |
| 19 | B |
| 20 | A |
| 21 | A |
| 22 | A |
| 23 | A |
| 24 | A |
| 25 | A |
| 26 | A |
| 27 | A |
| 28 | A |
| 29 | A |
| 30 | — |
| 31 | — |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | C |
| 71 | A |
| 72 | A |
| 73 | A |
| 74 | A |
| 75 | A |

TABLE 11-continued

Summary of Activities for RSV-B

| Example | Human RSV-B EC$_{50}$ |
|---|---|
| 76 | A |
| 77 | A |
| 96 | A |
| 97 | A |
| 98 | A |
| 99 | A |

While this invention has been particularly shown and described with references to preferred embodiments thereof, it will be understood by those skilled in the art that various changes in form and details may be made therein without departing from the scope of the invention encompassed by the appended.

What is claimed:

1. A compound represented by Formula (I):

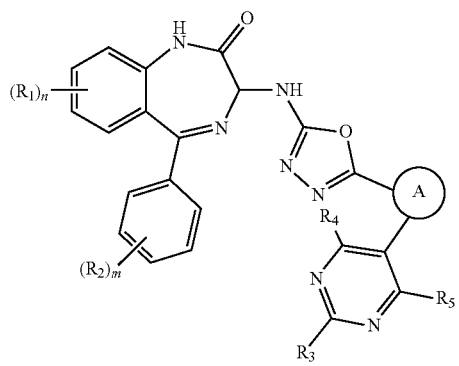

(I)

or a pharmaceutically acceptable salt thereof, wherein:
A is optionally substituted heteroaryl;
n is 0 or 1;
$R_1$ is halogen;
$R_3$ is optionally substituted —$C_1$-$C_8$ alkyl or optionally substituted $C_3$-$C_8$-cycloalkyl; and
$R_4$ and $R_5$ are each hydrogen.

2. The compound of claim 1, wherein the compound is represented by Formula (II-1),

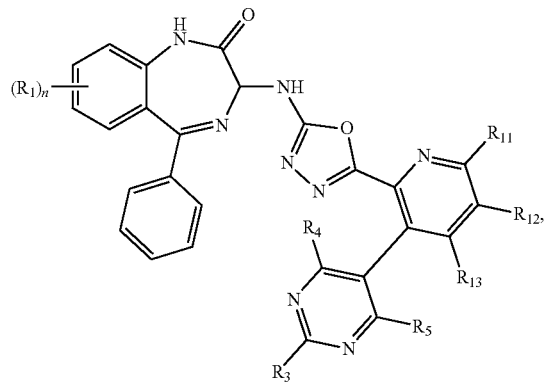

(II-1)

a pharmaceutically acceptable salt thereof, wherein
$R_1$ is fluorine;
$R_{11}$ and $R_{13}$ are hydrogen; and
$R_{12}$ is optionally substituted $C_1$-$C_8$-alkyl or optionally substituted $C_3$-$C_8$-cycloalkyl.

3. The compound of claim 1, wherein the compound is represented by Formula (VIIIb-1),

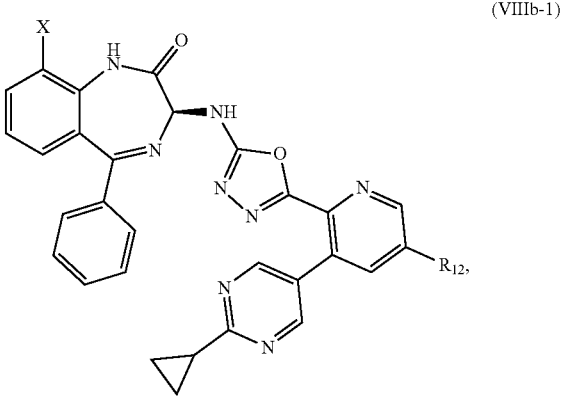

(VIIIb-1)

or a pharmaceutically acceptable salt thereof, wherein
X is hydrogen or fluorine; and
$R_{12}$ is methyl, ethyl, trifluoromethyl or cyclopropyl.

4. The compound of claim 1 having the structure

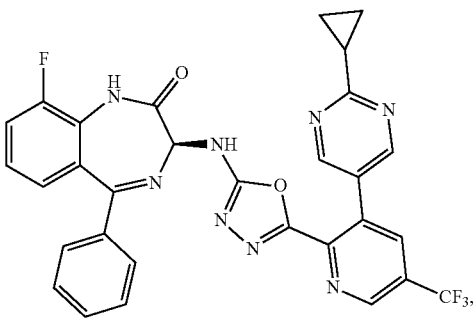 [SMILES: O=C1Nc2c(F)cccc2C(c2ccccc2)=N[C@@H]1Nc1nnc(-c2ncc(C(F)(F)F)cc2-c2cnc(C3CC3)nc2)o1]

or a pharmaceutically acceptable salt thereof.

5. The compound of claim 1 having the structure

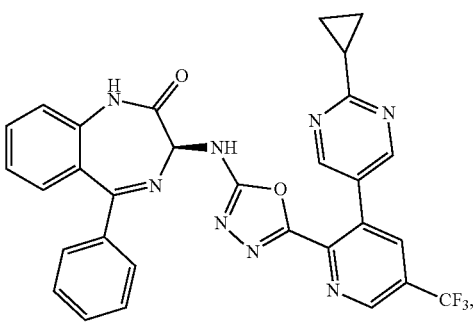 [SMILES: O=C1Nc2ccccc2C(c2ccccc2)=N[C@@H]1Nc1nnc(-c2ncc(C(F)(F)F)cc2-c2cnc(C3CC3)nc2)o1]

or a pharmaceutically acceptable salt thereof.

6. The compound of claim 1 having the structure

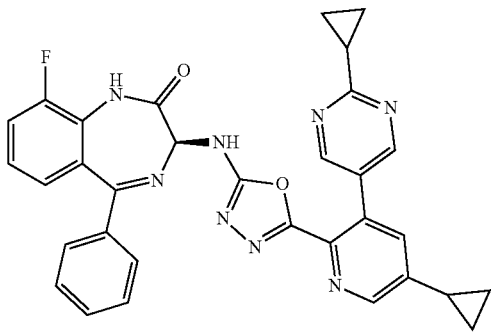 [SMILES: O=C1Nc2c(F)cccc2C(c2ccccc2)=N[C@@H]1Nc1nnc(-c2ncc(C3CC3)cc2-c2cnc(C3CC3)nc2)o1]

or a pharmaceutically acceptable salt thereof.

7. The compound of claim 1 having the structure

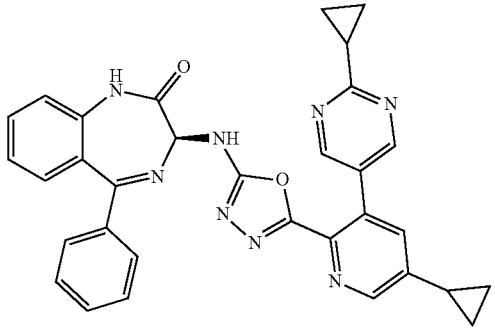 [SMILES: O=C1Nc2ccccc2C(c2ccccc2)=N[C@@H]1Nc1nnc(-c2ncc(C3CC3)cc2-c2cnc(C3CC3)nc2)o1]

or a pharmaceutically acceptable salt thereof.

8. The compound of claim 1 having the structure

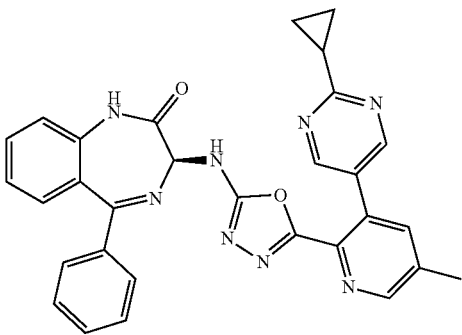 [SMILES: Cc1cnc(-c2nnc(N[C@H]3N=C(c4ccccc4)c4ccccc4NC3=O)o2)c(-c2cnc(C3CC3)nc2)c1]

or a pharmaceutically acceptable salt thereof.

9. A pharmaceutical composition comprising the compound of claim 1 and a pharmaceutically acceptable carrier or excipient.

10. A pharmaceutical composition comprising the compound of claim 4 and a pharmaceutically acceptable carrier or excipient.

11. A pharmaceutical composition comprising the compound of claim 5 and a pharmaceutically acceptable carrier or excipient.

12. A pharmaceutical composition comprising the compound of claim 6 and a pharmaceutically acceptable carrier or excipient.

13. A pharmaceutical composition comprising the compound of claim 7 and a pharmaceutically acceptable carrier or excipient.

14. A pharmaceutical composition comprising the compound of claim 8 and a pharmaceutically acceptable carrier or excipient.

15. A method for treating a respiratory syncytial virus infection in a human subject, comprising administering to the human subject a therapeutically effective amount of a compound of claim 1.

16. A method for treating a respiratory syncytial virus infection in a human subject, comprising administering to the human subject a therapeutically effective amount of a compound of claim 4.

17. A method for treating a respiratory syncytial virus infection in a human subject, comprising administering to the human subject a therapeutically effective amount of a compound of claim 5.

18. A method for treating a respiratory syncytial virus infection in a human subject, comprising administering to the human subject a therapeutically effective amount of a compound of claim 6.

19. A method for treating a respiratory syncytial virus infection in a human subject, comprising administering to the human subject a therapeutically effective amount of a compound of claim 7.

20. A method for treating a respiratory syncytial virus infection in a human subject, comprising administering to the human subject a therapeutically effective amount of a compound of claim 8.

* * * * *

UNITED STATES PATENT AND TRADEMARK OFFICE
CERTIFICATE OF CORRECTION

PATENT NO. : 11,912,695 B2
APPLICATION NO. : 17/574718
DATED : February 27, 2024
INVENTOR(S) : Kaicheng Zhu et al.

Page 1 of 1

It is certified that error appears in the above-identified patent and that said Letters Patent is hereby corrected as shown below:

In the Claims

At Column 139

In Claim 1, Line 25-35, delete " 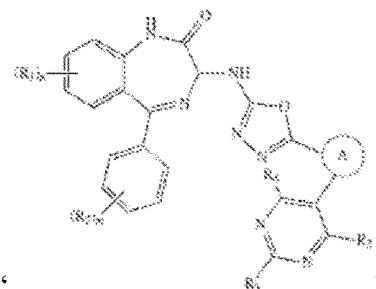 " and insert 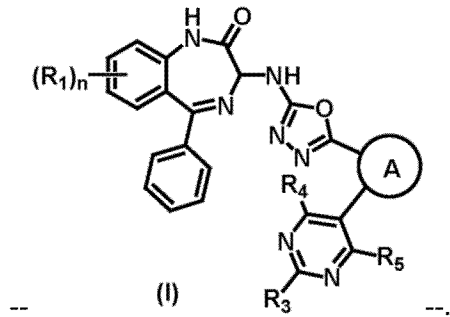 --.

Signed and Sealed this
Eighth Day of October, 2024

Katherine Kelly Vidal
Director of the United States Patent and Trademark Office